US006214973B1

(12) United States Patent
Ohtomo et al.

(10) Patent No.: US 6,214,973 B1
(45) Date of Patent: Apr. 10, 2001

(54) RESHAPED HUMAN ANTIBODY TO HUMAN MEDULLOBLASTOMA CELLS

(75) Inventors: Toshihiko Ohtomo; Koh Sato; Masayuki Tsuchiya, all of Gotenba (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 08/646,265

(22) PCT Filed: Oct. 19, 1994

(86) PCT No.: PCT/JP94/01763

§ 371 Date: Sep. 9, 1996

§ 102(e) Date: Sep. 9, 1996

(87) PCT Pub. No.: WO95/14041

PCT Pub. Date: May 26, 1995

(30) Foreign Application Priority Data

Nov. 19, 1993 (JP) .................................................. 5-291078

(51) Int. Cl.[7] .................................................. C07K 16/00
(52) U.S. Cl. .................................... 530/387.1; 424/133.1; 424/136.1
(58) Field of Search .............................. 424/130.1, 184.1, 424/133.1, 185.1, 134.1, 135.1, 138.1, 141.1, 152.1, 155.1, 136.1; 530/300, 387.3, 327–329, 387.7, 388.1, 388.15

(56) References Cited

U.S. PATENT DOCUMENTS 5,132,405 * 7/1992 Huston et al. .

FOREIGN PATENT DOCUMENTS

| 0 171 496 | 2/1986 | (EP) . |
| WO 90/07861 | 7/1990 | (EP) . |
| 0 533 199 | 3/1993 | (EP) . |
| 61-47500 | 3/1986 | (JP) . |
| WO 91/09967 * | 7/1991 | (WO) . |
| 92/19759 | 11/1992 | (WO) . |

OTHER PUBLICATIONS

Goshorn et al. Common structural features among monoclonal antibodies binding the same antigenic region of cytochrome c, J. Biol. Chem. 266:2134–2142, 1991.*
Kettleborough et al. Humanization of a mouse monoclonal antibody by CDR-grafting: the importance of framework residues on loop conformation, Protein Engineering 4:773–783, 1991.*
Kishima et al "Humanization of Mouse Monoclonal Antibody ONS–M21, Directed Against Human Medulloblastoma and Gliomas", 1994 Narito Kinin Conference.*
S. Moriuch et al., "Characterisation of a new mouse monoclonal antibody (ONS–M21) reactive with both Medullo blastomas and glimoas", (Nov. 1993), British Journal of Cancer, vol. 68, No. 5, p. 831–837.

J.S. Huston et al., "Protein engineering of antibody binding sites: Recovery of specific activity in an anti–digoxin Single–chain Fv analogue produced in . . .", (Aug. 1988), Proc. Nat. Acad, Sci. USA, vol. 85, p. 5879–5883.
"The 6th Annual Meeting, Society for Brain and Immunology Investigation of V region gene sequence of anti–medulloblastoma monoclonal antibody (ONS–M21)"., Moriuchi et al, Jul. 3, 1993.
"Molecular Approaches to Cancer Immunotherapy"., American Association for Cancer Research—Special Conference—Nov. 9, 1993. Ralph A. Reisfeld, chairperson.
The 16th Annual Meeting, The Molecular Biology Society of Japan–"Production of Humanized Mouse Monoclonal Antibody ONS–M21"., Ohtomo et al, Dec. 16, 1993.
The Annual Meeting, The Japan Neurosurgical Society–"Production of Humanized Anti–Medulloblastoma and Glioma Monoclonal Antibody (ONS–M21)"., Moriuchi et al., Dept. of Neurosurgery, Osaka Medical School, Apr. 1994.
The 39th Kinki Noshoyo Kenkyukai— "Humanization of Anti–Medulloblastoma Monoclonal Antibody (ONS–M21)" Moriuchi et al., Dept. of Neurosurgery, Osaka Medical School/Fuji–Gotemba Institute of Chugai Pharmaceutical Co., Ltd.; Apr. 16, 1994.
The 7th Annual Meeting, Society for Brain and Immunology–"Humanization of Mouse Monoclonal Antibody ONS–M21 Directed Against Human Medulloblastoma and Glioma"., Ohtomo et al., Chugai Pharmaceutical Co., Osaka Univ. Med., Neurosurgery, Jul. 2, 1994.
The Annual Meeting, The Japan Neurological Society–Humanization of Mouse Monoclonal Antibody ONS–M21 Directed Against Human Medulloblastoma and Glioma., Moriuchi et al., Dept. of Neurosurgery Osaka University Medical School/Fuji–Gotemba Institute of Chugai Pharmaceutical Co., Ltd. 1994.

(List continued on next page.)

Primary Examiner—Patricia A. Duffy
(74) Attorney, Agent, or Firm—Foley & Lardner

(57) ABSTRACT

The present invention discloses reshaped antibody to human medulloblastoma cells comprising:
(A) an L chain comprising:
 (1) a human L chain C region, and
 (2) an L chain V region comprising human L chain FRs and L chain CDRs of mouse monoclonal antibody ONS-M21 to human medulloblastoma cells; and,
(B) an H chain containing:
 (1) a human H chain C region, and
 (2) an H chain V region comprising human H chain FRs and H chain CDRs of mouse monoclonal antibody ONS-M21 to human medulloblastoma cells.

Since the majority of this reshaped human antibody is derived from a human antibody and mouse CDRs have a low level of antigenicity, the reshaped human antibody of the present invention has a low level of antigenicity in humans, and is therefore expected to be useful as a therapeutic agent and diagnostic tool for brain tumors such as medulloblastoma which strongly express antigen that is recognized by this antibody.

18 Claims, 10 Drawing Sheets

OTHER PUBLICATIONS

The 17th Annual Meeting, The Molecular Biology Society of Japan–"Construction of Single–Strand Fv Region of Humanized Anti–Medulloblastoma Antibody ONS–M21"., Ohtomo et al., Fuji–Gotemba Institute of Chugai Pharmaceutical Co., Ltd., Osaka University Medical School, Dept. of Neurosurgery, Dec. 1994.

The 8th Annual Meeting, Society for Brain and Immunology Humanization of Mouse Monoclonal Anti–body ONS–M21., Ohtomo et al., Fuji–Motemba Institute of Chugai Pharmaceutical Co., Ltd. Aug. 1995.

"Humanization of Mouse ONS–M21 Antibody with the Aid of Hybrid Variable Regions", Molecular Immunology, vol. 32, No. 6, pp. 407–416., Jun. 28, 1994.

P. Carter et al., "Humanization of an Anti–p185$^{HER2}$ Antibody for Human Cancer Therapy", Proc. Natl. Acad. Sci. USA, vol. 89, No. 10, May 1992, pp. 4285–4289.

K. Sato et al., "Reshaping a Human Antibody Inhibit the Interleukin 6–dependent Tumor Cell Growth", Cancer Research, vol. 53, Feb. 1993, pp. 851–856.

D. Colcher et al., "In Vivo Tumor Targeting of a Recombinant Single–Chain Antigen–Binding Protein", Journal of the National Cancer Institute, vol. 82, No. 14, Jul. 1990.

T. Ohtomo et al., "Humanization of Mouse ONS–M21 Antibody with the Aid of Hybrid Variable Regions", Molecular Immunology, vol. 32, No. 6, 1995, pp. 407–416.

* cited by examiner

SYNTHETIC OLIGONUCLEOTIDE

⇩

ANNEALING AND EXTENSION USING Ampli Taq DNA (1ST CYCLE)

⇩

COLLECTION OF SYNTHETIC GENE FOLLOWING ADDITION OF EXTERNAL PRIMERS RHP1 AND RHP2 AND ENHANCING BY Ampli Taq

⇩

RHP1 →
═══════════════════
        ← RHP2

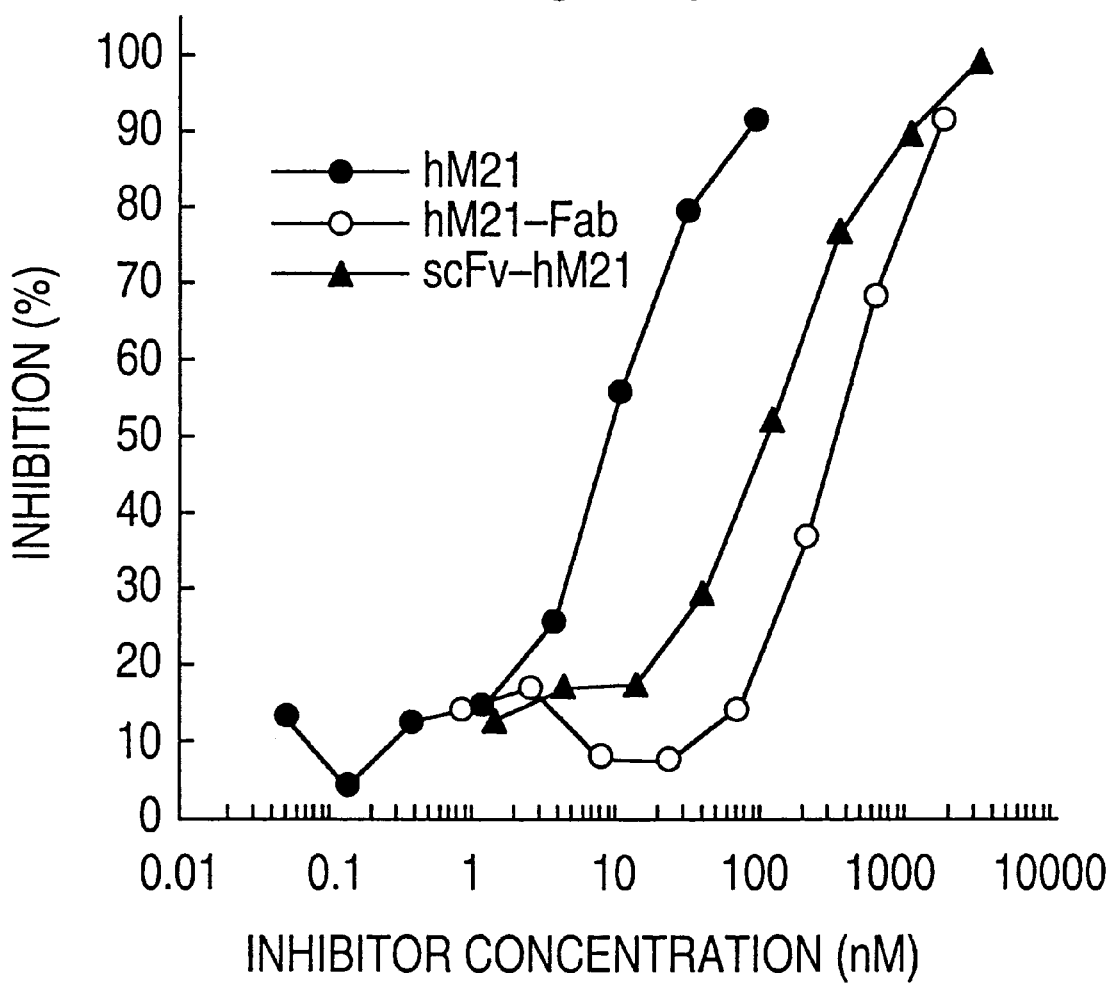

RESHAPED HUMAN ANTIBODY TO HUMAN MEDULLOBLASTOMA CELLS

TECHNICAL FIELD

The present invention relates to a human/mouse chimeric antibody comprising variable regions (V regions) of a mouse monoclonal antibody ONS-M21 to human medulloblastoma cells and constant regions (C regions) of human antibody; a reshaped human antibody wherein the complementarity determining regions (CDRs) of human light chain (L chain) V region and human heavy chain (H chain) V region, are substituted by the CDRs of mouse monoclonal antibody ONS-M21 to human medulloblastoma cells; and the L chain or H chain that composes that antibody.

Moreover, the present invention provides a DNA coding for the above-mentioned antibody, and particularly its V region. Moreover, the present invention relates to a vector containing the above-mentioned DNA, and particularly to an expression vector, along with a host transformed with said vector. Moreover, the present invention provides a process for producing chimeric antibody to human medulloblastoma cells as well as a process for producing a reshaped human antibody to human medulloblastoma cells.

In addition, the present invention relates to a single chain Fv composed by linking an H chain V region of a reshaped human antibody to human medulloblastoma cells and an L chain V region of said antibody. In addition, the present invention relates to a process for producing the above-mentioned single chain Fv by using DNA coding for said single chain Fv, a recombinant vector comprising said DNA, and a host transformed with said recombinant vector.

BACKGROUND ART

Medulloblastoma is one type of primitive neuroectodermal tumors which account for 40% of all brain tumors with glioma, and is a malignant brain tumor that frequently appears in children under 10 years of age, and particularly between the ages of 5 to 10 years. This tumor is a typical undifferentiated tumor that mimics morphology and arrangement patterns of undifferentiated cells that compose the embryonal medullary epithelium and matrical layer. It is considered to be an immature tumor that has the potential to differentiate into both nerve cells and glia cells (Tamura, K. et al., Cancer Res., 49, 5380–5384 (1989)). Since these types of malignant tumors exhibit sensitivity to radiation and chemotherapeutic agents, it is treated by radiotherapy, chemotherapy as well as surgery.

However, although these treatment methods alleviate symptoms temporarily, there are many cases of relapse and death within several years, with an average survival period being 15 months. The cause of this is believed to be that a recurrent cancer has resistance to chemotherapy and radiation.

On the other hand, accurate evaluation of brain tumors relies heavily on histological techniques, and requires an extremely high level of specialized knowledge as well as auxiliary diagnostic technology.

Thus, there is a pressing need for the development of diagnostic tools and therapeutic drugs that enable early diagnosis and fundamental treatment.

Several attempts have been made at treatment through the use of monoclonal antibodies that recognize medulloblastoma in the past as well (refer to Kemshead, J. T. et al., Int. J. Cancer, 31, 187–195 (1983), Allan, P. M. et al., Int. J. Cancer, 31, 591–598 (1983), Jones, D. et al., Br. J. Hematol., 57, 621–631 (1984), Gross, N. et al., Cancer Res., 46, 2998–2994 (1986), Wikstrand, C. D. et al., Cancer Res., 46, 5933–5940 (1986), Gibson, F. M. et al., Int. J. Cancer, 39, 554–559 (1987), Feickert, H. J. et al., Cancer Res., 49, 4338–4343 (1989), Jennings, M. T. et al., J. Neurol. Sci., 89, 63–78 (1989) and Takahashi, H. et al., Neurosurg., 27, 97–102 (1990)).

However, since nearly all of these antibodies also recognize normal tissue and other tumors, they have the disadvantage of being inappropriate for diagnosis and treatment of medulloblastoma.

Recently, brain tumor immunotherapy has been reported that uses a monoclonal antibody of human origin that reacts to the human glioma and exhibits ADCC activity (see, Japanese Unexamined Patent Publication No. 58-201994, Japanese Unexamined Patent Publication No. 59-137497 and Japanese Unexamined Patent Publication No. 4-356792).

Mouse monoclonal antibody exhibits a high degree of immunogenicity (also referred to as antigenicity) in humans. For this reason, their therapeutic value in humans is limited. Moreover, not only do mouse antibodies inhibit anticipated effects, but they cannot be administered frequently without provoking an immune reaction that brings about the risk of an allergic response that presents a problem for patients.

In order to solve these problems, a process for producing humanized antibody has been developed. Mouse antibody can be humanized by two methods. The simpler method involves the production of chimeric antibody wherein the variable region is derived from an original mouse monoclonal antibody, while the constant region is derived from a suitable human antibody. The resulting chimeric antibody contains a complete variable region of the original mouse antibody, and can be expected to bind antigen with the same specificity as the original mouse antibody.

Moreover, since the ratio of the protein sequence derived from sources other than humans is essentially reduced, it is predicted to have a low level of immunogenicity in comparison with the original mouse antibody. Although chimeric antibody effectively binds with antigen and has a low level of immunogenicity, there is still possibility of an immune reaction to the mouse variable region (LoBuglio, A. F. et al., Proc. Natl. Acad. Sci. USA, 86, 4220–4224, 1989).

Although more complex, the second method for humanizing mouse antibody considerably lowers the potential immunogenicity of the mouse antibody even more. In this method, complementarity determining regions (CDRs) from variable regions of a mouse antibody are transplanted into human antibody variable regions to produce a reshaped human antibody variable regions.

Next, these reshaped human antibody variable regions are linked to human antibody constant regions. Ultimately, the portion derived from the non-human protein sequence of a reshaped human antibody is only the CDRs and an extremely small portion of the framework (FR). CDRs comprise hyper-variable protein sequences. These sequences do not exhibit type-specific sequences. For these reasons, a reshaped human antibody containing mouse CDRs ought not to have immunogenicity stronger than naturally-occuring human antibody containing human CDRs.

The following references should be referred to with respect to reshaped human antibodies: Riechmann, L. et al., Nature, 332, 323–327, 1988; Verhoeyen M. et al., Science, 239, 1534–1536, 1988; Kettleborough, C. A. et al., Protein Engng., 4, 773–783, 1991; Maeda, H. et al., Human Antibodies and Hybridoma, 2, 124–134, 1991; Gorman S. D. et al., Proc. Natl. Acad. Sci. USA, 88, 4181–4185, 1991; Tempest P. R. et al., Bio/Technology, 9, 266–271, 1991; Co, M. S. et al., Proc. Natl. Acad. Sci. USA, 88, 2869–2873, 1991; Carter, P. et al., Proc. Natl. Acad. Sci. USA, 89, 4285–4289, 1992; Co, M. S. et al., J. Immunol., 148, 1149–1154, 1992; and, Sato, K. et al., Cancer Res., 53, 851–856, 1993.

As was previously stated, although it is predicted that a reshaped human antibody is useful for the purpose of therapeutical treatment, a reshaped human antibody to human medulloblastoma cells is not known. Moreover, there are no methods for producing a reshaped human antibody that can be universally applied to any specific antibody. Thus, various contrivances are necessary to produce a reshaped human antibody to a specific antigen that has sufficient activity (for example, Sato, K. et al., Cancer Res., 53, 1–6 (1993)).

The inventors of the present invention isolated and established a medulloblastoma cell line (ONS-76) from the cerebellum of medulloblastoma patients (Tamura, K. et al., Cancer Res., 49, 5380–5384 (1989)). By then immunizing mice with said medulloblastoma cell line ONS-76, a mouse monoclonal antibody (ONS-M21) was found that specifically recognizes human medulloblastoma but does not cross-react with normal brain tissue or peripheral blood cells (Moriuchi, S. et al., Br. J. Cancer, 68, 831–837 (1993)). Since antigen recognized by this antibody is strongly expressed in brain tumors such as medulloblastoma and some gliomas, it is anticipated to be used as a diagnostic tool as well as directly destroy cancer cells by inducing ADCC and CDC or conjugating with toxins and radioisotopes.

DISCLOSURE OF THE INVENTION

Thus, the present invention relates to a reshaped human antibody of a mouse monoclonal antibody ONS-M21 to human medulloblastoma cells. In addition, the present invention provides a human/mouse chimeric antibody useful during the course of producing said reshaped human antibody. Moreover, the present invention relates to a genetic engineering process for producing a reshaped human antibody and a chimeric antibody of mouse monoclonal antibody ONS-M21.

More specifically, the present invention relates to (1) L chain V region of mouse monoclonal antibody ONS-M21 to human medulloblastoma cells; and, (2) H chain V region of mouse monoclonal antibody ONS-M21 to human medulloblastoma cells.

The present invention also relates to a chimeric antibody to human medulloblastoma cells comprising:

(1) L chain containing a human antibody L chain C region, and the above-mentioned L chain V region of mouse monoclonal antibody ONS-M21 to human medulloblastoma cells; and, (2) H chain containing human antibody H chain C region, and the H chain V region of mouse monoclonal antibody ONS-M21 to human medulloblastoma cells.

The present invention moreover relates to a reshaped human antibody of mouse monoclonal antibody ONS-M21 to human medulloblastoma cells comprising:

reshaped human L chain V region comprising (1) framework regions (FRs) of human antibody L chain V region, and (2) CDRs of L chain V region of mouse monoclonal antibody ONS-M21 to human medulloblastoma cells; and, reshaped human H chain V region comprising (1) FRs of human antibody H chain V region, and (2) CDRs of H chain V region of mouse monoclonal antibody ONS-M21 to human medulloblastoma cells.

In addition, the present invention relates to L chain or H chain polypeptides that compose the various above-mentioned antibodies as well as DNA coding for them.

Moreover, the present invention relates to expression vectors containing the above-mentioned DNA as well as a host transformed by them.

In addition, the present invention relates to a process for producing chimeric antibody to human medulloblastoma cells as well as a process for producing a reshaped human antibody to human medulloblastoma cells.

In addition, the present invention relates to a single chain Fv region composed by linking an H chain V region of a reshaped human antibody to human medulloblastoma cells and an L chain V region of said monoclonal antibody.

Moreover, the present invention relates to DNA coding for the above-mentioned single chain Fv region, recombinant vectors that contain said DNA and a host transformed by said recombinant vectors.

Moreover, the present invention relates to a process for producing a single chain Fv region characterized by culturing the above-mentioned host and recovering a single chain Fv region from said culture.

BRIEF DESCRIPTION OF THE DRAWINGS

FIG. 10 is a graph that indicates an antigen binding activity of the single chain Fv region of the present invention (scFv-hM21) in comparison with an antigen binding activity of reshaped human ONS-M21 antibody and the Fab fragment of said antibody using for the parameter the inhibition of antigen binding by mouse monoclonal antibody ONS-M21.

DETAILED EXPLANATION

Figure 1:
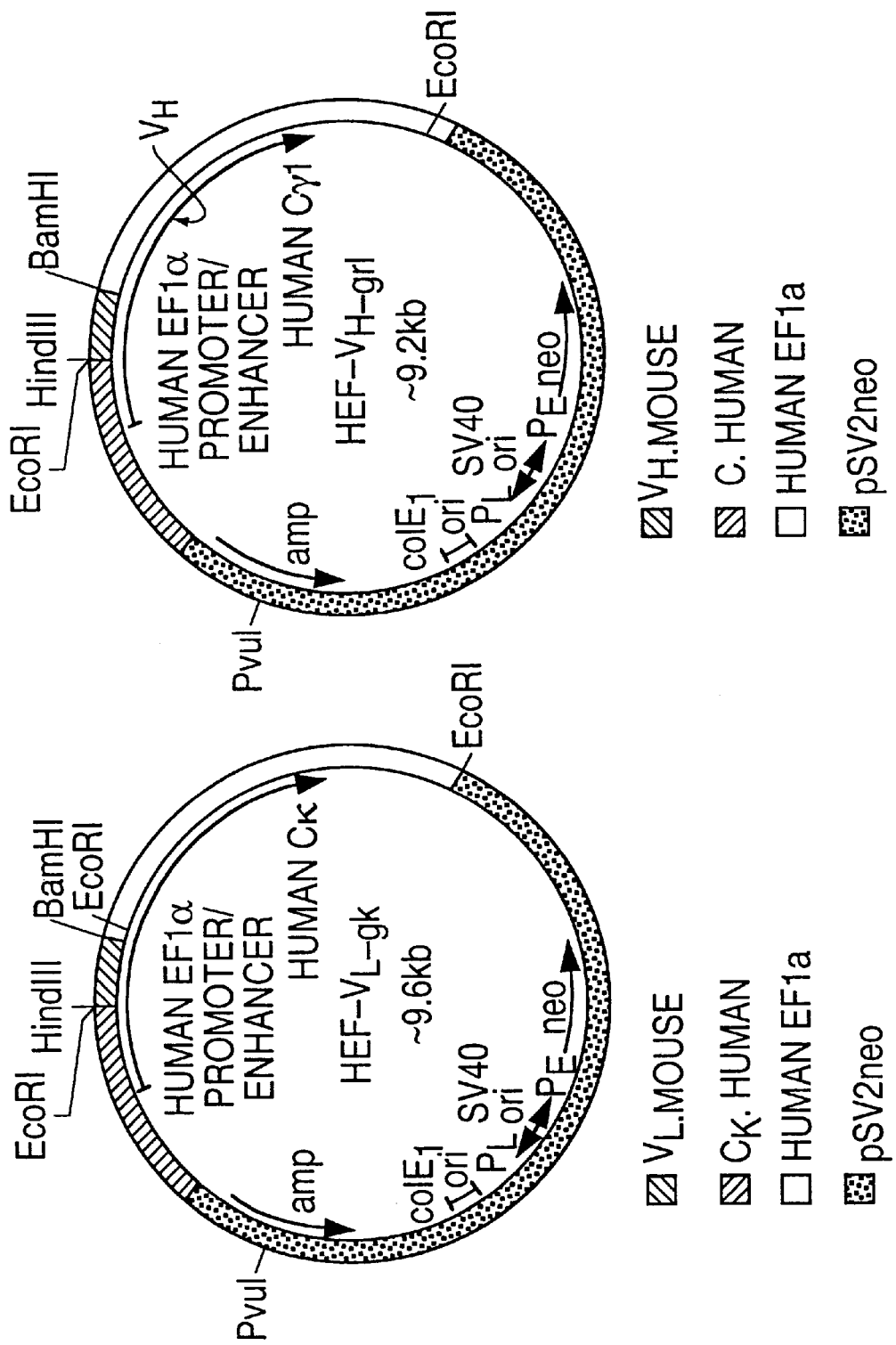
FIG. 1 indicates expression plasmids HEF-VL-gκ and HEF-VH-gγ1 comprising human EF1-α promoter/enhancer useful for expression of an L chain and H chain, respectively.

Cloning of DNA Coding for Mouse Antibody V Region

In order to clone a DNA coding for a V region of a mouse monoclonal antibody to human medulloblastoma cells, after preparing mRNA from mouse monoclonal antibody-producing cells, said mRNA is converted to double-stranded DNA using known method followed by amplifying the target DNA using polymerase chain reaction (PCR). It is necessary to prepare hybridoma producing a monoclonal antibody to human medulloblastoma cells for the supply source of mRNA. One example of this type of hybridoma is ONS-M21. The process for producing hybridoma ONS-M21 is described later in Reference Example 1.

(1) Obtaining of Whole RNA

In order to obtain whole RNA, in the present invention, after destroying hybridoma cells and treating with guanidine thiocyanate, cesium chloride density gradient centrifugation was performed (Chirgwin, J. M. et al., Biochemistry, 18, 5294–5299, 1979). However, methods already used during cloning of other protein genes can also be used, examples of which include treatment with surfactant in the presence of a ribonuclease inhibitor such as vanadium compounds followed by treatment with phenol (Berger, S. L. et al., Biochemistry, 18, 5143–5149, 1979).

(2) Preparation of Double-Stranded cDNA

In order to obtain single-stranded DNA from whole RNA obtained in the manner described above, single-stranded DNA complementary to whole RNA (cDNA) can be synthesized by using the whole RNA as a template and treating with reverse transcriptase using oligo(dT) complementary to its polyA chain on the 3' terminal as primer (Larrik, J. W. et al., Bio/Technology, 7, 934–938, 1989). In addition, a random primer may also be used at that time.

(3) Amplification of Mouse Antibody V Region by Polymerase Chain Reaction (PCR)

Next, specific amplification of mouse antibody V region is performed from the above-mentioned cDNA using polymerase chain reaction (PCR). The primer described in Jones, S. T. et al., Bio/Technology, 9, 88–89, 1991 can be used for amplification of the mouse antibody V region. In the determining of the primer used for cloning of mouse monoclonal antibody ONS-M21 produced by hybridoma ONS-M21, it is necessary to type the H chain and L chain and determine the form of both chains.

As a result of performing typing of ONS-M21 antibody using a mouse monoclonal antibody isotyping kit (Amersham International Plc.), it was clear that ONS-M21 antibody has a Cκ type L chain and γ-1C type H chain. Typing of ONS-M21 is described later in Reference Example 2.

Next, in order to amplify the kappa (κ) type L chain V region of mouse monoclonal antibody using polymerase chain reaction (PCR), 11 types of oligonucleotide primers indicated in SEQ ID NOS: 1 to 11 (Mouse Kappa Variable; MKV) and the oligonucleotide primer shown in SEQ ID NO: 12 (Mouse Kappa Constant; MKC) are used for the 5'-terminal primer and 3'-terminal primer, respectively.

The above-mentioned MKV primer hybridizes with the DNA sequence coding for the mouse kappa type L chain leader sequence, while the above-mentioned MKC primer hybridizes with the DNA sequence coding for the mouse kappa type L chain C region.

In order to amplify the H chain V region of mouse monoclonal antibody, the 12 types of oligonucleotide primers indicated in SEQ ID NOS: 13 to 24 (Mouse Heavy Variable; MHV) and the oligonucleotide indicated in SEQ ID NO: 25 (Mouse Heavy Constant, MHC) are used for the 5'-terminal primer and 3'-terminal primer, respectively.

Furthermore, in the present embodiment, a 5'-terminal primer contains the sequence GTCGAC that provides a site to be cleaved by restriction enzyme SalI near the 5'-terminal, while a 3'-terminal primer contains the nucleotide sequence CCCGGG that provides a site to be cleaved by restriction enzyme XmaI near the 5'-terminal. Other restriction enzyme cleavage sites may be used for these restriction enzyme cleavage sites provided they can be used for subcloning the target DNA fragment coding for the variable region in a cloning vector.

Next, in order to obtain a DNA fragment coding for a target variable region of a mouse monoclonal antibody, after cleaving the amplification product with restriction enzymes SalI and XmaI, isolation and purification is performed using low melting temperature agarose or a column (PCR product purification kit (Qiagen), DNA purification kit (Geneclean II) and so forth). On the other hand, a plasmid is obtained that contains a DNA fragment coding for a target variable region of mouse monoclonal antibody by cleaving a suitable cloning vector such as plasmid pUC19 with the same restriction enzymes SalI and XmaI, and ligating the above-mentioned DNA fragment to this pUC19.

The cloned DNA can be sequenced using any commonly employed method such as an automated DNA sequencer (Applied Biosystems Inc.).

Cloning of the target DNA and determination of its sequence are described in detail in Examples 1 and 2.

Complementarity Determining Region (CDR)

A pair of V regions of L chain and H chain forms an antigen binding site. The variable regions of the L chain and H chain comprises four relatively well-preserved framework regions linked with three hyper-variable or complementarity determining regions (CDR) (Kabat, E. A. et al., "Sequences of Proteins of Immunological Interest", US Dept. Health and Human Services 1983).

The majority of the portions of the above-mentioned four framework regions (FRs) employ a β-sheet structure. As a result, three CDRs form a loop. The CDRs may also form a portion of the β-sheet structure in certain cases. The three CDRs are maintained at positions that are three-dimensionally extremely close to each other by the FRs, and contribute to the formation of an antigen binding site together with three CDRs of the region with which it constitutes a pair.

These CDRs can be found based on the empirical rules of Kabat, E. A. et al., "Sequences of Proteins of Immunological Interest" by comparing the amino acid sequence of the V region of the resulting antibody with known amino acid sequences of V regions of known antibodies. A detailed explanation of this is given in Example 3.

Production of Chimeric Antibody

Prior to designing the reshaped human V region of antibody to human medulloblastoma cells, it is necessary to confirm that the CDRs used actually form an antigen binding region. Chimeric antibody was produced for this purpose. Moreover, the amino acid sequence of mouse anti-human medulloblastoma cell antibody, predicted from the nucleotide sequence of cloned DNA of monoclonal antibody ONS-M21 described in Example 1, was compared with the V regions of known mouse and human antibodies.

Once a DNA fragment is cloned coding for the mouse L chain and H chain V regions of monoclonal antibody ONS- M21, chimeric anti-human medulloblastoma cell antibody can be obtained by linking these mouse V regions with DNA coding for human antibody constant region and then expressing them.

The basic method for producing chimeric antibody comprises linking a mouse leader sequence and V region sequence in cloned cDNA with a sequence coding for human antibody C region already present in a mammalian cell expression vector.

The above-mentioned human antibody C region can be any human L chain C region or H chain C region,, examples of which include human L chain Cκ or H chain γ-1C and γ-4C.

In order to produce chimeric antibody, two types of expression vectors are prepared. These vectors are an expression vector comprising DNA coding for a mouse L chain V region and a human L chain C region under the control by an expression control region such as an enhancer/promoter type, and an expression vector comprising DNA coding for a mouse H chain V region and a human H chain C region under the an expression control region such as an enhancer/promoter type. Next, host cells such as mammalian cells are co-transformed with these expression vectors after, which the transformed host is cultured in vitro or in vivo to produce chimeric antibody (e.g. WO91-16928).

Alternatively, DNA coding for a mouse L chain V region and a human L chain C region, and DNA coding for a mouse L chain V region and a human H chain C region may be introduced into a single expression vector, host cells are transformed using said vector, and this transformed host is then cultured in vivo or in vitro to produce the desired chimeric antibody.

A description of production of chimeric antibody is provided in Example 4.

A cDNA coding for a mouse ONS-M21 κ type L chain leader region and a V region is subcloned using PCR and linked to an expression vector containing DNA coding for human genome L chain CK chain region. cDNA coding for the γ1 type H chain leader and V regions of mouse ONS-M21 antibody is subcloned using PCR, and linked to an expression vector containing genome DNA coding for human γ-1C region.

Using specially designed PCR primers, cDNA coding for the V region of mouse ONS-M21 is provided with a suitable nucleotide sequence at its 5'-terminal and 3'-terminal to facilitate their insertion into the expression vector as well as to ensure that they function suitably in said expression vector (for example, transcription efficiency is improved in the present invention by the introduction of Kozak's sequence). Next, the V region of mouse ONS-M21, obtained by amplification by PCR, was inserted into an HEF expression vector (FIG. 1) already containing the desired human C region using these primers. These vectors are suitable for transient or stable expression of genetically engineered antibodies in various mammalian cell systems.

The chimeric ONS-M21 antibody demonstrated an activity to bind to human medulloblastoma cells. Thus, this indicated that a correct mouse v region had been cloned, and that the sequence had been determined.

Design of Reshaped Human ONS-M21 Antibody V Region

In order to produce a reshaped human antibody in which the CDRs of mouse monoclonal antibody are grafted onto a human antibody, it is preferable that a high degree of homology exists between the FRs of the mouse monoclonal antibody and the FRs of the human antibody. Thus, the V regions of the L chain and H chain of mouse ONS-M21 antibody were compared with the V regions of all known antibodies for which structure has been determined using the Protein Data Bank.

The L chain V region of mouse ONS-M21 most closely resembles the consensus sequence of subgroup IV of human L chain V region (HSGIV), demonstrating homology of 61.9%.

In a comparison of the L chain V region of mouse ONS-M21 antibody with known human antibody L chain V regions, homology of 60.4% was demonstrated with human L chain V region REI, a member of subgroup I of the human L chain V region. Thus, the FRs of REI were used as a starting material for preparation of reshaped human ONS-M21 antibody L chain V region.

Sixteen versions of reshaped human ONS-M21 antibody L chain V region were designed (versions "a"-"p"). In the first version (version "a"), human FRs were identical to FR of version "a" of the L chain V region of reshaped human PM-1 described in WO92-19759, which is based on REI present in reshaped human CAMPATH-1H antibody (Riechmann, L. et al., Nature, 332. 323–327 (1988)), while mouse CDRs were identical to the CDRs in the L chain V region of mouse ONS-M21 antibody.

Tables 1 and 2 show the amino acid sequences of the L chain V region of mouse ONS-M21 antibody, the FRs of REI, and the L chain V region of the 16 versions of reshaped ONS-M21 antibody.

TABLE 1

Design of Reshaped Human ONS-M21 L Chain V Regions

| | | FR1<br>1          2<br>12345678901234567890123 | CDR1<br>3<br>45678901234 | FR2<br>4<br>567890123456789 | CDR2<br>5<br>0123456 |
|---|---|---|---|---|---|
| (residues 21–76 of SEQ ID NO: 27) | ONS-M21VL | DIVMTQSQKFMSTSVGDRVSVTC | KASQNVGTNVA | WYQQKPGQSPKPLIY | SASYRYS |
| (residues 1–38 of SEQ ID NO: 112) | RE1 | DIQMTQSPSSLSASVGDRVTITC | | WYQQKPGKAPKLLIY | |
| (residues 1–55 of SEQ ID NO: 43) | RVLa | DIQMTQSPSSLSASVGDRVTITC | KASQNVGTNVA | WYQQKPGKAPKLLIY | SASYRYS |
| (residues 1–55 of SEQ ID NO: 47) | RVLb | — | — | — | — |

TABLE 1-continued

Design of Reshaped Human ONS-M21 L Chain V Regions

|  |  | FR1<br>1          2<br>12345678901234567890123 | CDR1<br>3<br>45678901234 | FR2<br>4<br>567890123456789 | CDR2<br>5<br>0123456 |
|---|---|---|---|---|---|
| (residues 1–55 of SEQ ID NO: 51) | RVLc | —————————————————————— | ——————————— | ——————————————— | ——————— |
| (residues 1–55 of SEQ ID NO: 53) | RVLd | —————————————————————— | ——————————— | ——————————————— | ——————— |
| (residues 1–55 of SEQ ID NO: 57) | RVLe | ——————————————SV—————— | ——————————— | ——————————————— | ——————— |
| (residues 1–55 of SEQ ID NO: 59) | RVLf | ——————————————SV—————— | ——————————— | ——————————————— | ——————— |
| (residues 1–55 of SEQ ID NO: 63) | RVLg | ——————————————SV—————— | ——————————— | ——————————————— | ——————— |
| (residues 1–55 of SEQ ID NO: 65) | RVLh | —————————————————————— | ——————————— | ——————————————— | ——————— |
| (residues 1–55 of SEQ ID NO: 69) | RVLi | ——————————————SV—————— | ——————————— | ————QS—P———————— | ——————— |
| (residues 1–55 of SEQ ID NO: 73) | RVLj | ——————————————SV—————— | ——————————— | ————QS—P———————— | ——————— |
| (residues 1–55 of SEQ ID NO: 75) | RVLk | ——————————————SV—————— | ——————————— | ——————————————— | ——————— |
| (residues 1–55 of SEQ ID NO: 77) | RVLl | ——————————————SV—————— | ——————————— | ————QS—P———————— | ——————— |
| (residues 1–55 of SEQ ID NO: 81) | RVLm | ——————————————SV—————— | ——————————— | ————QS—P———————— | ——————— |
| (residues 1–55 of SEQ ID NO: 85) | RVLn | ————QKF——————————————— | ——————————— | ————QS————————— | ——————— |
| (residues 1–55 of SEQ ID NO: 87) | RVLo | —————————————————————— | ——————————— | ————QS—P———————— | ——————— |
| (residues 1–55 of SEQ ID NO: 91) | RVLp | —————————————————————— | ——————————— | ————————P—————— | ——————— |

TABLE 2

Design of Reshaped Human ONS-M21 L Chain V Regions (cont.)

|  |  | FR3<br>6          7          8<br>78901234567890123456789012345678 | CDR3<br>9<br>901234567 | FR4<br>1<br>0<br>8901234567 |
|---|---|---|---|---|
| (residues 77–127 of SEQ ID NO: 27) | ONS-M21VL | GVPDRFTGSGSGTDFTLTITNVQSEDLADYFC | QQYNSYPRA | FGGGTKLEIK |
| (residues 39–80 of SEQ ID NO: 112) | RE1 | GVPSRFSGSGSGTD<u>F</u>TFTISSLQPEDIATYYC |  | FGQGTK<u>VE</u>IK |
| (residues 56–106 of SEQ ID NO: 43) | RVLa | GVPSRFSGSGSGTDFTFTISSLQPEDIATYYC | QQYNSYPRA | FGQGTKVEIK |
| (residues 56–106 of SEQ ID NO: 47) | RVLb | ——————————————Y———————————————— | ————————— | —————————— |
| (residues 56–106 of SEQ ID NO: 51) | RVLc | ——————————————————————————F———— | ————————— | —————————— |
| (residues 56–106 of SEQ ID NO: 53) | RVLd | ——————————————————————————F———— | ————————— | —————————— |

TABLE 2-continued

Design of Reshaped Human ONS-M21 L Chain V Regions (cont.)

| | | FR3 6 7 8 7890123456789012345678901 2345678 | CDR3 9 901 2345 67 | FR4 1 0 8901 234567 |
|---|---|---|---|---|
| (residues 56–106 of SEQ ID NO: 57) | RVLe | — | — | — |
| (residues 56–106 of SEQ ID NO: 59) | RVLf | ——————————F— | — | — |
| (residues 56–106 of SEQ ID NO: 63) | RVLg | ————L————————F— | — | — |
| (residues 56–106 of SEQ ID NO: 65) | RVLh | ————L———————— | — | — |
| (residues 56–106 of SEQ ID NO: 69) | RVLi | ————L————————F— | — | — |
| (residues 56–106 of SEQ ID NO: 73) | RVLj | ————L———————D—F— | — | — |
| (residues 56–106 of SEQ ID NO: 75) | RVLk | ————L———————D—F— | — | — |
| (residues 56–106 of SEQ ID NO: 77) | RVLl | — | — | — |
| (residues 56–106 of SEQ ID NO: 81) | RVLm | — | — | — |
| (residues 56–106 of SEQ ID NO: 85) | RVLn | — | — | — |
| (residues 56–106 of SEQ ID NO: 87) | RVLo | — | — | — |
| (residues 56–106 of SEQ ID NO: 91) | RVLp | — | — | — |

Note:

Those underlined amino acids in the FRs of REI indicate locations of amino acids that differ from those of the amino acid sequence of human REI (Palm, W. et al., Hoppe-Seyler's, Z. Physiol. Chem., 356, 167–191, 1975). The H chain V region of mouse ONS-M21 most closely resembles the consensus sequence of human H chain V region subgroup I (HSGI), exhibiting homology of 57.9%. In a comparison of the H chain V region of mouse ONS-M21 antibody with known human antibody H chain V regions, it resembled extremely closely the H chain V region of human antibody Eu, a member of human H chain V region subgroup I, from FRI to FR3 (Cunningham, B. J. et al., Biochemistry, 9, 3161, 1970). Moreover, the size of the CDRs were also extremely similar between mouse ONS-M21 antibody and human antibody Eu.

Consequently, the FRs of human antibody Eu were used as a starting material for preparation of the H chain V region of a reshaped human ONS-M21 antibody.

However, since the amino acid sequence of the FR4 of the human antibody Eu has a sequence that differs from the human antibody subgroup I consensus sequence, it was decided to use the amino acid sequence of the FR4 of human antibody ND (Kenten, J. H. et al., Proc. Natl. Acad. Sci. USA, 79, 6661–6665 (1982)), whose V region belongs to subgroup I, for the FR4 in this case.

H chain V regions of reshaped human ONS-M21 antibody were designed. Amino acids at positions 27, 28, 29 and 30 of human FR1 and position 94 of FR3 were made to be identical to the amino acids of mouse ONS-M21.

TABLE 3

Design of Reshaped Human ONS-M21 H Chain V Region

| | | | FR1 1 2 3 12345678901234567890123456 7890 | CDR1 12345 | FR2 4 67890123456789 |
|---|---|---|---|---|---|
| (residues 20–136 of SEQ ID NO:29) | | ONS-M21VH | EVQLQQSGAELVKPGASVKLSCTASGFNIK | DTYIH | WAKQRPEQGLEWIG |
| (SEQ ID NO:113) | | EU | QVQLVQSGAEVKKPGSSVKVSCKASGGTFS | | WVRQAPGQGLEWMG |
| (residues 23–139 of SEQ ID NO:109) | | RVHa | QVQLVQSGAEVKKPGSSVKVSCKASG<u>FNIK</u> | DTYIH | WVRQAPGQGLEWMG |

TABLE 3-continued

Design of Reshaped Human ONS-M21 H Chain V Region

```
                        CDR2                           FR3
                 5         6             7         8          9
                 01223456789012345    6789012345678901222345678901234
                         A                              ABC
      ONS-M21VH  RIDPADGNTKYDPKFQG    KATITADTSSNTAYLQLSSLTSEDTAVYYCAS
      EU                              RVTITADESTNTAYMELSSLRSEDTAFYFCAG
      RVHa       RIDPADGNTKYDPKFQG    RVTITADESTNTAYMELSSLRSEDTAFYFCAS

CDR3          FR4
                    1            1
                    0            1
                 56789012    34567890123
      ONS-M21VH  AYYVNQDY    WGQGTSVTVSS
      EU
(SEQ ID NO:114)  ND                    WGQGTTVTVSS
      RVHa       AYYVNQDY    WGQGTTVTVSS
```

Production of Reshaped Human ONS-M21 Antibody

Production of reshaped human ONS-M21 antibody V region is described in detail in Example 5.

A reshaped human ONS-M21 antibody of the present invention comprises:

(A) L chains lack comprising:
 (1) a human L chain C region, and
 (2) an L chain V region comprising human L chain FRs and L chain V region CDRs of mouse monoclonal antibody ONS-M21 to human medulloblastoma; and, (B) H chains lack comprising:
 (1) a human H chain C region, and
 (2) an H chain V region comprising human H chain FRs and H chain V region CDRs of mouse monoclonal antibody ONS-M21 to human medulloblastoma.

In order to produce a reshaped human antibody that possesses sufficient activity with respect to a specific antigen, it is preferable to substitute a portion of the amino acid sequence of the above-mentioned human FRs.

In a preferable embodiment, the amino acid of position 46 of FR2 of the above-mentioned L chain V region should be proline, or the amino acids of positions 42, 43 and 46 should preferably be amino acids derived from mouse FR such as glutamine, serine and proline, or more preferably, should have the amino acid sequence of RVLi, RVLj, RVL1, RVLm, RVLO or RVLp in Tables 1 and 2.

The above-mentioned human L chain C region can be any human L chain C region, an example of which is the human κC region. The above-mentioned H chain C region can also be any human H hain C region, examples of which include the human γ-1C and human γ-4C regions. Alternatively, a toxin or radioisotope may be bound instead of the above-mentioned human L chain C region and/or above-mentioned human H chain C region.

In order to produce a reshaped human antibody, two types of expression vectors are prepared. These are an expression vector containing DNA coding for a previously defined reshaped human L chain under an expression control region such as an enhancer/promoter type, and another expression vector that contains DNA coding for a previously defined reshaped human H chain under an expression control region such as an enhancer/promoter type. Next, host cells such as mammalian cells are simultaneously transformed using these expression vectors after which the transformed host is cultured in vitro or in vivo to produce a reshaped human antibody (e.g. WO91-16927).

Alternatively, DNA coding for a reshaped L chain and DNA coding for a reshaped human H chain may be introduced into a single expression vector, host cells are transformed with this vector, and this transformed host is then cultured in vivo or in vitro to produce a desired reshaped human antibody.

Moreover, Fab or Fv, or Fv-linked single-chain Fv, can be produced in a suitable host and used for the purpose described above (refer, for example, to Bird, et al., TIBTECH, 9, 132–137 (1991)).

Chimeric antibody or humanized antibody produced by culturing a transformed host transformed with a gene coding for the desired chimeric antibody or humanized antibody in the manner described above can then be isolated from inside or outside cells and purified to homogeneity.

Furthermore, separation and purification of the chimeric antibody or humanized antibody, which is the target protein of the present invention, can be performed using a protein A agarose column. In addition, other isolation and purification methods commonly used with proteins may also be used, and there are no limitations whatsoever on those methods. For example, chimeric antibody or humanized antibody can be isolated and purified by suitably selecting and combining various types of chromatography, ultrafiltration, salting, dialysis and so forth.

Any expression system can be used for producing a chimeric antibody or a reshaped human antibody to human medulloblastoma cells of the present invention, examples of which include eucaryotic cells such as animal cells including established mammalian cell systems, mold cells and yeast cells as well as procaryotic cells such as bacterial cells including *Escherichia coli* cells. A chimeric antibody or a reshaped antibody of the present invention is preferably expressed in mammalian cells such as COS cells or CHO cells.

In these cases, useful, conventional used promoters can be used for expression in mammalian cells. For example, the use of human cytomegalovirus immediate early (HCMV) promoter is preferable. Examples of expression vectors containing HCMV promoter include HCMV-$V_H$-HCγ1 and HCMV-$V_L$-HCκ derived from pSV2neo (refer to International Unexamined Application WO92-19759).

In addition, promoters derived from mammalian cells such as promoters of viruses including retrovirus, polio virus, adenovirus and simian virus 40 (SV40) as well as human polypeptide chain elongation factor 1α (HEF-1α) should be used for promoters of genetic expression in mammalian cells that can be used for the present invention. For example, in the case of using SV40 promoter, expression can be easily carried out by following the method Mulligan, R. C. et al. (Nature, 277, 108–114 (1979)), or in the case of using HEF-1α promoter, the method of Mizushima, S. et al. (Nucleic Acids Research, 18, 5322 (1990)).

Those derived from SV40, polio virus, adenovirus, bovine papilloma virus (BPV) and so forth can be used for an origin of replication. Moreover, in order to amplify the number of gene copies in the host cell system, the expression vector can contain phosphotransferase APH(3')II or I (neo) gene, thymidine kinase (TK) gene, *Escherichia coli* xanthine-guanine phosphoribosyl transferase (Ecogpt) gene and dihydrofolic acid reductase (DHFR) and so forth as selection markers.

In addition, the present invention also provides a single-chain Fv composed by linking an H chain V region and an L chain V region of a reshaped human antibody to human medulloblastoma cells. The H chain V region and L chain V region in this scFv polypeptide are preferably linked by a linker, and more preferably, a peptide linker.

The H chain V region in the single-chain Fv may be any of the H chain V regions of reshaped human antibody previously described.

An H chain V region comprises 4 FRs, and 3 CDRs having the amino acid sequences defined below:
  CDR1: (SEQ ID NO: 115) Asp Thr Tyr Ile His
  CDR2: (SEQ ID NO: 116) Arg Ile Asp Pro Ala Asp Gly Asn Thr Lys Tyr Asp Pro Lys Phe Gln Gly
  CDR3: (SEQ ID No: 117) Ala Tyr Tyr Val Asn Gln Asp Tyr
or a portion thereof.

In addition, an L chain V region comprises 4 FRs, and 3 CDRs having the amino acid sequences defined below:
  CDR1: (SEQ ID NO: 118) Lys Ala Ser Gln Asn Val Gly Thr Asn Val Ala
  CDR2: (SEQ ID NO: 119) Ser Ala Ser Tyr Arg Tyr Ser
  CDR3: (SEQ ID NO: 120) Gln Gln Tyr Asn Ser Tyr Pro Arg Ala,
or a portion thereof.

A specific example of a single-chain Fv is that comprising an H chain V region consisting of the amino acid sequence from amino acid 1 to 116 in the amino acid sequence described in SEQ ID NO: 99, and an L chain V region consisting of the amino acid sequence from amino acid 1 to 106 in the amino acid sequence described in any of SEQ ID NOS: 43, 47, 51, 53, 57, 59, 63, 65, 69, 73, 75, 77, 81, 85, 87 or 91.

In addition, a preferable example of a single-chain Fv is that comprising an H chain V region consisting of the amino acid sequence from amino acid 1 to 116 in the amino acid sequence described in SEQ ID NO: 99, and an L chain V region consisting of the amino acid sequence from amino acid 1 to 106 in the amino acid sequence described in SEQ ID NO: 91.

These V regions are preferably linked by polypeptide linkers. Although examples of polypeptide linkers include any single-chain Fv comprising 12 to 19 amino acids, a specific example of a peptide fragment that can be used is the peptide fragment composed of Gly Gly Gly Gly Ser Gly Gly Gly Gly Ser Gly Gly Gly Gly Ser (SEQ ID NO: 111).

An example of an amino acid sequence of a single-chain Fv is shown in SEQ ID NO: 109. A single-chain Fv that possesses this amino acid sequence is referred to as scFv-hM21 in the present invention, and is explained in detail in Example 6.

A DNA coding for the single-chain Fv of the present invention is obtained by using as a template a DNA coding for an H chain or H chain V region of a reshaped human ONS-M21 antibody and a DNA coding for an L chain or L chain V region of reshaped human ONS-M21 antibody, both of which were previously explained in detail, and then amplifying a DNA portion coding for a desired amino acid sequence in those sequences by PCR using a pair of primers that specify both ends. Example 6 provides a detailed description of a method for preparing a DNA coding for single-chain Fv comprising an H chain V region and an L chain V region version "p". Since the amino acid sequences of L chain V region versions "la" to "o" along with methods for preparing DNA coding for them are described in detail, by applying a method in which version "p" is used for those versions, DNA can be produced that code for various single-chain Fvs of the present invention.

In addition, once DNA coding for single-chain Fv has been produced, expression vectors comprising that DNA as well as hosts transformed with said expression vectors can be obtained in accordance with routine methods. In addition, single-chain Fvs can be obtained by using those hosts in accordance with conventional methods. Specific examples of these are described in detail in Example 6.

As a result of comparing the antigen binding ability of scFv-hM21 with that of humanized ONS-M21 antibody and Fab fragment using for the indicator the degree of inhibition of binding of mouse ONS-M21 antibody to ONS-76 cells, scFv-hM21 was found to exhibit binding inhibition equal to that of Fab fragment. On the basis of the above, a single-chain Fv was able to be successfully constructed that possesses the same degree of affinity as the original antibody.

In general, since single-chain Fvs are considered to exhibit superior mobility into tissue and tumors in comparison with whole IgG, this successfully constructed scFv-hM21 is expected to be used in the future in imaging by RI labeling as well as a therapeutic drug by coupling with toxins or RI.

EXAMPLES

Next, although the following provides a specific explanation of the present invention through its Examples, the scope of the present invention is not limited by these Examples.

Example 1

Cloning of DNA Coding for the V Region of Mouse Monoclonal Antibody to Human Medulloblastoma Cells DNA coding for a variable region of mouse monoclonal antibody ONS-M21 to human medulloblastoma cells was cloned in the following manner.

1. Preparation of Messenger RNA (mRNA)

mRNA from hybridoma ONS-M21 was prepared using the Fast Track MRNA Isolation Kit Version 3.2 (Invitrogen).

2. Synthesis of Double-Stranded cDNA

Double-stranded cDNA was synthesized using The Copy Kit (Invitrogen) from approximately 4 μq of mRNA.

3. Amplification of Gene Coding for Antibody Variable Region by PCR

PCR was performed using Thermal Cycler (Perkin Elmer Cetus).

(1) Amplification of Gene Coding for Mouse L Chain V Region

MKV (Mouse Kappa Variable) primers (Jones, S. T. et al., Bio/Technology, 9, 88–89 (1991)) shown in SEQ ID NOS: 1 to 11, which hybridize with mouse kappa type L chain leader sequence, were used for the primers used in PCR.

100 μl of PCR solution contained 10 mM Tris-HCl (pH 8.3), 50 mM KCl, 0.1 mM dNTPs (DATP, dGTP, dCTP, dTTP), 1.5 mM MgCl$_2$, 5 units of DNA polymerase Ampli Taq (Perkin Elmer Cetus), 0.1 μM of MKV primer shown in SEQ ID NOS: 1 to 11, 0.4 μM of MKC primer shown in SEQ ID NO: 12 and 0.1 μg of double-stranded cDNA, and each of MCK primers 1 to 12 was separately amplified. After covering with 50 μl of mineral oil, the reaction mixture was heated at an initial temperature of 94° C. for 3 minutes and then in the order of 94° C. for 1 minute, 50° C. for 1 minute and 72° C. for 1 minute. After repeating this temperature cycle 30 times, the reaction mixture was further incubated for 10 minutes at 72° C.

(2) Amplification of cDNA Coding for Mouse H Chain V Region

MHV (Mouse Heavy Variable) primers 1 to 12 shown in SEQ ID NOS: 13 to 24 and MHC-GI (Mouse Heavy Constant) primer (Jones, S. T. et al., Bio/Technology, 9, 88–89 (1991)) shown in SEQ ID NO: 25 were used for the primers for PCR.

Amplification of cDNA was performed according to the same method as that described for amplification of L chain V region gene in the above-mentioned section 3(1) with the exception of performing amplification using a mixture of 0.25 μM of each MHV primer and 2.5 μM of MHC-GI primer.

4. Purification and Cleavage of PCR Products

DNA fragments amplified by PCR as described above were purified with low melting temperature agarose (Sigma), and digested for 3 hours at 37° C. using 5 units of restriction enzyme XmaI (New England Biolabs) in 10 mM Tris-HCl (pH 7.9) containing 10 MM MgCl$_2$ and 1 mM dithreitol.

Next, after digesting for 2 hours at 37° C. with 40 units of restriction enzyme SalI (Takara Shuzo), the resulting DNA fragments were separated by agarose gel electrophoresis using 1.5% low melting temperature agarose (Sigma).

A piece of agarose containing a DNA fragment of approximately 450 bp in length was cut out, melted for 5 minutes at 65° C. followed by the addition of an equal volume of 20 mM Tris-HCl (pH 7.5) containing 2 mM EDTA and 200 mM NaCl. This mixture was extracted with phenol and chloroform, the DNA fragments were recovered by ethanol precipitation and then dissolved in 10 mM Tris-HCl (pH 7.5) containing 1 mM EDTA.

Thus, a DNA fragment comprising a gene coding for a mouse kappa type L chain variable region, and a DNA fragment comprising a gene coding for a mouse H chain variable region were obtained. The above-mentioned DNA fragments have a SalI-cohesive end on their 5'-terminal, and an XmaI-cohesive end on their 3'-terminal.

5. Linkage and Transformation

Approximately 0.3 μg of SalI-XmaI DNA fragments comprising a gene coding for a mouse kappa type L chain V region prepared in the above manner were linked with approximately 0.1 μg of pUC19 vector prepared by digesting with SalI and XmaI, by reacting for 4 hours at 16° C. in a reaction mixture containing 50 mM Tris-HCl (pH 7.6), 10 MM MgCl$_2$, 10 mM dithiothreitol, 1 mM ATP, 50 mg/ml of polyethylene glycol (8000) and 1 unit of T4 DNA ligase (Gibco BRL).

Next, 10 μl of the above-mentioned linking mixture was added to 50 μl of E. coli DH5u competent cells after which the cells were allowed to stand undisturbed for 30 minutes on ice, 1 minute at 42° C. and again for 1 minute on ice.

Next, 400 μl of 2xYT medium (Molecular Cloning: A Laboratory Manual, Sambrooks et al., Cold Spring Harbor Laboratory Press, 1989) was added, and after incubating for 1 hour at 37° C., 2xYT agar medium (Molecular Cloning: A Laboratory Manual, Sambrooks et al., Cold Spring Harbor Laboratory Press, 1989) was inoculated with the E. coli and incubated overnight at 37° C. to obtain E. coli transformants.

These transformants were cultured overnight at 37° C. in 10 ml of 2xYT medium containing 50 μg/ml of ampicillin, and plasmid DNA was prepared from the culture according to the alkaline method (Molecular Cloning: A Laboratory Manual, Sambrooks, et al., Cold Spring Harbor Laboratory Press, 1989).

A plasmid containing a gene coding for a mouse kappa type L chain V region derived from hybridoma ONS-M21 obtained in this manner was named pUC-M21-V$_L$.

A plasmid containing a gene coding for a mouse H chain V region derived from hybridoma ONS-M21 was made from SalI-XmaI DNA fragments in accordance with the same method as that described above, and that plasmid was named pUC-M21-V$_H$.

Example 2

Determination of DNA Nucleotide Sequence

A nucleotide sequence of a cDNA coding region in the above-mentioned plasmid was determined in accordance with the protocol specified by the manufacturer using an automated DNA sequencer (Applied Biosystem Inc.) and the Taq Dye Deoxy Terminator Cycle Sequencing Kit (Applied Biosystem Inc.).

A nucleotide sequence of a gene coding for an L chain V region of mouse ONS-M21 antibody contained in plasmid pUC-M$^{21}$-V$_L$ is shown in SEQ ID NO: 26. In addition, a nucleotide sequence of a gene coding for the H chain V region of mouse ONS-M21 antibody contained in plasmid pUC-M21-V$_H$ is shown in SEQ ID NO: 28.

Example 3

Determination of CDR

The overall structures of the V regions of the L and H chains mutually resemble each other, and 4 framework regions are linked by 3 hypervariable regions, namely complementarity determining regions (CDRs). Although the amino acid sequence of the framework is relatively well preserved, the variability of the amino acid sequence of the CDRs is extremely high (Kabat, E. A. et al., "Sequences of Proteins of Immunological Interest", US Dept. of Health and Human Services, 1983).

On the basis of these facts, the CDRs were determined as shown in Table 4 as a result of investigating homology by applying the amino acid sequence of the variable region of mouse monoclonal antibody to human medulloblastoma cells to the database of antibody amino acid sequences prepared by Kabat, et al.

TABLE 4

| Plasmid | SEQ ID NO | CDR(1) | CDR(2) | CDR(3) |
|---|---|---|---|---|
| pUC-M21-V$_L$ | 26 | 24–34 | 50–56 | 89–97 |
| pUC-M21-V$_H$ | 28 | 31–35 | 50–66 | 99–106 |

Example 4

Confirmation of Expression of Cloned cDNA (Preparation of Chimeric ONS-M21 Antibody) Preparation of Expression Vector In order to make vectors that express chimeric ONS-M21 antibody, cDNA clone pUC-M21-$V_L$ and pUC-M21-$V_H$ that respectively code for the V regions of mouse ONS-M21κ L chain and H chain were modified by PCR. They were then introduced into HEF expression vectors (see, the previously mentioned WO92-19759) (see, FIG. 1).

Backward primer ONS-L722S (SEQ ID NO: 30) for the L chain V region and backward primer ONS-H3.2S (SEQ ID NO: 31) for the H chain V region were designed to hybridize with DNA coding for the start portion of the leader sequences of each V region and to have the Kozak consensus sequence (Kozak, M. et al., J. Mol. Biol., 196, 947–950, 1987) and an HindIII restriction site. Forward primer ONS-L722A (SEQ ID NO: 32) for the L chain V region and forward primer ONS-H3.2A (SEQ ID NO: 33) for the H chain V region were designed to hybridize with DNA coding for the end portion of the J region and to have a splice donor sequence and BamHI restriction site.

100 µl of PCR reaction mixture containing 10 mM Tris-HCl (pH 8.3), 50 mM KCl, 100 µM dNTPs, 1.5 TrM $MgCl_2$, 100 pmoles of each primer, 100 ng of template DNA (pUC-M21-$V_L$ or pUC-M21-$V_H$) and 5 units of Ampli Taq were covered with 50 µl of mineral oil. Following initial denaturation at 94° C., an incubation cycle consisting of 1 minute at 94° C., 1 minute at 55° C. and 1 minute at 72° C. was repeated 30 times followed by final incubation for 10 minutes at 72° C.

The PCR products were purified using 5% low melting temperature agarose gel, digested with HindIII and BamHI, and the L chain V region was cloned into HEF expression vector HEF-$V_L$-gκ, while the H chain V region was cloned into HEF expression vector HEF-$V_H$-gκ. After determining the DNA sequences, plasmids containing DNA fragments having the correct DNA sequence were respectively named HEF-M21L-gκ and HEF-M21H-gγ1.

Transfection into COS Cells

In order to observe the transient expression of chimeric ONS-M21 antibody, the above-mentioned expression vectors were tested in COS cells. HEF-M21L-gκ and HEF-M21H-gγ1 were co-transfected into COS cells by electroporation using a Gene Pulser apparatus (BioRad). Each DNA (10 µg) was added to an 0.8 ml aliquot of $1 \times 10^7$ cells/ml in PBS followed by the application of pulses at 1,900 V and capacitance of 25 µF.

After allowing a recovery period of 10 minutes at room temperature, the electroporated cells were added to DMEM culture medium containing 10% γ-globulin-free fetal calf serum (Gibco). After incubating for 72 hours, the culture supernatant was collected, cell debris was removed by centrifugation, and the supernatant was applied to a Protein A agarose column equilibrated with 5 volumes of binding buffer (Affi-Gel Protein A MAPSII Kit, BioRad). After washing the column with 15 volumes of binding buffer, it was eluted with 5 volumes of elution buffer. The eluate was concentrated and the buffer was changed to PBS using a microconcentrator (Centricon 100, Amicon).

Cell-ELISA

A Cell-ELISA plate for measuring antigen binding was prepared in the following manner. Human medulloblastoma cell line ONS-76 (Tamura, et al., Cancer Res., 49, 5380–5384 (1989)) prepared to $1 \times 10^6$ cells/ml with RPMI buffer containing 10% fetal calf serum was added to a 96-well plate. After culturing overnight, the cells were fixed with 0.1% glutaraldehyde (Nagai Chemical and Pharmaceuticals). After blocking, chimeric ONS-M21 antibody was serially diluted and added to each well. After incubating at room temperature and washing, alkaline phosphatase-bound goat anti-human IgG antibody (Sigma) was added. After additional incubation and washing, substrate solution was added followed by measurement of absorbance at 405 nm.

Figure 2:
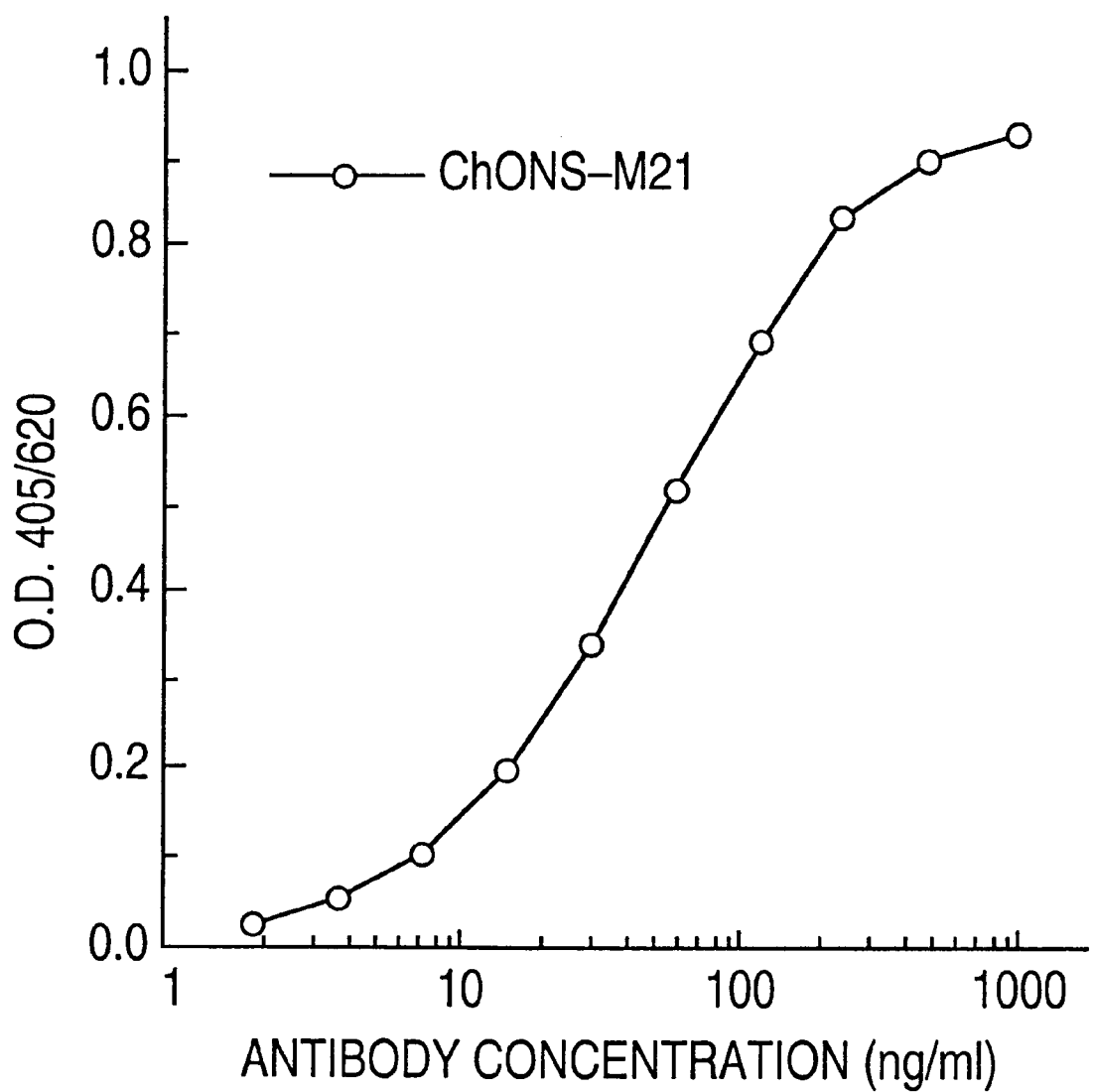
FIG. 2 is a graph indicating the binding ability of chimeric antibody ONS-M21 (ChM21) to human medulloblastoma cell line ONS-76.

As a result, it was suggested that chimeric antibody ONS-M21 has the correct structure of the V region of mouse monoclonal antibody ONS-M21 since it specifically bound with medulloblastoma cell line ONS-76 (see, FIG. 2).

Example 5

Preparation of Reshaped Human ONS-M21 Antibody

Preparation of Reshaped Human ONS-M21 Antibody L Chain V Region

Figure 3:
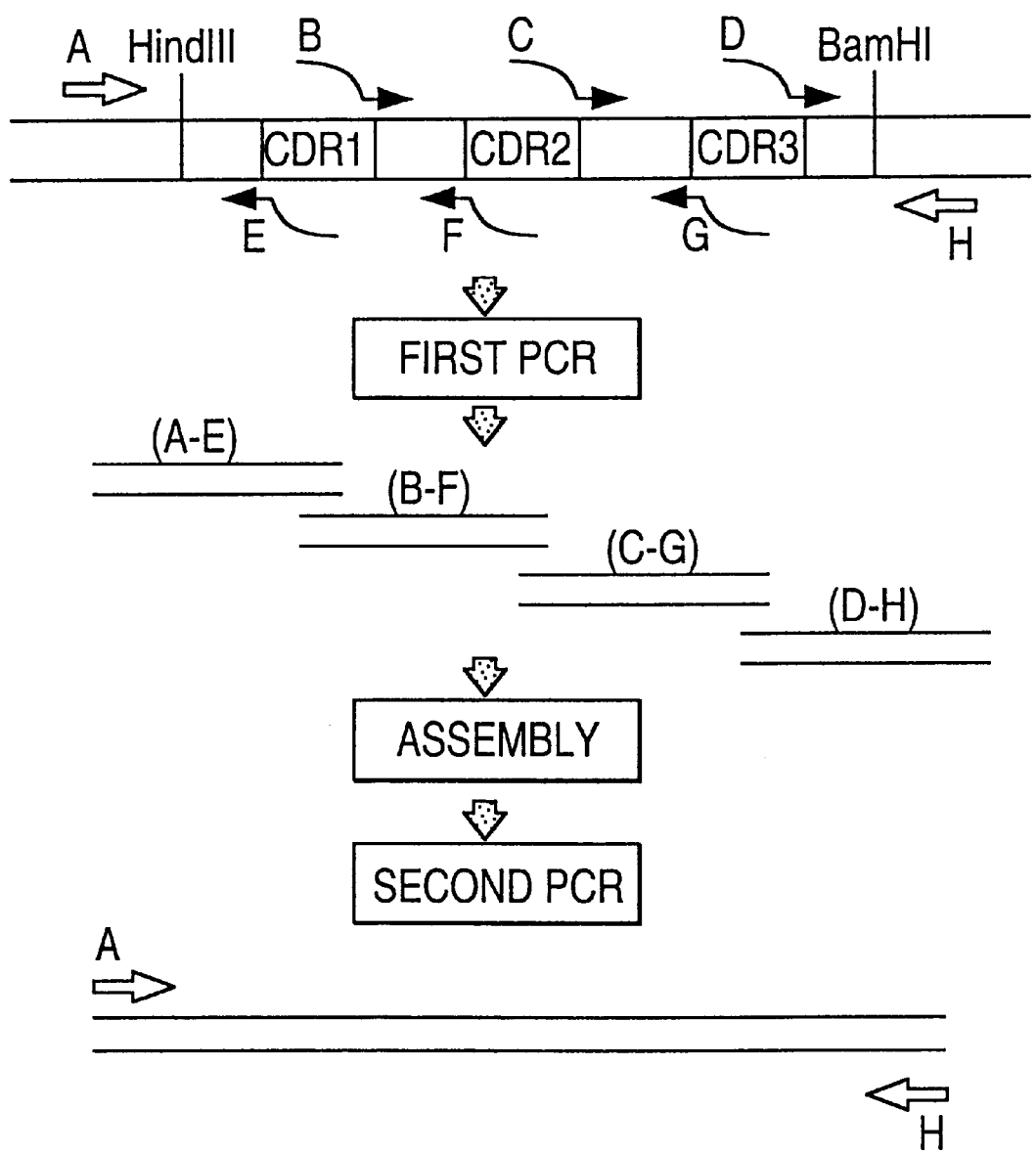
FIG. 3 is a diagram of the preparation of the first. version (Version "a") of the L chain V region of reshaped human antibody ONS-M21.

An L chain of a reshaped human ONS-M21 antibody was prepared by CDR-grafting using PCR. This technique is schematically illustrated in FIG. 3. In order to prepare a reshaped human antibody ONS-M21 having FRs derived from human antibody REI (version "a"), 8 PCR primers were used. External primers A (SEQ ID NO: 34) and H (SEQ ID NO: 35) were designed so as to hybridize with the DNA sequence of HEF expression vector HEF-$V_L$-gk.

CDR-grafting primers B (SEQ ID NO: 36), C (SEQ ID NO: 37) and D (SEQ ID NO: 38) have sense DNA sequences, while CDR-grafting primers E (SEQ ID NO: 39), F (SEQ ID NO: 40) and G (SEQ ID NO: 41) have anti-sense DNA sequences, and have complementary DNA sequences (23–35 bp) to the DNA sequences of the 5'-terminals of primers B, C and D, respectively.

In the first stage of PCR, the four reactions between A-E, B-F, C-G and D-H were performed, and each PCR product was purified. The four PCR products from the first stage of PCR were assembled according to their own complementarity (see, WO92-19759). Next, external primers A and H were added to amplify the entire DNA coding for an L chain V region of a reshaped human ONS-M21 antibody (second stage of PCR). In the above-mentioned PCR, plasmid HEF-$RV_L$-SK2a coding for version "a" of the L chain V region of reshaped human SK2 antibody based on the FRs from human antibody REI (see, Japanese Unexamined Patent Publication No. 5-129787) was used as a template.

In the first stage of PCR, 100 µl of PCR mixture containing 50 mM KCl, 100 µM dNTPs, 1.5 mM $MgCl_2$, 100 ng of template DNA, 100 pmoles of each primer and 5 units of Ampli Taq were used. Each PCR tube was covered with 50 µl of mineral oil. After initially denaturing at 94° C., a reaction cycle was performed consisting of 1 minute at 94° C., 1 minute at 55° C. and 1 minute at 72° C. followed finally by incubation for 10 minutes at 72° C.

PCR products A-E (218 bp), B-F (101 bp), C-G (131 bp) and D-H (147 bp) were purified using 1.5% low melting temperature agarose gel, and assembled in the second stage of PCR. In the second stage of PCR, 98 µl of PCR mixture containing 1 µg of each first stage PCR product and 5 units of Ampli Taq were incubated in a cycle consisting of 2 minutes at 94° C., 2 minutes at 55° C. and 2 minutes at 72° C. after which 100 pmoles of each external primers (A and H) were added. The PCR tube was covered with 50 µl of mineral oil and 30 cycles of PCR were performed under the same conditions as described above.

The 516 bp DNA fragment produced from the second stage of PCR was purified with 1.5% low melting temperature agarose gel, digested with BamHI and HindIII, and the resulting DNA fragment was cloned into HEF expression vector HEF-$V_L$-gk. After determining the DNA sequence, the plasmid containing the DNA fragment coding for the correct amino acid sequence of the L chain V region of a reshaped human ONS-M21 antibody was named HEF-RVL-M21a-gκ. The amino acid sequence and nucleotide sequence of the L chain V region contained in this plasmid HEF-RVL-M21a-gκ are shown in SEQ ID NO: 43.

Version "b" of the L chain V region of reshaped human ONS-M21 antibody was prepared by PCR mutagenesis. Mutagenic primers FTY-1 (SEQ ID NO: 44) and FTY-2 (SEQ ID NO: 45) were designed so that the phenylalanine at position 71 is substituted to tyrosine.

After amplification using the above-mentioned primers and plasmid HEF-RVL-M21a-gκ as a template, the final product was purified, digested with BamHI and HindIII, and the resulting DNA fragment was cloned into HEF expression vector HEF-VL-gκ to obtain plasmid HEF-RVL-M 21b-gκ. The amino acid sequence and nucleotide sequence of the L chain V region contained in this plasmid HEF-RVL-M21b-gκ are shown in SEQ ID NO: 43.

Each of versions "c", "d", "e", "f", "g", "h", "i", "j", "k", "l", "m", "n", "o" and "p" of the L chain V region of reshaped human ONS-M21 antibody was produced in the manner described below.

For version "c", amplification was performed by PCR using primers M21M2S (SEQ ID NO: 48) and M21M2A (SEQ ID NO: 49), which were designed so that tyrosine at position 87 is substituted to phenylalanine, as mutagenic primers, and using plasmid HEF-RVL-M21a-gκ as a template DNA to obtain plasmid HEF-RVL-M21c-gκ. The amino acid sequence and nucleotide sequence of the L chain V region contained in this plasmid HEF-RVL-M21c-gκ are shown in SEQ ID NOS: 50 and 51.

For version "d", amplification was performed using primers FTY-1 and FTY-2 as well as M21M2S and M21M2A as mutagenic primers, and using plasmid HEF-RVL-M21a-gκ as a template DNA to obtain plasmid HEF-RVL-M21d-gκ. The amino acid sequence and nucleotide sequence of the L chain V region contained in this plasmid HEF-RVL-M21d-gκ are shown in SEQ ID NOS: 52 and 53.

For version "e", amplification was performed using primers M21M3S (SEQ ID NO: 54) and M21M3A (SEQ ID NO: 55), which were designed so that threonine at position 20 is substituted to serine and isoleucine at position 21 is substituted to valine, as mutagenic primers, and using plasmid HEF-RVL-M21a-gκ as a template DNA to obtain plasmid HEF-RVL-M21e-gκ. The amino acid sequence and nucleotide sequence of the L chain V region contained in this plasmid HEF-RVL-M21e-gκ are shown in SEQ ID NOS: 56 and 57.

For version "f", plasmid HEF-RVL-M21c-gκ was digested with BamrHI and HinfI, and plasmid HEF-RVL-M21e-gκ was digested with HindIII and HinfI to obtain 152 bp and 250 bp DNA fragments respectively. After isolating and purifying these DNA fragments using 15% low melting temperature agarose gel, the fragments were linked and inserted into HEF expression vector HEF-RVL-gκ to obtain plasmid HEF-RVL-M21f-gκ. The amino acid sequence and nucleotide sequence of the L chain V region contained in this plasmid HEF-RVL-M21f-gκ are shown in SEQ ID NOS: 58 and 59.

For version "g", amplification was performed using primers M21M4S (SEQ ID NO: 60) and M21M4A (SEQ ID NO: 61), which were designed so that phenylalanine at position 73 is substituted to leucine, as mutagenic primers, and using plasmid HEF-RVL-M21f-gκ as a template DNA to obtain plasmid HEF-RVL-M21g-gκ. The amino acid sequence and nucleotide sequence of the L chain V region contained in this plasmid HEF-RVL-M21g-gκ are shown in SEQ ID NOS: 62 and 63.

For version "h", amplification was performed using primers M21M4S and M21M4A as mutagenic primers, and using plasmid HEF-RVL-M21a-gκ as a template DNA to obtain plasmid HEF-RVL-M21h-gκ. The amino acid sequence and nucleotide sequence of the L chain V region contained in this plasmid HEF-RVL-M21h-gκ are shown in SEQ ID NOS: 64 and 65.

For version "i", amplification was performed using primers M21M5S (SEQ ID NO: 66) and M21M5A (SEQ ID NO: 67), which were designed so that lysine at position 42 is substituted to glutamine, analine at position 43 is substituted to serine and leucine at position 46 is substituted to proline, as mutagenic primers, and using plasmid HEF-RVL-M21g-gκ as a template DNA to obtain plasmid HEF-RVL-M21i-gκ. The amino acid sequence and nucleotide sequence of the L chain V region contained in this plasmid HEF-RVL-M21i-gκ are shown in SEQ ID NOS: 68 and 69.

For version "j", amplification was performed using primers M21M5S, M21M5A as well as M21M6S (SEQ ID NO: 70) and M21M6A (SEQ ID NO: 71), which were designed so that threonine at position 85 is substituted to aspartate, as mutagenic primers, and using plasmid HEF-RVL-M21i-gκ as a template DNA to obtain plasmid HEF-RVL-M21j-gκ. The amino acid sequence and nucleotide sequence of the L chain V region contained in this plasmid HEF-RVL-M21j-gκ are shown in SEQ ID NOS: 72 and 73.

For version "k", amplification was performed using primers M21M6S and M21M6A as mutagenic primers, and using plasmid HEF-RVL-M21g-gκ as a template DNA to obtain plasmid HEF-RVL-M21k-gκ. The amino acid sequence and nucleotide sequence of the L chain V region contained in this plasmid HEF-RVL-M21k-gκ are shown in SEQ ID NOS: 74 and 75.

For version "l", plasmid HEF-RVL-M21a-gκ was digested with BamHI and SfaNI, and plasmid HEF-RVL-M21i-gκ was digested with HindIII and SfaNI to obtain 227 bp and 169 bp DNA fragments respectively. After isolating and purifying these DNA fragments, the resulting DNA fragments were linked and inserted into HEF expression vector HEF-RVL-gκ to obtain plasmid HEF-RVL-M21l-gκ. The amino acid sequence and nucleotide sequence of the L chain V region contained in this plasmid HEF-RVL-M21l-gκ are shown in SEQ ID NOS: 76 and 77.

For version "m", amplification was performed using primers M21M5S, M21M5A as well as M21M7S (SEQ ID NO: 78) and M21M7A (SEQ ID NO: 79), which were designed so that proline at position 8 is substituted to glutamate, serine at position 9 is substituted to lysine and serine at position 10 is substituted to phenylalanine, as mutagenic primers, and using plasmid HEF-RVL-M21a-gκ as a template DNA to obtain plasmid HEF-RVL-M21m-gκ. The amino acid sequence and nucleotide sequence of the L chain V region contained in this plasmid HEF-RVL-M21m-gκ are shown in SEQ ID NOS: 80 and 81.

For version "n", amplification was performed using primers M21M8S (SEQ ID NO: 82) and M21M8A (SEQ ID NO: 83), which were designed so that lysine at position 42 is substituted to glutamate and alanine at position 43 is substituted to serine, as mutagenic primers, and using plasmid HEF-RVL-M21a-gκ as a template DNA to obtain plasmid HEF-RVL-M21n-gκ. The amino acid sequence and nucleotide sequence of the L chain V region contained in this plasmid HEF-RVL-M21n-gκ are shown in SEQ ID NOS: 84 and 85.

For version "o", plasmid HEF-RVL-M21b-gκ was digested with BamHI and BsrI, and plasmid HEF-RVL-M21a-gκ was digested with HindIII and BsrI to obtain 251 bp and 142 bp DNA fragments respectively. After isolating and purifying these DNA fragments, the resulting DNA fragments were linked and inserted into HEF expression vector HEF-RVL-gκ to obtain plasmid HEF-RVL-M21o-gκ. The amino acid sequence and nucleotide sequence of the L chain V region contained in this plasmid HEF-RVL-M21o-gκ are shown in SEQ ID NOS: 86 and 87.

For version "p", amplification was performed using primers M21M9S (SEQ ID NO: 88) and M21M9A (SEQ ID NO: 89), which were designed so that leucine at position 46 is substituted to proline, as mutagenic primers, and using plasmid HEF-RVL-M21a-gκ as a template DNA to obtain plasmid HEF-RVL-M21p-gκ. The amino acid sequence and nucleotide sequence of the L chain V region contained in this plasmid HEF-RVL-M21p-gκ are shown in SEQ ID NOS: 90 and 91.

Preparation of Reshaped Human ONS-M21 Antibody H Chain V Region

DNA coding for the H chain V region of reshaped human ONS-M21 antibody was designed in the following manner. DNA sequences coding for FR1-3 of human antibody Eu and FR4 of human antibody ND were designed based on "codon usage" of the V region (Kabat, E. A. et al., US Dept. of Health and Human Services, US Government Printing Offices, 1991). By connecting with a DNA sequence coding for the CDRs of the H chain V region of mouse ONS-M21 antibody, an entire length of DNA was designed coding for the H chain V region of reshaped human ONS-M21 antibody.

Next, a HindIII recognition site/KOZAK consensus sequence and BamHI recognition site/splice donor sequence were added to this 5'-terminal and 3'-terminal, respectively, of this DNA sequence to enable inserted into an HEF expression vector.

The DNA sequence designed in this manner was then divided into four oligonucleotides, and the secondary structures of oligonucleotides having the potential to inhibit assembly of these oligonucleotides were analyzed by computer.

Figure 4:
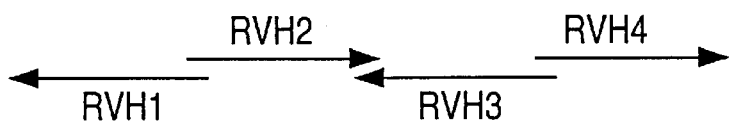
FIG. 4 is a diagram of the preparation of the H chain V region of reshaped human antibody ONS-M21.

The four oligonucleotide sequences are shown in SEQ ID NOS: 92 to 95. These oligonucleotides have lengths of 111 to 137 bases, and possess overlapping regions of 23 to 26 bp. Among the oligonucleotides, the RVH2 (SEQ ID NO: 92) and RVH4 (SEQ ID NO: 93) have sense DNA sequences, while the other RVHI (SEQ ID NO: 94) and RVH3 (SEQ ID NO: 95) have anti-sense DNA sequences. The assembly method of these four oligonucleotides by PCR is shown in the illustration (see, FIG. 4).

After initially denaturing 98 μl of PCR mixture containing 100 ng of each of the four types of oligonucleotides and 5 units of Ampli Taq for 2 minutes at 94° C., the mixture was incubated for 2 cycles consisting of 2 minutes at 94° C., 2 minutes at 55° C. and 2 minutes at 72° C. After adding 100 pmoles each of RHP1 (SEQ ID NO: 96) and RHP2 (SEQ ID NO: 97) as external primers, the PCR tube was covered with 50 yl of mineral oil, and after initially denaturing for 1 minute at 94° C., 38 cycles of incubation consisting of 1 minute at 94° C., 1 minute at 55° C. and 1 minute at 72° C. were performed followed by final incubation for 10 minutes at 72° C.

The 438 bp DNA fragment was purified using 1.5% low melting temperature agarose gel, digested with HindIII and BamHI, and cloned in HEF expression vector HEF-$V_H$-gγ1.

After determining the DNA sequence, the plasmid containing the DNA fragment coding for the correct amino acid sequence of the H chain V region was named HEF-RVH-M21-gγ1. The amino acid sequence and nucleotide sequence of the H chain V region contained in this plasmid HEF-RVH-M21-gγ1 are shown in SEQ ID NOS: 98 and 99.

In order to evaluate each chain of reshaped human ONS-M21 antibody, COS cells were co-transfected as previously described with expression vector HEF-RVH-M21-gγ1 for the H chain of reshaped human ONS-M21 antibody, and expression vector HEF-M21L-gγ1 for the L chain of chimeric ONS-M21 antibody. After collecting the antibody products as previously described, antigen binding was measured as previously described.

Figure 5:
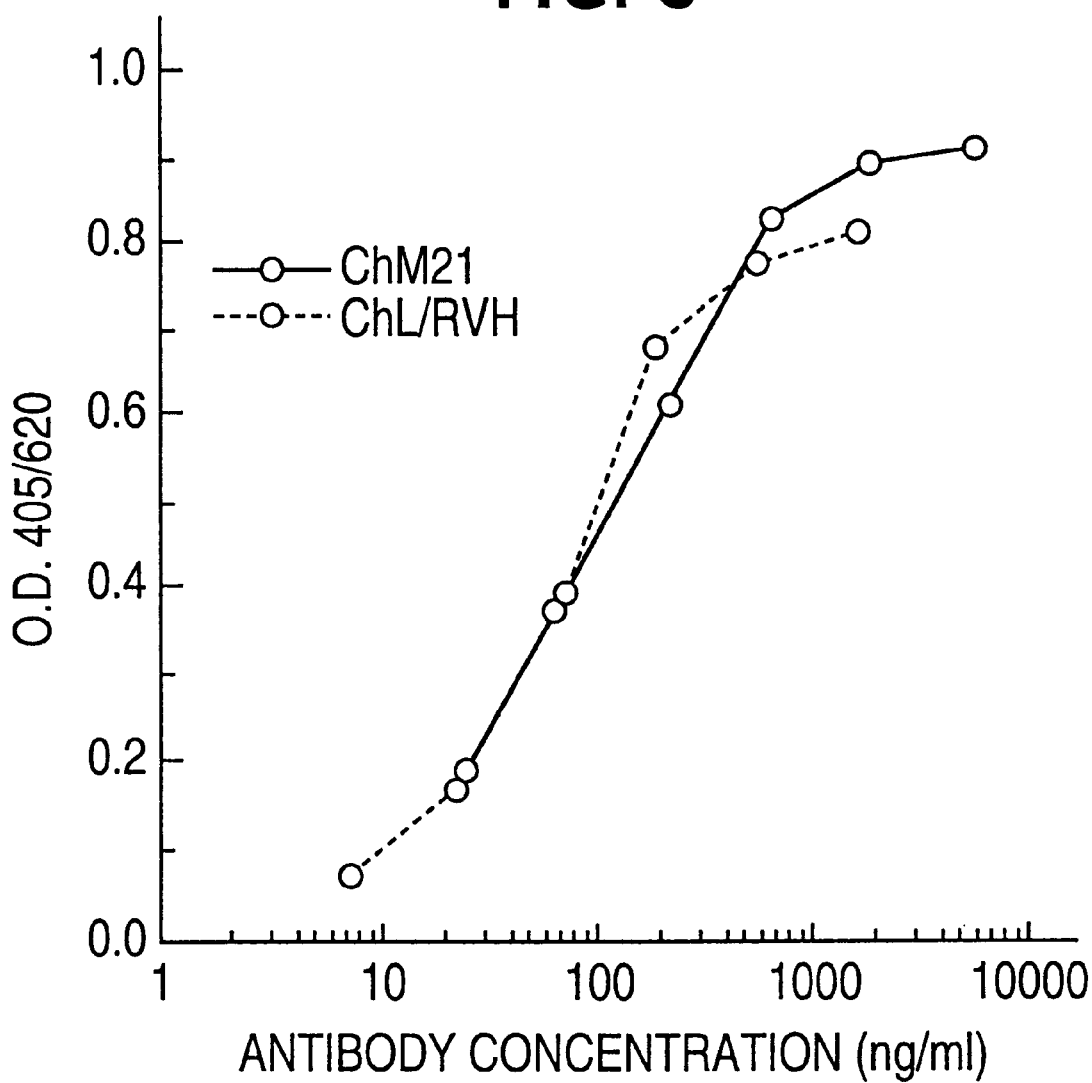
FIG. 5 is a graph indicating the binding ability of antibody comprising reshaped human H chain and chimeric L chain to human medulloblastoma cell line ONS-76.

Those results are shown in FIG. 5. As shown in FIG. 5, there was confirmed to be no difference in antigen binding between chimeric antibody (ChM21) used as positive control and antibody comprising reshaped H chain and chimeric L chain (ChL/RVH).

Figure 6:
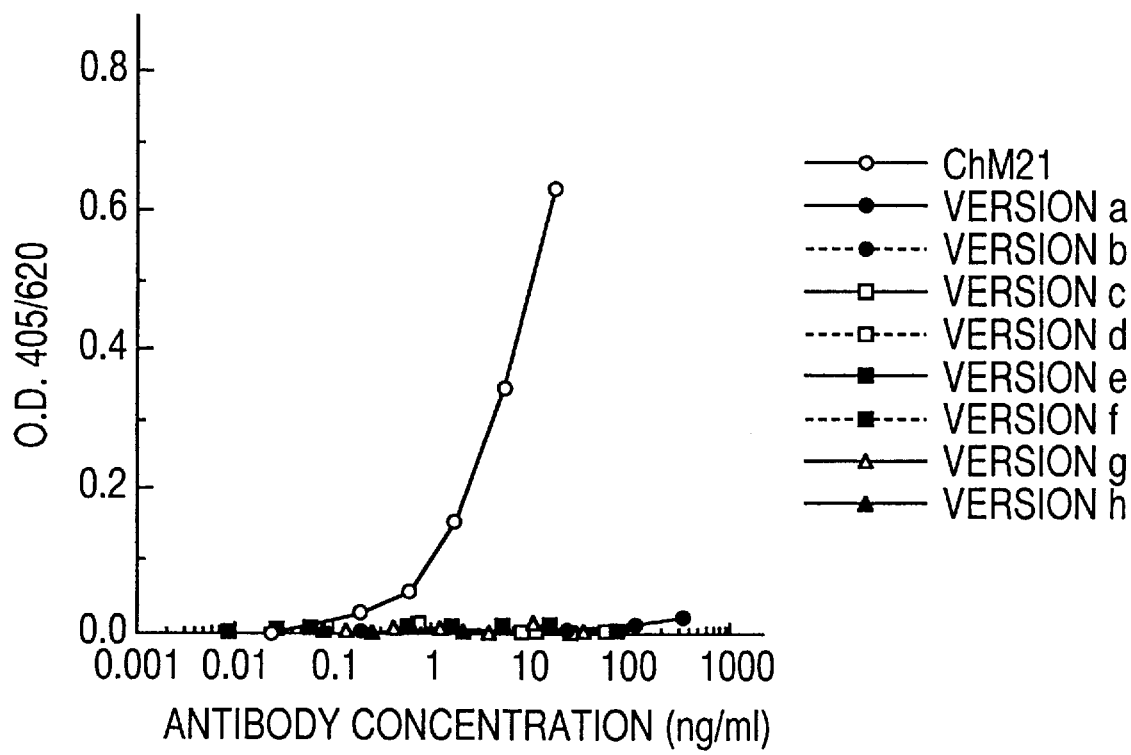
FIG. 6 is a graph comparing the binding ability of 8 types of reshaped human ONS-M21 antibodies comprising reshaped human H chain and one of versions "a" through "h" of reshaped human L chain, to human medulloblastoma cell line ONS-76, with that of chimeric antibody (ChM21).

Next, in order to evaluate combinations of each of versions "a" through "p" of reshaped humanized ONS-M21 antibody L chain and reshaped humanized ONS-M21 antibody H chain, one of each of the expression plasmids from HEF-RVL-M21a-gκ to HEF-RVH-M21p-gκ of each version of the L chain and H chain expression plasmid HEF-RVH were co-transfected into COS cells and antigen binding was measured for the resulting antibodies using the method as described in Cell ELISA of the above-mentioned Embodiment 4. As a result, antigen binding activity was not observed in antibodies having L chain versions "a" through "h" (see, FIG. 6).

Figure 7:
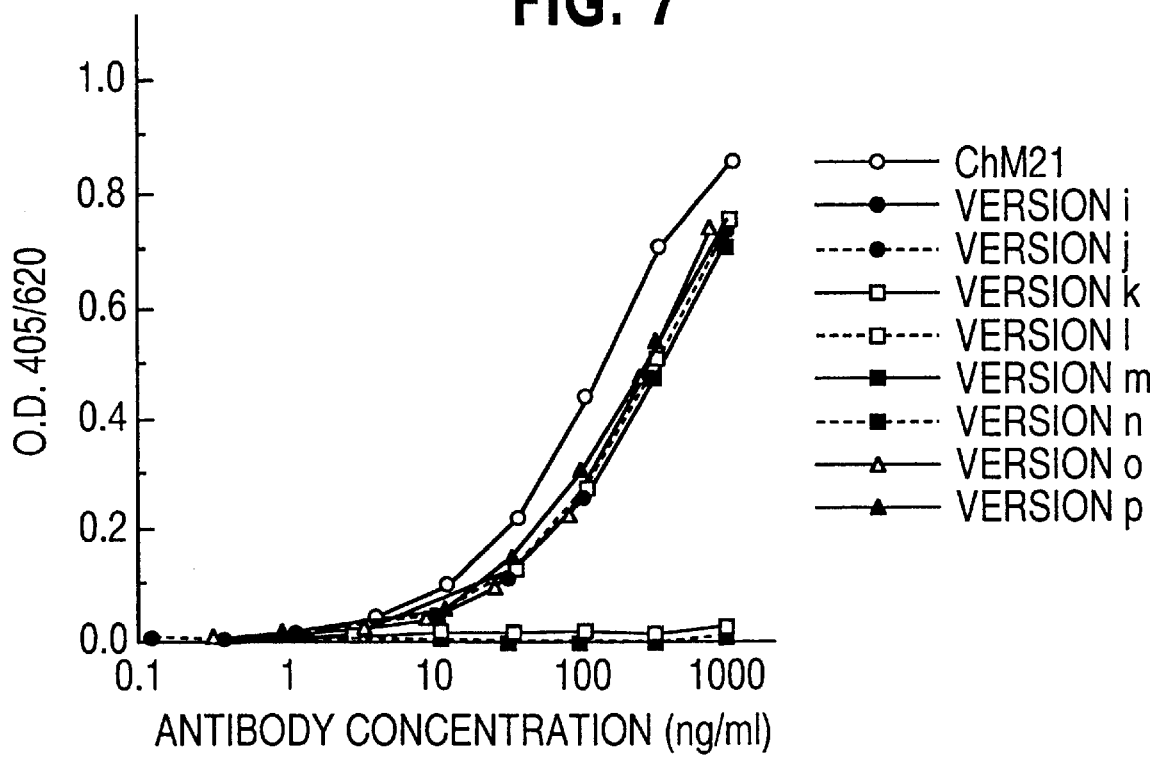
FIG. 7 is a graph comparing the binding ability of 6 types of reshaped human ONS-M21 antibodies comprising the reshaped human H chain and one of versions "i", "i", "l"), "m", "o" and "p" of reshaped human L chain of the present invention, to human medulloblastoma cell line ONS-76, with that of chimeric antibody (ChM21) and antibodies having reshaped L chain versions "k" and "n".

On the other hand, antibodies having each of the L chain versions "i", "j", "l", "m", "o" and "p" demonstrated good antigen binding comparable to that of the positive control chimeric ONS-M21 antibody (ChM21), and this combination was suggested to create a functional antigen binding site in human antibody. Furthermore, antigen binding activity was not observed in antibodies having L chain versions "k" and "n" (refer to FIG. 7).

On the basis of these findings, antibody having proline at position 46 of the L chain FR2 was suggested to recreate a functional antigen binding site that exhibits good antigen binding.

Example 6

Preparation of Reshaped Human ONS-M21 Antibody Single-Chain Fv (scFV) Construction of Linker Region DNA coding for a linker region consisting of Gly Gly Gly Gly Ser Gly Gly Gly Gly Ser Gly Gly Gly Gly Ser (SEQ ID NO: 111) was designed in the following manner. A 15 bp DNA sequence coding for 5 amino acid residues of the C-terminal of FR4 of the H chain V region was added to the 5'-terminal of a DNA sequence coding for a linker region (Huston, J. S. et al., Proc. Natl. Acad. Sci. USA, 85, 5879–5883 (1988)), while a 15 bp DNA sequence coding for 5 amino acid residues of the N-terminal of the FR1 region of the L chain V region was added to the 3'-terminal. Moreover, HindIII and EcoRI recognition sites were added to the 5'-terminal and 3'-terminal, respectively, to enable insertion into pUC19 vector.

Two oligonucleotides scFv-S and scFv-A in the sense and anti-sense directions were synthesized based on the DNA sequences designed in this manner.

The two oligonucleotide sequences are shown in SEQ ID NOS: 81 and 82, respectively. These oligonucleotides have a length of 84 bases, and have an overlapping region of 81 bp.

100 pmoles each of the two oligonucleotides were placed in 20 μl of a reaction mixture containing 50 mM Tris-HCl (pH 7.6), 10 mM MgCl$_2$, 10 mM dithiothreitol, 1 mM ATP and 50 mg/ml polyethylene glycol (8000). Annealing was performed by incubating for 5 minutes at 96° C., lowering the temperature to 65° C. over the course of 20 minutes, incubating for 10 minutes at 65° C., lowering the temperature to 37° C. over the course of 20 minutes, incubating for 10 minutes at 37° C., lowering the temperature to 7° C. over the course of 20 minutes and finally incubating at 7° C. overnight.

The DNA annealed in the above-mentioned manner was inserted into pUC19 vector cleaved with HindIII and EcoRI. After determining the DNA sequence, the plasmid containing the DNA fragment that has the correct DNA sequence was named pUC-scFv-5.

Preparation of Reshaped Human ONS-M21 Antibody Single-Chain Fv

Figure 8:
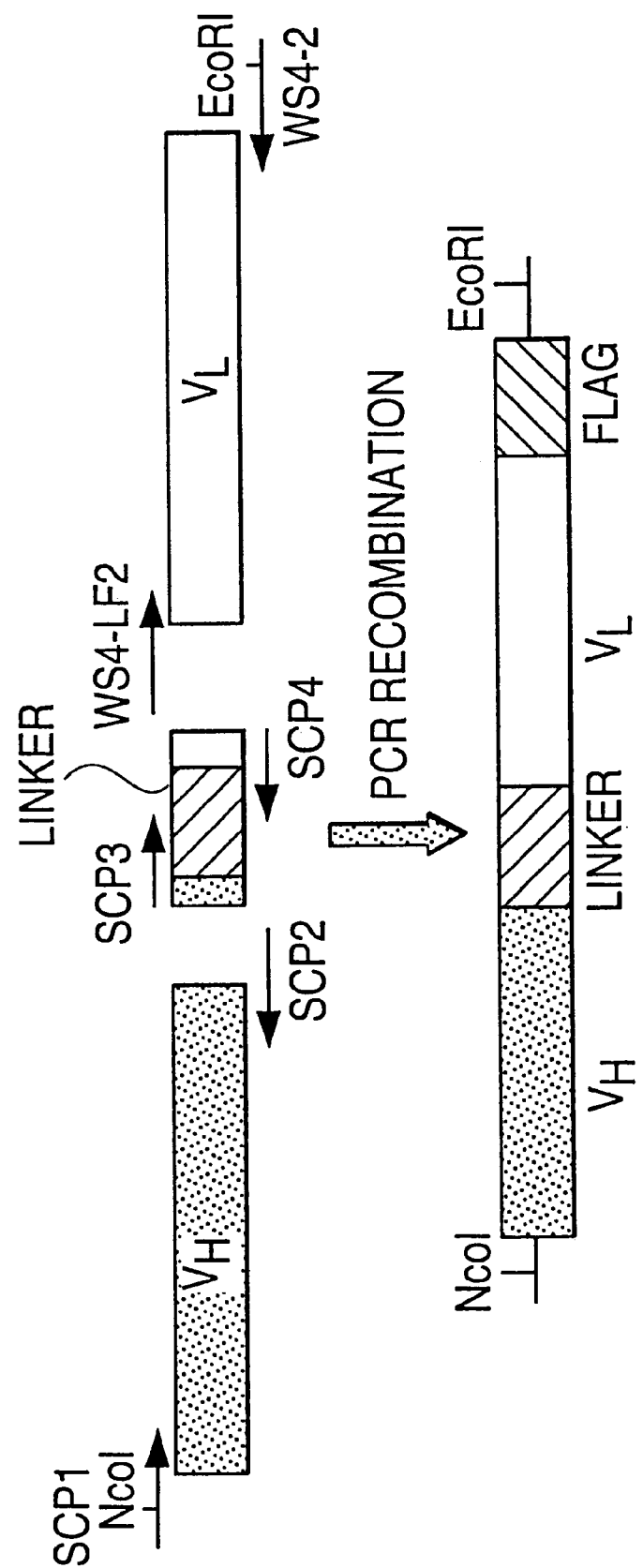
FIG. 8 is a schematic diagram of a preparation process of DNA coding for the single chain Fv region of the present invention.

The single-chain Fv of reshaped human ONS-M21 antibody was produced in the following manner. Reshaped human ONS-M21 antibody H chain V region, linker region and reshaped human ONS-M21 antibody L chain V region were respectively amplified and assembled using PCR to construct reshaped human ONS-M21 antibody single-chain Fv. This procedure is schematically illustrated in FIG. 8. Six PCR primers (A to F) were used to construct the single-chain Fv of reshaped human ONS-M21 antibody. Primers A, C and E have sense sequences, while primers B, D and F have anti-sense sequences.

Backward primer SCP1 (primer A, SEQ ID NO: 102) for the H chain V region was designed to hybridize with DNA coding for the N-terminal of the H chain V region and to have an NcoI recognition site. Forward primer SCP2 (primer B, SEQ ID NO: 103) for the H chain V region was designed to hybridize with DNA coding for the C-terminal of the H chain V region and to overlap with the linker. Backward primer SCP3 (primer C, SEQ ID NO: 104) for the linker region was designed to hybridize with DNA coding for the N-terminal of the linker and to overlap with DNA coding for the C-terminal of the H chain V region.

Forward primer SCP4 (primer D, SEQ ID NO: 105) for the linker region was designed to hybridize with DNA coding for the C-terminal of the linker and to overlap with DNA coding for the N-terminal of the L chain V region. Backward primer SCP4 (primer E, SEQ ID NO: 106) for the L chain V region was designed to hybridize with DNA coding for the C-terminal of the linker and to overlap with DNA coding for the N-terminal of the L chain V region. Forward primer WS4-2 (primer F, SEQ ID NO: 107) for the L chain V region was designed to hybridize with DNA coding for the C-terminal of the L chain V region and to have a sequence coding for the FLAG peptide (Hopp, T. P. et al., Bio/Technology, 6, 1204–1210, 1988), two transcription termination codons and an EcoRI recognition site.

In the first step of PCR, three reactions were conducted between A-B, C-D and E-F and each PCR product was purified. The three PCR products from the first step of PCR were assembled according to their own complementarity. Next, primers A and F were added to amplify the entire length of DNA coding for the single-chain Fv of reshaped human ONS-M21 antibody (second step of PCR). Furthermore, in the first step of PCR, plasmid HEF-RVH-M21-gγ1 coding for the H chain V region of reshaped human ONS-M21 antibody (refer to Embodiment 5), plasmid pUC-scFv-5 coding for the linker region, and plasmid HEF-RVL-M21p-gκ (refer to Embodiment 5) coding for version "p" of the L chain V region of reshaped human ONS-M21 antibody were respectively used as templates.

In the first step of PCR, a PCR mixture was used containing 10 mM Tris-HCl (pH 8.3), 50 mM KCl, 100 μM dNTPs, 1.5 mM MgCl$_2$, 100 ng of each template DNA, 100 pmoles of each primer and 5 units of DNA polymerase Ampli Taq (Perkin Elmer Cetus). After covering each PCR tube with 50 μl of mineral oil, the tube was heated in the order of 1 minute at 94° C., 1 minute at 55° C. and 1 minute at 72° C. After repeating this temperature cycle 30 times, the reaction mixture was additionally incubated for 10 minutes at 72° C.

PCR products A-B (382 bp), C-D (92 bp) and E-F (363 bp) were purified using 1.5% low melting temperature agarose gel and assembled in the second step of PCR. In the second step of PCR, 98 μl of PCR reaction mixture, containing 1 μg of each of the first stage PCR products as templates and 5 units of Ampli Taq, were incubated for 2 cycles consisting of 2 minutes at 94° C., 2 minutes at 55° C. and 2 minutes at 72° C. followed by addition of 100 pmoles each of primers A and F. After covering the PCR tube with 50 Al of mineral oil, 30 cycles of PCR were performed consisting of 1 minute at 94° C., 1 minute at 55° C. and 2 minutes at 72° C.

Figure 9:
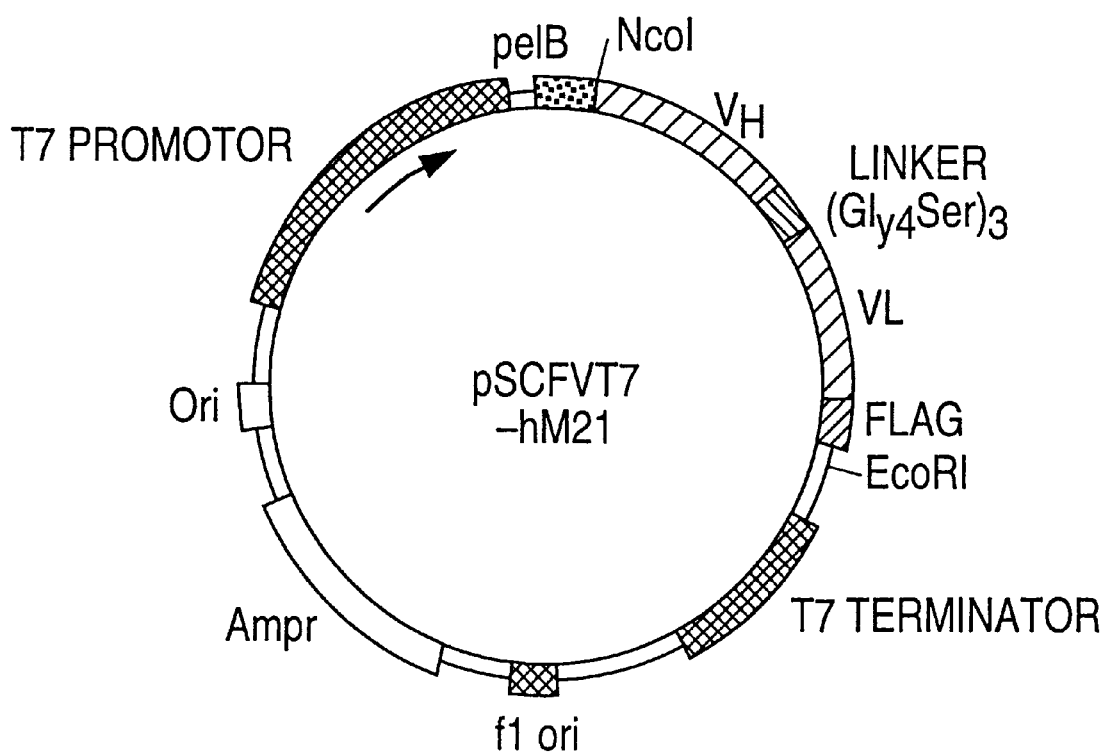
FIG. 9 indicates the structure of an example of expression plasmids used for expressing DNA coding for the single chain Fv region of the present invention.

The 767 bp DNA fragment produced in the second step of PCR was purified with 1.5% low melting temperature agarose gel and digested with NcoI and EcoRI, after which the resulting DNA fragments were cloned in expression vector pSCFVT7. Furthermore, this expression vector pSCFVT7 contains a pelB signal sequence suited to *E. coli* periplasm secretion expression systems (Lei, S. P. et al., J. Bacteriology, 169, 4379–4383, 1987). After determining the DNA sequence, the plasmid containing the DNA fragment coding for the correct amino acid sequence of the single-chain Fv of reshaped human ONS-M21 antibody was named pSCFVT7-hM21 (see FIG. 9). The amino acid sequence and nucleotide sequence of the single-chain Fv of reshaped human ONS-M21 antibody contained in this plasmid SCFVT7-hM21 are shown in SEQ ID NOS: 108 and 109.

Transformation of *E. coli* strain BL21(DE3)

10 ng of the above-mentioned plasmid pSCFVT7-hM21 was added to 50 μl of *E. coli* BL21(DE3) competent cells, after which the cells were allowed to stand for 30 minutes on ice, for 90 seconds at 42° C. and again for 1 minute on ice. Next, 400 μl of 2×YT medium was added and after incubating for 1 hour at 37° C., the *E. coli* was plated onto 2×YT agar medium and incubated overnight at 37° C. to obtain *E. coli* transformants.

Induction of Expression of Reshaped Human ONS-M21 Antibody Single-Chain Fv Region The transformed *E. coli* was cultured overnight at 37° C. in 30 ml of LB medium (Molecular Cloning: A Laboratory Manual, Sambrook, et al., Cold Spring Harbor Laboratory Press, 1989) containing 1% glucose and 50 μg/ml ampicillin. Next, the culture was innoculated into 100 times volume of LB medium containing 50 μg/ml ampicillin and cultured at 37° C. Isopropyl thio-β-D-galactoside (IPTG) was added to a final concentration of 0.5 mM when absorbance at 650 nm reached about 0.3 to induce expression from T7 promoter.

After additionally culturing overnight at 37° C., the medium was collected, cell debris was removed by centrifugation followed by the addition of an equal volume of PBS. After equilibrating with 15 ml of 0.1 M glycine-HCl (pH 3.0), the medium was applied to an anti-FLAG affinity column neutralized with an equal volume of PBS (Anti-FLAGM2 Affinity Gel, IBI). After washing the column with 3 volumes of PBS, the column was eluted with 6 ml of 0.1 M glycine-HCl (pH 3.0). The eluate was concentrated and the buffer was changed to PBS using a microconcentrator (Centricon10, Amicon).

Cell-ELISA

The antigen binding activity of the single-chain Fv of reshaped human ONS-M21 antibody was measured using for an indicator an inhibitory activity of mouse monoclonal ONS-M21 antibody on antigen binding. After blocking the Cell-ELISA plate prepared as described above, serially diluted samples of the reshaped human ONS-M21 antibody single-chain Fv, reshaped human ONS-M21 antibody or of Fab fragment prepared from the reshaped human ONS-M21 antibody were added together with mouse monoclonal ONS-M21 antibody at a concentration of 500 ng/ml to each well. After incubating at room temperature and washing, alkaline-phosphatase-bound goat anti-mouse IgG antibody (Zymed) was added. After incubating and washing, substrate solution was added followed by measurement of absorbance at 405 nm.

As a result, although inhibitory activity of the single-chain Fv of reshaped human ONS-M21 antibody (scFv-hM21) decreased to about 1/10 in comparison with reshaped human ONS-M21 antibody (hM21), it showed almost same inhibitory activity as the Fab fragment prepared from reshaped human ONS-M21 antibody (see, FIG. 10).

On the basis of these findings, single-chain Fv of a reshaped human ONS-M21 antibody was suggested to exhibit roughly the same degree of affinity as the original reshaped human ONS-M21 antibody.

Furthermore, $E.\ coli$ having the above-mentioned plasmid HEF-RVL-M21p-gκ and $E.\ coli$ containing plasmid HEF-RVH-M21-gγ1 are respectively deposited as $Escherichia\ coli$ DH5α (HEF-RVL-M21p-gκ) and $Escherichia\ coli$ DH5α (HEF-RVH-M21-gγ1) at the National Institute of Bioscience and Human Technology Agency of Industrial Science and Technology (1-3 Higashi, 1-chome Tsukuba-shi, Ibaraki), and were submitted for international deposit under the provisions of the Budapest Accord as FERM BP-4472 and FERM BP-4471 on Nov. 18, 1993.

Reference Example 1

Preparation of Hybridoma ONS-M21

Hybridoma that produces an anti-human medulloblastoma cell monoclonal antibody was prepared by fusing spleen cells of a BALB/c mouse immunized with human medulloblastoma cells ONS-76 and mouse myeloma cells P3U1 in accordance with routine methods using polyethylene glycol. Screening was performed using as an indicator a binding activity with medulloblastoma cells ONS-76 so as to establish hybridoma ONS-M21 (Moriuchi, S. et al., Br. J. Cancer, 68, 831–837 (1993)).

Reference Example 2

Typing of Mouse Monoclonal Antibody ONS-M21

Hybridoma ONS-M21 was transplanted into mouse abdominal cavity and the resulting ascites was applied to a Protein A agarose column to obtain purified mouse monoclonal antibody. In order to investigate the types of the L chain and H chain of the resulting mouse monoclonal antibody ONS-M21, typing was performed using a mouse monoclonal antibody isotyping kit (Amersham International Plc.). As a result, ONS-M21 antibody was clearly shown to have a κ type L chain and γ1 type H chain.

Reference to Microorganisms Deposited Based on Provision 13, Part 2 of the Budapest Treaty:

Deposition Institution: National Institute of Bioscience and Human Technology, Agency of Industrial Science and Technology Address: 1-3 Higashi 1-chome, Tsukuba-shi, Ibaraki Deposition Numbers and Dates:
1. $Escherichia\ coli$ DH5α (HEF-RVL-M21p-gγ) Deposition no.: FERM BP-4472 Deposition date: Nov. 18, 1993
2. $Escherichia\ coli$ DH5α (HEF-RVH-M21-gγ1) Deposition no.: FERM BP-4471 Deposition date: Nov. 18, 1993

---

What is claimed is:

1. An L chain of an antibody which binds to human medulloblastoma cells comprising an L chain variable region (V region) and a human L chain constant region (C region), wherein the L chain V region has the amino acid sequence from the 25th Thr to the 127th Lys indicated in SEQ ID NO: 27.

2. The L chain according to claim 1, wherein the L chain C region is a Cκ region.

3. A light chain of an antibody which binds to human medulloblastoma cells comprising a light chain variable region and a human light chain constant region, wherein the light chain variable region is represented by SEQ ID NO:130 or SEO ID NO:131.

4. The light chain according to claim 3 wherein the light chain constant region is a Cκ region.

5. An H chain of an antibody which binds to human medulloblastoma cells comprising an H chain V region and a human H chain C region, wherein the H chain V region has the amino acid sequence from the 20th Glu to the 136th Ser indicated in SEQ ID NO: 29.

6. The H chain according to claim 5, wherein the H chain C region is a Cγ1 region or CT4 region.

7. A heavy chain of an antibody which binds to human medulloblastoma cells comprising a heavy chain variable region and a human heavy chain constant region, wherein the heavy chain variable region is represented by SEQ ID NO:132.

8. The heavy chain according to claim 7, wherein the heavy chain constant region is a Cγ1 region or Cγ4 region.

9. An antibody which binds to human medulloblastoma cells comprising L chains and H chains,
   wherein each L chain comprises an L chain V region and a human L chain C region,
   wherein the L chain V region has the amino acid sequence from the 25th Thr to the 127th Lys indicated in SEQ ID NO: 27, and
   each H chain comprises an H chain V region and a human H chain C region, wherein the H chain V region has the amino acid sequence from the 20th Glu to the 136th Ser indicated in SEQ ID NO: 29.

10. The antibody according to claim 9, wherein the L chain C region is a Cκ region.

11. The antibody according to claim 9, wherein the H chain C region is a Cγ1 region or Cγ4 region.

12. An antibody which binds to human medulloblastoma cells comprising heavy and light chains, wherein
    each light chain comprises a light chain M variable region and a human light chain constant region, wherein the light chain M variable region is represented by SEQ ID NO: 131, and
    each heavy chain comprises a heavy chain variable region and a human heavy chain constant region, wherein the heavy chain M variable region is represented by SEQ ID NO:132.

13. The antibody according to claim 12, wherein the [L] light chain constant region is a Cκ region.

14. The antibody according to claim 12, wherein the [H] heavy chain constant region is a Cγ1 region or Cγ4 region.

15. A single-chain Fv of an antibody which binds to human medulloblastoma cells, comprising a heavy chain variable region and a light chain variable region linked through a peptide linker, wherein the heavy chain variable region has an amino acid sequence of amino acids 1 to 116 in SEQ ID NO: 99, and the light chain variable region has an amino acid sequence of amino acids 1 to 106 in one of SEQ ID NOS: 43, 47, 51, 53, 57, 59, 63, 65, 69, 73, 75, 77, 81, 85, 87 or 91.

16. The single-chain Fv according to claim 15, wherein the light chain variable region has the amino acid sequence of amino acids 1 to 106 in SEQ ID NO: 91.

17. The single-chain Fv according to claim 15, wherein the peptide linker has the amino acid sequence of SEQ ID NO: 111.

18. The single-chain Fv according to claim 16, wherein the peptide linker has the amino acid sequence of SEQ ID NO: 111.

* * * * *

SEQUENCE LISTING (1) GENERAL INFORMATION:

(iii) NUMBER OF SEQUENCES: 132

(2) INFORMATION FOR SEQ ID NO:1:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (xi) SEQUENCE DESCRIPTION: SEQ ID NO:1:

ACTAGTCGAC ATGAAGTTGC CTGTTAGGCT GTTGGTGCTG    40

(2) INFORMATION FOR SEQ ID NO:2:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (xi) SEQUENCE DESCRIPTION: SEQ ID NO:2:

ACTAGTCGAC ATGGAGWCAG ACACACTCCT GYTATGGGT    39

(2) INFORMATION FOR SEQ ID NO:3:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:3:

ACTAGTCGAC ATGAGTGTGC TCACTCAGGT CCTGGSGTTG                  40

(2) INFORMATION FOR SEQ ID NO:4:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:4:

ACTAGTCGAC ATGAGGRCCC CTGCTCAGWT TYTTGGMWTC TTG               43

(2) INFORMATION FOR SEQ ID NO:5:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:5:

ACTAGTCGAC ATGGATTTWC AGGTGCAGAT TWTCAGCTTC                  40

(2) INFORMATION FOR SEQ ID NO:6:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:6:

ACTAGTCGAC ATGAGGTKCY YTGYTSAGYT YCTGRGG                       37

(2) INFORMATION FOR SEQ ID NO:7:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:7:

ACTAGTCGAC ATGGGCWTCA AGATGGAGTC ACAKWYYCWG G                 41

(2) INFORMATION FOR SEQ ID NO:8:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:8:

ACTAGTCGAC ATGTGGGGAY CTKTTTYCMM TTTTTCAATT G                 41

(2) INFORMATION FOR SEQ ID NO:9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:9:

```
ACTAGTCGAC ATGGTRTCCW CASCTCAGTT CCTTG                          35
```

(2) INFORMATION FOR SEQ ID NO:10:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:10:

```
ACTAGTCGAC ATGTATATAT GTTTGTTGTC TATTTCT                        37
```

(2) INFORMATION FOR SEQ ID NO:11:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:11:

```
ACTAGTCGAC ATGGAAGCCC CAGCTCAGCT TCTCTTCC                       38
```

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:12:

```
GGATCCCGGG TGGATGGTGG GAAGATG                                   27
```

(2) INFORMATION FOR SEQ ID NO:13:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:13:

```
ACTAGTCGAC ATGAAATGCA GCTGGGTCAT STTCTTC                        37
```

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:14:

```
ACTAGTCGAC ATGGGATGGA GCTRTATCAT SYTCTT                         36
```

(2) INFORMATION FOR SEQ ID NO:15:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:15:

ACTAGTCGAC ATGAAGWTGT GGTTAAACTG GGTTTTT                          37

(2) INFORMATION FOR SEQ ID NO:16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:16:

ACTAGTCGAC ATGRACTTTG GGYTCAGCTT GRTTT                            35

(2) INFORMATION FOR SEQ ID NO:17:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:17:

ACTAGTCGAC ATGGACTCCA GGCTCAATTT AGTTTTCCTT                       40

(2) INFORMATION FOR SEQ ID NO:18:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:18:

ACTAGTCGAC ATGGCTGTCY TRGSGCTRCT CTTCTGC                          37

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:19:

ACTAGTCGAC ATGGRATGGA GCKGGRTCTT TMTCTT                           36

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:20:

ACTAGTCGAC ATGAGAGTGC TGATTCTTTT GTG                              33

(2) INFORMATION FOR SEQ ID NO:21:

(i) SEQUENCE CHARACTERISTICS:
    (A) LENGTH: 40 base pairs
    (B) TYPE: nucleic acid
    (C) STRANDEDNESS: single
    (D) TOPOLOGY: linear (xi) SEQUENCE DESCRIPTION: SEQ ID NO:21:

ACTAGTCGAC ATGGMTTGGG TGTGGAMCTT GCTATTCCTG                              40

(2) INFORMATION FOR SEQ ID NO:22:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:22:

ACTAGTCGAC ATGGGCAGAC TTACATTCTC ATTCCTG                                 37

(2) INFORMATION FOR SEQ ID NO:23:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:23:

ACTAGTCGAC ATGGATTTTG GGCTGATTTT TTTTATTG                                38

(2) INFORMATION FOR SEQ ID NO:24:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:24:

ACTAGTCGAC ATGATGGTGT TAAGTCTTCT GTACCTG                                 37

(2) INFORMATION FOR SEQ ID NO:25:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:25:

GGATCCCGGG CCAGTGGATA GACAGATG                                           28

(2) INFORMATION FOR SEQ ID NO:26:

(i) SEQUENCE CHARACTERISTICS:
        (A) LENGTH: 382 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..381

(xi) SEQUENCE DESCRIPTION: SEQ ID NO:26:

ATG GAG TCA CAT ATT CAG GTC TTT GTA TAC ATG TTG CTG TGG TTG TCT          48

```
Met Glu Ser His Ile Gln Val Phe Val Tyr Met Leu Leu Trp Leu Ser
 1               5                  10                  15

GGT GTT GAT GGA GAC ATT GTG ATG ACC CAG TCT CAA AAA TTC ATG TCC          96
Gly Val Asp Gly Asp Ile Val Met Thr Gln Ser Gln Lys Phe Met Ser
                 20                  25                  30

ACA TCA GTA GGA GAC AGG GTC AGC GTC ACC TGC AAG GCC AGT CAG AAT         144
Thr Ser Val Gly Asp Arg Val Ser Val Thr Cys Lys Ala Ser Gln Asn
             35                  40                  45

GTG GGT ACT AAT GTA GCC TGG TAT CAA CAG AAA CCA GGG CAA TCT CCT         192
Val Gly Thr Asn Val Ala Trp Tyr Gln Gln Lys Pro Gly Gln Ser Pro
         50                  55                  60

AAA CCA CTG ATT TAC TCG GCA TCC TAT CGG TAC AGT GGA GTC CCT GAT         240
Lys Pro Leu Ile Tyr Ser Ala Ser Tyr Arg Tyr Ser Gly Val Pro Asp
 65                  70                  75                  80

CGC TTC ACA GGC AGT GGA TCT GGG ACA GAT TTC ACT CTC ACC ATC ACC         288
Arg Phe Thr Gly Ser Gly Ser Gly Thr Asp Phe Thr Leu Thr Ile Thr
                 85                  90                  95

AAT GTG CAG TCT GAA GAC TTG GCA GAC TAT TTC TGT CAG CAA TAT AAC         336
Asn Val Gln Ser Glu Asp Leu Ala Asp Tyr Phe Cys Gln Gln Tyr Asn
             100                 105                 110

AGC TAT CCT CGG GCG TTC GGT GGA GGC ACC AAA CTG GAA ATC AAA             381
Ser Tyr Pro Arg Ala Phe Gly Gly Gly Thr Lys Leu Glu Ile Lys
         115                 120                 125

C                                                                       382
```

(2) INFORMATION FOR SEQ ID NO:27:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO:27:

```
Met Glu Ser His Ile Gln Val Phe Val Tyr Met Leu Leu Trp Leu Ser
 1               5                  10                  15

Gly Val Asp Gly Asp Ile Val Met Thr Gln Ser Gln Lys Phe Met Ser
                 20                  25                  30

Thr Ser Val Gly Asp Arg Val Ser Val Thr Cys Lys Ala Ser Gln Asn
             35                  40                  45

Val Gly Thr Asn Val Ala Trp Tyr Gln Gln Lys Pro Gly Gln Ser Pro
         50                  55                  60

Lys Pro Leu Ile Tyr Ser Ala Ser Tyr Arg Tyr Ser Gly Val Pro Asp
 65                  70                  75                  80

Arg Phe Thr Gly Ser Gly Ser Gly Thr Asp Phe Thr Leu Thr Ile Thr
                 85                  90                  95

Asn Val Gln Ser Glu Asp Leu Ala Asp Tyr Phe Cys Gln Gln Tyr Asn
             100                 105                 110

Ser Tyr Pro Arg Ala Phe Gly Gly Gly Thr Lys Leu Glu Ile Lys
         115                 120                 125
```

(2) INFORMATION FOR SEQ ID NO:28:

(i) SEQUENCE CHARACTERISTICS:
        (A) LENGTH: 409 base pairs
        (B) TYPE: nucleic acid
        (C) STRANDEDNESS: single
        (D) TOPOLOGY: linear (ix) FEATURE:

```
        (A) NAME/KEY: CDS
        (B) LOCATION: 1..408

(ix) FEATURE:
        (A) NAME/KEY: mat_peptide
        (B) LOCATION: 1..408

(xi) SEQUENCE DESCRIPTION: SEQ ID NO:28:

ATG AAA TGC AGC TGG GTC ATG TTC TTC CTG ATG GCA GTG GTT ACA GGG      48
Met Lys Cys Ser Trp Val Met Phe Phe Leu Met Ala Val Val Thr Gly
 1               5                  10                  15

GTC AAT TCA GAG GTT CAG CTG CAG CAG TCT GGG GCA GAG CTT GTG AAG      96
Val Asn Ser Glu Val Gln Leu Gln Gln Ser Gly Ala Glu Leu Val Lys
             20                  25                  30

CCA GGG GCC TCA GTC AAG TTG TCC TGC ACA GCT TCT GGC TTC AAC ATT     144
Pro Gly Ala Ser Val Lys Leu Ser Cys Thr Ala Ser Gly Phe Asn Ile
         35                  40                  45

AAA GAC ACC TAT ATA CAC TGG GCG AAG CAG AGG CCT GAA CAG GGC CTG     192
Lys Asp Thr Tyr Ile His Trp Ala Lys Gln Arg Pro Glu Gln Gly Leu
     50                  55                  60

GAG TGG ATT GGA AGG ATT GAT CCT GCG GAT GGT AAT ACT AAA TAT GAC     240
Glu Trp Ile Gly Arg Ile Asp Pro Ala Asp Gly Asn Thr Lys Tyr Asp
 65                  70                  75                  80

CCG AAG TTC CAG GGC AAG GCC ACT ATA ACA GCA GAC ACA TCC TCC AAC     288
Pro Lys Phe Gln Gly Lys Ala Thr Ile Thr Ala Asp Thr Ser Ser Asn
                 85                  90                  95

ACA GCC TAC CTG CAG CTC AGC AGC CTG ACA TCT GAG GAC ACT GCC GTC     336
Thr Ala Tyr Leu Gln Leu Ser Ser Leu Thr Ser Glu Asp Thr Ala Val
            100                 105                 110

TAT TAC TGT GCT TCG GCC TAC TAT GTT AAC CAG GAC TAC TGG GGT CAA     384
Tyr Tyr Cys Ala Ser Ala Tyr Tyr Val Asn Gln Asp Tyr Trp Gly Gln
        115                 120                 125

GGA ACC TCA GTC ACC GTC TCC TCA G                                   409
Gly Thr Ser Val Thr Val Ser Ser
    130                 135

(2) INFORMATION FOR SEQ ID NO:29:

(i) SEQUENCE CHARACTERISTICS:
        (A) LENGTH: 136 amino acids
        (B) TYPE: amino acid
        (D) TOPOLOGY: linear (ii) MOLECULE TYPE: protein (xi) SEQUENCE DESCRIPTION: SEQ ID NO:29:

Met Lys Cys Ser Trp Val Met Phe Phe Leu Met Ala Val Val Thr Gly
 1               5                  10                  15

Val Asn Ser Glu Val Gln Leu Gln Gln Ser Gly Ala Glu Leu Val Lys
             20                  25                  30

Pro Gly Ala Ser Val Lys Leu Ser Cys Thr Ala Ser Gly Phe Asn Ile
         35                  40                  45

Lys Asp Thr Tyr Ile His Trp Ala Lys Gln Arg Pro Glu Gln Gly Leu
     50                  55                  60

Glu Trp Ile Gly Arg Ile Asp Pro Ala Asp Gly Asn Thr Lys Tyr Asp
 65                  70                  75                  80

Pro Lys Phe Gln Gly Lys Ala Thr Ile Thr Ala Asp Thr Ser Ser Asn
                 85                  90                  95

Thr Ala Tyr Leu Gln Leu Ser Ser Leu Thr Ser Glu Asp Thr Ala Val
            100                 105                 110

Tyr Tyr Cys Ala Ser Ala Tyr Tyr Val Asn Gln Asp Tyr Trp Gly Gln
```

115             120             125

Gly Thr Ser Val Thr Val Ser Ser
    130             135

(2) INFORMATION FOR SEQ ID NO:30:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (xi) SEQUENCE DESCRIPTION: SEQ ID NO:30:

GATAAGCTTC CACCATGGGC TTCAAGATGG AGTC                          34

(2) INFORMATION FOR SEQ ID NO:31:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (xi) SEQUENCE DESCRIPTION: SEQ ID NO:31:

GGCGGATCCA CTCACGTTTG ATTTCCAGTT TGGT                          34

(2) INFORMATION FOR SEQ ID NO:32:

(i) SEQUENCE CHARACTERISTICS:
       (A) LENGTH: 43 base pairs
       (B) TYPE: nucleic acid
       (C) STRANDEDNESS: single
       (D) TOPOLOGY: linear (xi) SEQUENCE DESCRIPTION: SEQ ID NO:32:

GATAAGCTTC CACCATGAAA TGCAGCTGGG TCATGTTCTT CCT                43

(2) INFORMATION FOR SEQ ID NO:33:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (xi) SEQUENCE DESCRIPTION: SEQ ID NO:33:

GGCGGATCCA CTCACCTGAG GAGACGGTGA CTGA                          34

(2) INFORMATION FOR SEQ ID NO:34:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (xi) SEQUENCE DESCRIPTION: SEQ ID NO:34:

CAGACAGTGG TTCAAAGT                                            18

(2) INFORMATION FOR SEQ ID NO:35:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (xi) SEQUENCE DESCRIPTION: SEQ ID NO:35:

GAATTCGGAT CCACTCACGT TTGATT                                                    26

(2) INFORMATION FOR SEQ ID NO:36:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:36:

AGTCAGAATG TGGGTACTAA TGTAGCCTGG TACCAGCAGA AGCC                                 44

(2) INFORMATION FOR SEQ ID NO:37:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:37:

TCCTATCGGT ACAGTGGTGT GCCAAGCAGA TTCAGCGG                                       38

(2) INFORMATION FOR SEQ ID NO:38:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:38:

GCTACCTACT ACTGCCAGCA ATATAACAGC TATCCTCGGG CGTTCGG                             47

(2) INFORMATION FOR SEQ ID NO:39:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:39:

ACATTAGTAC CCACATTCTG ACTGGCCTTA CAGGTGATGG TCAC                                 44

(2) INFORMATION FOR SEQ ID NO:40:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:40:

GGCACACCAC TGTACCGATA GGATGCCGAG TAGATCAGCA GCTTTGG                             47

(2) INFORMATION FOR SEQ ID NO:41:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:41:

```
GGATAGCTGT TATATTGCTG GCAGTAGTAG GTAGCGATGT CCTC                    44
```

(2) INFORMATION FOR SEQ ID NO:42:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58..378

(xi) SEQUENCE DESCRIPTION: SEQ ID NO:42:

```
ATG GGA TGG AGC TGT ATC ATC CTC TCC TTG GTA GCA ACA GCT ACA GGT    48
Met Gly Trp Ser Cys Ile Ile Leu Ser Leu Val Ala Thr Ala Thr Gly
-19         -15                 -10                 -5

GTC CAC TCC GAC ATC CAG ATG ACC CAG AGC CCA AGC AGC CTG AGC GCC    96
Val His Ser Asp Ile Gln Met Thr Gln Ser Pro Ser Ser Leu Ser Ala
            1               5                   10

AGC GTG GGT GAC AGA GTG ACC ATC ACC TGT AAG GCC AGT CAG AAT GTG   144
Ser Val Gly Asp Arg Val Thr Ile Thr Cys Lys Ala Ser Gln Asn Val
        15                  20                  25

GGT ACT AAT GTA GCC TGG TAC CAG CAG AAG CCA GGA AAG GCT CCA AAG   192
Gly Thr Asn Val Ala Trp Tyr Gln Gln Lys Pro Gly Lys Ala Pro Lys
30                  35                  40                  45

CTG CTG ATC TAC TCG GCA TCC TAT CGG TAC AGT GGT GTG CCA AGC AGA   240
Leu Leu Ile Tyr Ser Ala Ser Tyr Arg Tyr Ser Gly Val Pro Ser Arg
                50                  55                  60

TTC AGC GGT AGC GGT AGC GGT ACC GAC TTC ACC TTC ACC ATC AGC AGC   288
Phe Ser Gly Ser Gly Ser Gly Thr Asp Phe Thr Phe Thr Ile Ser Ser
            65                  70                  75

CTC CAG CCA GAG GAC ATC GCC ACC TAC TAC TGC CAG CAA TAT AAC AGC   336
Leu Gln Pro Glu Asp Ile Ala Thr Tyr Tyr Cys Gln Gln Tyr Asn Ser
        80                  85                  90

TAT CCT CGG GCG TTC GGC CAA GGG ACC AAG GTG GAA ATC AAA           378
Tyr Pro Arg Ala Phe Gly Gln Gly Thr Lys Val Glu Ile Lys
    95                  100                 105

C                                                                 379
```

(2) INFORMATION FOR SEQ ID NO:43:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:43:

```
Met Gly Trp Ser Cys Ile Ile Leu Ser Leu Val Ala Thr Ala Thr Gly
-19         -15                 -10                 -5

Val His Ser Asp Ile Gln Met Thr Gln Ser Pro Ser Ser Leu Ser Ala
            1               5                   10

Ser Val Gly Asp Arg Val Thr Ile Thr Cys Lys Ala Ser Gln Asn Val
        15                  20                  25

Gly Thr Asn Val Ala Trp Tyr Gln Gln Lys Pro Gly Lys Ala Pro Lys
30                  35                  40                  45
```

```
Leu Leu Ile Tyr Ser Ala Ser Tyr Arg Tyr Ser Gly Val Pro Ser Arg
            50                  55                  60

Phe Ser Gly Ser Gly Ser Gly Thr Asp Phe Thr Phe Thr Ile Ser Ser
            65                  70                  75

Leu Gln Pro Glu Asp Ile Ala Thr Tyr Tyr Cys Gln Gln Tyr Asn Ser
        80                  85                  90

Tyr Pro Arg Ala Phe Gly Gln Gly Thr Lys Val Glu Ile Lys
 95                 100                 105

(2) INFORMATION FOR SEQ ID NO:44:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:44:

GGTACCGACT ACACCTTCAC CATCAGCAGC C                              31

(2) INFORMATION FOR SEQ ID NO:45:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:45:

GGTGAAGGTG TAGTCGGTAC CGCTACCGCT A                              31

(2) INFORMATION FOR SEQ ID NO:46:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58..378

(xi) SEQUENCE DESCRIPTION: SEQ ID NO:46:

ATG GGA TGG AGC TGT ATC ATC CTC TCC TTG GTA GCA ACA GCT ACA GGT      48
Met Gly Trp Ser Cys Ile Ile Leu Ser Leu Val Ala Thr Ala Thr Gly
-19             -15                 -10                 -5

GTC CAC TCC GAC ATC CAG ATG ACC CAG AGC CCA AGC AGC CTG AGC GCC      96
Val His Ser Asp Ile Gln Met Thr Gln Ser Pro Ser Ser Leu Ser Ala
            1               5                  10

AGC GTG GGT GAC AGA GTG ACC ATC ACC TGT AAG GCC AGT CAG AAT GTG     144
Ser Val Gly Asp Arg Val Thr Ile Thr Cys Lys Ala Ser Gln Asn Val
        15                  20                  25

GGT ACT AAT GTA GCC TGG TAC CAG CAG AAG CCA GGA AAG GCT CCA AAG     192
Gly Thr Asn Val Ala Trp Tyr Gln Gln Lys Pro Gly Lys Ala Pro Lys
    30                  35                  40                  45

CTG CTG ATC TAC TCG GCA TCC TAT CGG TAC AGT GGT GTG CCA AGC AGA     240
Leu Leu Ile Tyr Ser Ala Ser Tyr Arg Tyr Ser Gly Val Pro Ser Arg
            50                  55                  60

TTC AGC GGT AGC GGT AGT GGT ACC GAC TAC ACC TTC ACC ATC AGC AGC     288
```

```
Phe Ser Gly Ser Gly Ser Gly Thr Asp Tyr Thr Phe Thr Ile Ser Ser
            65                  70                  75

CTC CAG CCA GAG GAC ATC GCC ACC TAC TAC TGC CAG CAA TAT AAC AGC          336
Leu Gln Pro Glu Asp Ile Ala Thr Tyr Tyr Cys Gln Gln Tyr Asn Ser
        80                  85                  90

TAT CCT CGG GCG TTC GGC CAA GGG ACC AAG GTG GAA ATC AAA                  378
Tyr Pro Arg Ala Phe Gly Gln Gly Thr Lys Val Glu Ile Lys
    95                  100                 105

C                                                                        379
```

(2) INFORMATION FOR SEQ ID NO:47:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:47:

```
Met Gly Trp Ser Cys Ile Ile Leu Ser Leu Val Ala Thr Ala Thr Gly
-19             -15                 -10                 -5

Val His Ser Asp Ile Gln Met Thr Gln Ser Pro Ser Ser Leu Ser Ala
            1                   5                   10

Ser Val Gly Asp Arg Val Thr Ile Thr Cys Lys Ala Ser Gln Asn Val
        15                  20                  25

Gly Thr Asn Val Ala Trp Tyr Gln Gln Lys Pro Gly Lys Ala Pro Lys
    30                  35                  40                  45

Leu Leu Ile Tyr Ser Ala Ser Tyr Arg Tyr Ser Gly Val Pro Ser Arg
            50                  55                  60

Phe Ser Gly Ser Gly Ser Gly Thr Asp Tyr Thr Phe Thr Ile Ser Ser
            65                  70                  75

Leu Gln Pro Glu Asp Ile Ala Thr Tyr Tyr Cys Gln Gln Tyr Asn Ser
        80                  85                  90

Tyr Pro Arg Ala Phe Gly Gln Gly Thr Lys Val Glu Ile Lys
    95                  100                 105
```

(2) INFORMATION FOR SEQ ID NO:48:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:48:

```
GCTACCTACT TCTGCCAGCA ATATAACAG                                           29
```

(2) INFORMATION FOR SEQ ID NO:49:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:49:

```
TGCTGGCAGA AGTAGGTAGC GATGTCCTC                                           29
```

(2) INFORMATION FOR SEQ ID NO:50:

(i) SEQUENCE CHARACTERISTICS:

(A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58..378

(xi) SEQUENCE DESCRIPTION: SEQ ID NO:50:

```
ATG GGA TGG AGC TGT ATC ATC CTC TCC TTG GTA GCA ACA GCT ACA GGT     48
Met Gly Trp Ser Cys Ile Ile Leu Ser Leu Val Ala Thr Ala Thr Gly
-19             -15                 -10                 -5

GTC CAC TCC GAC ATC CAG ATG ACC CAG AGC CCA AGC AGC CTG AGC GCC     96
Val His Ser Asp Ile Gln Met Thr Gln Ser Pro Ser Ser Leu Ser Ala
            1               5                   10

AGC GTG GGT GAC AGA GTG ACC ATC ACC TGT AAG GCC AGT CAG AAT GTG    144
Ser Val Gly Asp Arg Val Thr Ile Thr Cys Lys Ala Ser Gln Asn Val
        15                  20                  25

GGT ACT AAT GTA GCC TGG TAC CAG CAG AAG CCA GGA AAG GCT CCA AAG    192
Gly Thr Asn Val Ala Trp Tyr Gln Gln Lys Pro Gly Lys Ala Pro Lys
30                  35                  40                  45

CTG CTG ATC TAC TCG GCA TCC TAT CGG TAC AGT GGT GTG CCA AGC AGA    240
Leu Leu Ile Tyr Ser Ala Ser Tyr Arg Tyr Ser Gly Val Pro Ser Arg
                50                  55                  60

TTC AGC GGT AGC GGT AGC GGT ACC GAC TTC ACC TTC ACC ATC AGC AGC    288
Phe Ser Gly Ser Gly Ser Gly Thr Asp Phe Thr Phe Thr Ile Ser Ser
                    65                  70                  75

CTC CAG CCA GAG GAC ATC GCC ACC TAC TTC TGC CAG CAA TAT AAC AGC    336
Leu Gln Pro Glu Asp Ile Ala Thr Tyr Phe Cys Gln Gln Tyr Asn Ser
                80                  85                  90

TAT CCT CGG GCG TTC GGC CAA GGG ACC AAG GTG GAA ATC AAA            378
Tyr Pro Arg Ala Phe Gly Gln Gly Thr Lys Val Glu Ile Lys
    95                  100                 105

C                                                                  379
```

(2) INFORMATION FOR SEQ ID NO:51:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:51:

```
Met Gly Trp Ser Cys Ile Ile Leu Ser Leu Val Ala Thr Ala Thr Gly
-19             -15                 -10                 -5

Val His Ser Asp Ile Gln Met Thr Gln Ser Pro Ser Ser Leu Ser Ala
            1               5                   10

Ser Val Gly Asp Arg Val Thr Ile Thr Cys Lys Ala Ser Gln Asn Val
        15                  20                  25

Gly Thr Asn Val Ala Trp Tyr Gln Gln Lys Pro Gly Lys Ala Pro Lys
30                  35                  40                  45

Leu Leu Ile Tyr Ser Ala Ser Tyr Arg Tyr Ser Gly Val Pro Ser Arg
                50                  55                  60

Phe Ser Gly Ser Gly Ser Gly Thr Asp Phe Thr Phe Thr Ile Ser Ser
                    65                  70                  75
```

```
Leu Gln Pro Glu Asp Ile Ala Thr Tyr Phe Cys Gln Gln Tyr Asn Ser
        80                  85                  90

Tyr Pro Arg Ala Phe Gly Gln Gly Thr Lys Val Glu Ile Lys
        95                  100                 105

(2) INFORMATION FOR SEQ ID NO:52:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58..378

(xi) SEQUENCE DESCRIPTION: SEQ ID NO:52:

ATG GGA TGG AGC TGT ATC ATC CTC TCC TTG GTA GCA ACA GCT ACA GGT        48
Met Gly Trp Ser Cys Ile Ile Leu Ser Leu Val Ala Thr Ala Thr Gly
-19             -15                 -10                 -5

GTC CAC TCC GAC ATC CAG ATG ACC CAG AGC CCA AGC AGC CTG AGC GCC        96
Val His Ser Asp Ile Gln Met Thr Gln Ser Pro Ser Ser Leu Ser Ala
            1               5                   10

AGC GTG GGT GAC AGA GTG ACC ATC ACC TGT AAG GCC AGT CAG AAT GTG       144
Ser Val Gly Asp Arg Val Thr Ile Thr Cys Lys Ala Ser Gln Asn Val
        15                  20                  25

GGT ACT AAT GTA GCC TGG TAC CAG CAG AAG CCA GGA AAG GCT CCA AAG       192
Gly Thr Asn Val Ala Trp Tyr Gln Gln Lys Pro Gly Lys Ala Pro Lys
    30                  35                  40                  45

CTG CTG ATC TAC TCG GCA TCC TAT CGG TAC AGT GGT GTG CCA AGC AGA       240
Leu Leu Ile Tyr Ser Ala Ser Tyr Arg Tyr Ser Gly Val Pro Ser Arg
                50                  55                  60

TTC AGC GGT AGC GGT AGC GGT ACC GAC TAC ACC TTC ACC ATC AGC AGC       288
Phe Ser Gly Ser Gly Ser Gly Thr Asp Tyr Thr Phe Thr Ile Ser Ser
            65                  70                  75

CTC CAG CCA GAG GAC ATC GCC ACC TAC TTC TGC CAG CAA TAT AAC AGC       336
Leu Gln Pro Glu Asp Ile Ala Thr Tyr Phe Cys Gln Gln Tyr Asn Ser
        80                  85                  90

TAT CCT CGG GCG TTC GGC CAA GGG ACC AAG GTG GAA ATC AAA               378
Tyr Pro Arg Ala Phe Gly Gln Gly Thr Lys Val Glu Ile Lys
        95                  100                 105

C                                                                      379

(2) INFORMATION FOR SEQ ID NO:53:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:53:

Met Gly Trp Ser Cys Ile Ile Leu Ser Leu Val Ala Thr Ala Thr Gly
-19             -15                 -10                 -5

Val His Ser Asp Ile Gln Met Thr Gln Ser Pro Ser Ser Leu Ser Ala
            1               5                   10

Ser Val Gly Asp Arg Val Thr Ile Thr Cys Lys Ala Ser Gln Asn Val
        15                  20                  25
```

```
Gly Thr Asn Val Ala Trp Tyr Gln Gln Lys Pro Gly Lys Ala Pro Lys
 30                  35                  40                  45

Leu Leu Ile Tyr Ser Ala Ser Tyr Arg Tyr Ser Gly Val Pro Ser Arg
             50                  55                  60

Phe Ser Gly Ser Gly Ser Gly Thr Asp Tyr Thr Phe Thr Ile Ser Ser
             65                  70                  75

Leu Gln Pro Glu Asp Ile Ala Thr Tyr Phe Cys Gln Gln Tyr Asn Ser
         80                  85                  90

Tyr Pro Arg Ala Phe Gly Gln Gly Thr Lys Val Glu Ile Lys
         95                 100                 105
```

(2) INFORMATION FOR SEQ ID NO:54:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:54:

```
TGACAGAGTG TCCGTCACCT GTAAGGCCA                                    29
```

(2) INFORMATION FOR SEQ ID NO:55:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:55:

```
TTACAGGTGA CGGACACTCT GTCACCCAC                                    29
```

(2) INFORMATION FOR SEQ ID NO:56:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58..378

(xi) SEQUENCE DESCRIPTION: SEQ ID NO:56:

```
ATG GGA TGG AGC TGT ATC ATC CTC TCC TTG GTA GCA ACA GCT ACA GGT       48
Met Gly Trp Ser Cys Ile Ile Leu Ser Leu Val Ala Thr Ala Thr Gly
-19             -15                 -10                  -5

GTC CAC TCC GAC ATC CAG ATG ACC CAG AGC CCA AGC AGC CTG AGC GCC       96
Val His Ser Asp Ile Gln Met Thr Gln Ser Pro Ser Ser Leu Ser Ala
                  1               5                  10

AGC GTG GGT GAC AGA GTG TCC GTC ACC TGT AAG GCC AGT CAG AAT GTG      144
Ser Val Gly Asp Arg Val Ser Val Thr Cys Lys Ala Ser Gln Asn Val
         15                  20                  25

GGT ACT AAT GTA GCC TGG TAC CAG CAG AAG CCA GGA AAG GCT CCA AAG      192
Gly Thr Asn Val Ala Trp Tyr Gln Gln Lys Pro Gly Lys Ala Pro Lys
 30                  35                  40                  45

CTG CTG ATC TAC TCG GCA TCC TAT CGG TAC AGT GGT GTG CCA AGC AGA      240
Leu Leu Ile Tyr Ser Ala Ser Tyr Arg Tyr Ser Gly Val Pro Ser Arg
```

```
TTC AGC GGT AGC GGT AGC GGT ACC GAC TTC ACC TTC ACC ATC AGC AGC      288
Phe Ser Gly Ser Gly Ser Gly Thr Asp Phe Thr Phe Thr Ile Ser Ser
            65                  70                  75

CTC CAG CCA GAG GAC ATC GCC ACC TAC TAC TGC CAG CAA TAT AAC AGC      336
Leu Gln Pro Glu Asp Ile Ala Thr Tyr Tyr Cys Gln Gln Tyr Asn Ser
        80                  85                  90

TAT CCT CGG GCG TTC GGC CAA GGG ACC AAG GTG GAA ATC AAA              378
Tyr Pro Arg Ala Phe Gly Gln Gly Thr Lys Val Glu Ile Lys
    95                  100                 105

C                                                                    379
```

(2) INFORMATION FOR SEQ ID NO:57:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:57:

```
Met Gly Trp Ser Cys Ile Ile Leu Ser Leu Val Ala Thr Ala Thr Gly
-19             -15                 -10                 -5

Val His Ser Asp Ile Gln Met Thr Gln Ser Pro Ser Ser Leu Ser Ala
      1                 5                   10

Ser Val Gly Asp Arg Val Ser Val Thr Cys Lys Ala Ser Gln Asn Val
    15                  20                  25

Gly Thr Asn Val Ala Trp Tyr Gln Gln Lys Pro Gly Lys Ala Pro Lys
30                  35                  40                  45

Leu Leu Ile Tyr Ser Ala Ser Tyr Arg Tyr Ser Gly Val Pro Ser Arg
            50                  55                  60

Phe Ser Gly Ser Gly Ser Gly Thr Asp Phe Thr Phe Thr Ile Ser Ser
            65                  70                  75

Leu Gln Pro Glu Asp Ile Ala Thr Tyr Tyr Cys Gln Gln Tyr Asn Ser
        80                  85                  90

Tyr Pro Arg Ala Phe Gly Gln Gly Thr Lys Val Glu Ile Lys
    95                  100                 105
```

(2) INFORMATION FOR SEQ ID NO:58:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58..378

(xi) SEQUENCE DESCRIPTION: SEQ ID NO:58:

```
ATG GGA TGG AGC TGT ATC ATC CTC TCC TTG GTA GCA ACA GCT ACA GGT      48
Met Gly Trp Ser Cys Ile Ile Leu Ser Leu Val Ala Thr Ala Thr Gly
-19             -15                 -10                 -5

GTC CAC TCC GAC ATC CAG ATG ACC CAG AGC CCA AGC AGC CTG AGC GCC      96
Val His Ser Asp Ile Gln Met Thr Gln Ser Pro Ser Ser Leu Ser Ala
      1                 5                   10
```

```
AGC GTG GGT GAC AGA GTG TCC GTC ACC TGT AAG GCC AGT CAG AAT GTG    144
Ser Val Gly Asp Arg Val Ser Val Thr Cys Lys Ala Ser Gln Asn Val
     15                  20                  25

GGT ACT AAT GTA GCC TGG TAC CAG CAG AAG CCA GGA AAG GCT CCA AAG    192
Gly Thr Asn Val Ala Trp Tyr Gln Gln Lys Pro Gly Lys Ala Pro Lys
 30              35                  40                  45

CTG CTG ATC TAC TCG GCA TCC TAT CGG TAC AGT GGT GTG CCA AGC AGA    240
Leu Leu Ile Tyr Ser Ala Ser Tyr Arg Tyr Ser Gly Val Pro Ser Arg
             50                  55                  60

TTC AGC GGT AGC GGT AGC GGT ACC GAC TTC ACC TTC ACC ATC AGC AGC    288
Phe Ser Gly Ser Gly Ser Gly Thr Asp Phe Thr Phe Thr Ile Ser Ser
         65                  70                  75

CTC CAG CCA GAG GAC ATC GCC ACC TAC TTC TGC CAG CAA TAT AAC AGC    336
Leu Gln Pro Glu Asp Ile Ala Thr Tyr Phe Cys Gln Gln Tyr Asn Ser
     80                  85                  90

TAT CCT CGG GCG TTC GGC CAA GGG ACC AAG GTG GAA ATC AAA            378
Tyr Pro Arg Ala Phe Gly Gln Gly Thr Lys Val Glu Ile Lys
 95                 100                 105

C                                                                  379
```

(2) INFORMATION FOR SEQ ID NO:59:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:59:

```
Met Gly Trp Ser Cys Ile Ile Leu Ser Leu Val Ala Thr Ala Thr Gly
-19             -15                 -10                 -5

Val His Ser Asp Ile Gln Met Thr Gln Ser Pro Ser Ser Leu Ser Ala
             1                   5                  10

Ser Val Gly Asp Arg Val Ser Val Thr Cys Lys Ala Ser Gln Asn Val
     15                  20                  25

Gly Thr Asn Val Ala Trp Tyr Gln Gln Lys Pro Gly Lys Ala Pro Lys
 30              35                  40                  45

Leu Leu Ile Tyr Ser Ala Ser Tyr Arg Tyr Ser Gly Val Pro Ser Arg
             50                  55                  60

Phe Ser Gly Ser Gly Ser Gly Thr Asp Phe Thr Phe Thr Ile Ser Ser
         65                  70                  75

Leu Gln Pro Glu Asp Ile Ala Thr Tyr Phe Cys Gln Gln Tyr Asn Ser
     80                  85                  90

Tyr Pro Arg Ala Phe Gly Gln Gly Thr Lys Val Glu Ile Lys
 95                 100                 105
```

(2) INFORMATION FOR SEQ ID NO:60:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:60:

```
GACTTCACCT TGACCATCAG CAGCCT                                       26
```

(2) INFORMATION FOR SEQ ID NO:61:

(i) SEQUENCE CHARACTERISTICS:

(A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:61:

CTGCTGATGG TCAAGGTGAA GTCGGT                                           26

(2) INFORMATION FOR SEQ ID NO:62:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58..378

(xi) SEQUENCE DESCRIPTION: SEQ ID NO:62:

```
ATG GGA TGG AGC TGT ATC ATC CTC TCC TTG GTA GCA ACA GCT ACA GGT        48
Met Gly Trp Ser Cys Ile Ile Leu Ser Leu Val Ala Thr Ala Thr Gly
-19             -15                 -10                 -5

GTC CAC TCC GAC ATC CAG ATG ACC CAG AGC CCA AGC AGC CTG AGC GCC        96
Val His Ser Asp Ile Gln Met Thr Gln Ser Pro Ser Ser Leu Ser Ala
            1               5                   10

AGC GTG GGT GAC AGA GTG TCC GTC ACC TGT AAG GCC AGT CAG AAT GTG       144
Ser Val Gly Asp Arg Val Ser Val Thr Cys Lys Ala Ser Gln Asn Val
        15                  20                  25

GGT ACT AAT GTA GCC TGG TAC CAG CAG AAG CCA GGA AAG GCT CCA AAG       192
Gly Thr Asn Val Ala Trp Tyr Gln Gln Lys Pro Gly Lys Ala Pro Lys
30                  35                  40                  45

CTG CTG ATC TAC TCG GCA TCC TAT CGG TAC AGT GGT GTG CCA AGC AGA       240
Leu Leu Ile Tyr Ser Ala Ser Tyr Arg Tyr Ser Gly Val Pro Ser Arg
                50                  55                  60

TTC AGC GGT AGC GGT AGC GGT ACC GAC TTC ACC TTG ACC ATC AGC AGC       288
Phe Ser Gly Ser Gly Ser Gly Thr Asp Phe Thr Leu Thr Ile Ser Ser
            65                  70                  75

CTC CAG CCA GAG GAC ATC GCC ACC TAC TTC TGC CAG CAA TAT AAC AGC       336
Leu Gln Pro Glu Asp Ile Ala Thr Tyr Phe Cys Gln Gln Tyr Asn Ser
        80                  85                  90

TAT CCT CGG GCG TTC GGC CAA GGG ACC AAG GTG GAA ATC AAA              378
Tyr Pro Arg Ala Phe Gly Gln Gly Thr Lys Val Glu Ile Lys
    95                  100                 105

C                                                                    379
```

(2) INFORMATION FOR SEQ ID NO:63:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:63:

```
Met Gly Trp Ser Cys Ile Ile Leu Ser Leu Val Ala Thr Ala Thr Gly
-19             -15                 -10                 -5

Val His Ser Asp Ile Gln Met Thr Gln Ser Pro Ser Ser Leu Ser Ala
            1               5                   10
```

```
Ser Val Gly Asp Arg Val Ser Val Thr Cys Lys Ala Ser Gln Asn Val
    15                  20                  25

Gly Thr Asn Val Ala Trp Tyr Gln Gln Lys Pro Gly Lys Ala Pro Lys
 30                  35                  40                  45

Leu Leu Ile Tyr Ser Ala Ser Tyr Arg Tyr Ser Gly Val Pro Ser Arg
                 50                  55                  60

Phe Ser Gly Ser Gly Ser Gly Thr Asp Phe Thr Leu Thr Ile Ser Ser
             65                  70                  75

Leu Gln Pro Glu Asp Ile Ala Thr Tyr Phe Cys Gln Gln Tyr Asn Ser
         80                  85                  90

Tyr Pro Arg Ala Phe Gly Gln Gly Thr Lys Val Glu Ile Lys
     95                 100                 105
```

(2) INFORMATION FOR SEQ ID NO:64:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58..378

(xi) SEQUENCE DESCRIPTION: SEQ ID NO:64:

```
ATG GGA TGG AGC TGT ATC ATC CTC TCC TTG GTA GCA ACA GCT ACA GGT        48
Met Gly Trp Ser Cys Ile Ile Leu Ser Leu Val Ala Thr Ala Thr Gly
-19             -15                 -10                  -5

GTC CAC TCC GAC ATC CAG ATG ACC CAG AGC CCA AGC AGC CTG AGC GCC        96
Val His Ser Asp Ile Gln Met Thr Gln Ser Pro Ser Ser Leu Ser Ala
             1                   5                  10

AGC GTG GGT GAC AGA GTG ACC ATC ACC TGT AAG GCC AGT CAG AAT GTG       144
Ser Val Gly Asp Arg Val Thr Ile Thr Cys Lys Ala Ser Gln Asn Val
         15                  20                  25

GGT ACT AAT GTA GCC TGG TAC CAG CAG AAG CCA GGA AAG GCT CCA AAG       192
Gly Thr Asn Val Ala Trp Tyr Gln Gln Lys Pro Gly Lys Ala Pro Lys
 30                  35                  40                  45

CTG CTG ATC TAC TCG GCA TCC TAT CGG TAC AGT GGT GTG CCA AGC AGA       240
Leu Leu Ile Tyr Ser Ala Ser Tyr Arg Tyr Ser Gly Val Pro Ser Arg
                 50                  55                  60

TTC AGC GGT AGC GGT AGC GGT ACC GAC TTC ACC TTG ACC ATC AGC AGC       288
Phe Ser Gly Ser Gly Ser Gly Thr Asp Phe Thr Leu Thr Ile Ser Ser
             65                  70                  75

CTC CAG CCA GAG GAC ATC GCC ACC TAC TAC TGC CAG CAA TAT AAC AGC       336
Leu Gln Pro Glu Asp Ile Ala Thr Tyr Tyr Cys Gln Gln Tyr Asn Ser
         80                  85                  90

TAT CCT CGG GCG TTC GGC CAA GGG ACC AAG GTG GAA ATC AAA               378
Tyr Pro Arg Ala Phe Gly Gln Gly Thr Lys Val Glu Ile Lys
     95                 100                 105

C                                                                     379
```

(2) INFORMATION FOR SEQ ID NO:65:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:65:

Met Gly Trp Ser Cys Ile Ile Leu Ser Leu Val Ala Thr Ala Thr Gly
-19              -15                 -10                 -5

Val His Ser Asp Ile Gln Met Thr Gln Ser Pro Ser Ser Leu Ser Ala
                 1               5               10

Ser Val Gly Asp Arg Val Thr Ile Thr Cys Lys Ala Ser Gln Asn Val
     15              20              25

Gly Thr Asn Val Ala Trp Tyr Gln Gln Lys Pro Gly Lys Ala Pro Lys
 30              35              40              45

Leu Leu Ile Tyr Ser Ala Ser Tyr Arg Tyr Ser Gly Val Pro Ser Arg
             50              55              60

Phe Ser Gly Ser Gly Ser Gly Thr Asp Phe Thr Leu Thr Ile Ser Ser
             65              70              75

Leu Gln Pro Glu Asp Ile Ala Thr Tyr Tyr Cys Gln Gln Tyr Asn Ser
             80              85              90

Tyr Pro Arg Ala Phe Gly Gln Gly Thr Lys Val Glu Ile Lys
         95              100             105

(2) INFORMATION FOR SEQ ID NO:66:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:66:

GGACAGAGTC CAAAGCCGCT GATCTACTC                                              29

(2) INFORMATION FOR SEQ ID NO:67:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:67:

ATCAGCGGCT TTGGACTCTG TCCTGGCTT                                              29

(2) INFORMATION FOR SEQ ID NO:68:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58..378

(xi) SEQUENCE DESCRIPTION: SEQ ID NO:68:

ATG GGA TGG AGC TGT ATC ATC CTC TCC TTG GTA GCA ACA GCT ACA GGT              48
Met Gly Trp Ser Cys Ile Ile Leu Ser Leu Val Ala Thr Ala Thr Gly
-19              -15                 -10                 -5

GTC CAC TCC GAC ATC CAG ATG ACC CAG AGC CCA AGC AGC CTG AGC GCC              96

```
Val His Ser Asp Ile Gln Met Thr Gln Ser Pro Ser Ser Leu Ser Ala
         1               5                  10

AGC GTG GGT GAC AGA GTG TCC GTC ACC TGT AAG GCC AGT CAG AAT GTG     144
Ser Val Gly Asp Arg Val Ser Val Thr Cys Lys Ala Ser Gln Asn Val
     15                  20                  25

GGT ACT AAT GTA GCC TGG TAC CAG CAG AAG CCA GGA CAG AGT CCA AAG     192
Gly Thr Asn Val Ala Trp Tyr Gln Gln Lys Pro Gly Gln Ser Pro Lys
 30              35                  40                      45

CCG CTG ATC TAC TCG GCA TCC TAT CGG TAC AGT GGT GTG CCA AGC AGA     240
Pro Leu Ile Tyr Ser Ala Ser Tyr Arg Tyr Ser Gly Val Pro Ser Arg
             50                  55                  60

TTC AGC GGT AGC GGT AGC GGT ACC GAC TTC ACC TTG ACC ATC AGC AGC     288
Phe Ser Gly Ser Gly Ser Gly Thr Asp Phe Thr Leu Thr Ile Ser Ser
                 65                  70                  75

CTC CAG CCA GAG GAC ATC GCC ACC TAC TTC TGC CAG CAA TAT AAC AGC     336
Leu Gln Pro Glu Asp Ile Ala Thr Tyr Phe Cys Gln Gln Tyr Asn Ser
             80                  85                  90

TAT CCT CGG GCG TTC GGC CAA GGG ACC AAG GTG GAA ATC AAA             378
Tyr Pro Arg Ala Phe Gly Gln Gly Thr Lys Val Glu Ile Lys
         95                 100                 105

C                                                                   379
```

(2) INFORMATION FOR SEQ ID NO:69:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:69:

```
Met Gly Trp Ser Cys Ile Ile Leu Ser Leu Val Ala Thr Ala Thr Gly
-19             -15                 -10                  -5

Val His Ser Asp Ile Gln Met Thr Gln Ser Pro Ser Ser Leu Ser Ala
         1               5                  10

Ser Val Gly Asp Arg Val Ser Val Thr Cys Lys Ala Ser Gln Asn Val
     15                  20                  25

Gly Thr Asn Val Ala Trp Tyr Gln Gln Lys Pro Gly Gln Ser Pro Lys
 30              35                  40                      45

Pro Leu Ile Tyr Ser Ala Ser Tyr Arg Tyr Ser Gly Val Pro Ser Arg
             50                  55                  60

Phe Ser Gly Ser Gly Ser Gly Thr Asp Phe Thr Leu Thr Ile Ser Ser
                 65                  70                  75

Leu Gln Pro Glu Asp Ile Ala Thr Tyr Phe Cys Gln Gln Tyr Asn Ser
             80                  85                  90

Tyr Pro Arg Ala Phe Gly Gln Gly Thr Lys Val Glu Ile Lys
         95                 100                 105
```

(2) INFORMATION FOR SEQ ID NO:70:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:70:

GAGGACATCG CTGACTACTT CTGCCA                                      26

(2) INFORMATION FOR SEQ ID NO:71:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:71:

AAGTAGTCAG CGATGTCCTC TGGCTG                                  26

(2) INFORMATION FOR SEQ ID NO:72:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58..378

(xi) SEQUENCE DESCRIPTION: SEQ ID NO:72:

```
ATG GGA TGG AGC TGT ATC ATC CTC TCC TTG GTA GCA ACA GCT ACA GGT        48
Met Gly Trp Ser Cys Ile Ile Leu Ser Leu Val Ala Thr Ala Thr Gly
-19             -15                 -10                 -5

GTC CAC TCC GAC ATC CAG ATG ACC CAG AGC CCA AGC AGC CTG AGC GCC        96
Val His Ser Asp Ile Gln Met Thr Gln Ser Pro Ser Ser Leu Ser Ala
                  1               5                  10

AGC GTG GGT GAC AGA GTG TCC GTC ACC TGT AAG GCC AGT CAG AAT GTG       144
Ser Val Gly Asp Arg Val Ser Val Thr Cys Lys Ala Ser Gln Asn Val
         15                  20                  25

GGT ACT AAT GTA GCC TGG TAC CAG CAG AAG CCA GGA CAG AGT CCA AAG       192
Gly Thr Asn Val Ala Trp Tyr Gln Gln Lys Pro Gly Gln Ser Pro Lys
 30                  35                  40                  45

CCG CTG ATC TAC TCG GCA TCC TAT CGG TAC AGT GGT GTG CCA AGC AGA       240
Pro Leu Ile Tyr Ser Ala Ser Tyr Arg Tyr Ser Gly Val Pro Ser Arg
                 50                  55                  60

TTC AGC GGT AGC GGT AGC GGT ACC GAC TTC ACC TTG ACC ATC AGC AGC       288
Phe Ser Gly Ser Gly Ser Gly Thr Asp Phe Thr Leu Thr Ile Ser Ser
                     65                  70                  75

CTC CAG CCA GAG GAC ATC GCC GAC TAC TTC TGC CAG CAA TAT AAC AGC       336
Leu Gln Pro Glu Asp Ile Ala Asp Tyr Phe Cys Gln Gln Tyr Asn Ser
                 80                  85                  90

TAT CCT CGG GCG TTC GGC CAA GGG ACC AAG GTG GAA ATC AAA              378
Tyr Pro Arg Ala Phe Gly Gln Gly Thr Lys Val Glu Ile Lys
         95                 100                 105

C                                                                    379
```

(2) INFORMATION FOR SEQ ID NO:73:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:73:

```
Met Gly Trp Ser Cys Ile Ile Leu Ser Leu Val Ala Thr Ala Thr Gly
-19             -15                 -10                 -5
```

```
Val His Ser Asp Ile Gln Met Thr Gln Ser Pro Ser Ser Leu Ser Ala
         1               5                   10
Ser Val Gly Asp Arg Val Ser Val Thr Cys Lys Ala Ser Gln Asn Val
    15                  20                  25
Gly Thr Asn Val Ala Trp Tyr Gln Gln Lys Pro Gly Gln Ser Pro Lys
 30                  35                  40                  45
Pro Leu Ile Tyr Ser Ala Ser Tyr Arg Tyr Ser Gly Val Pro Ser Arg
                 50                  55                  60
Phe Ser Gly Ser Gly Ser Gly Thr Asp Phe Thr Leu Thr Ile Ser Ser
             65                  70                  75
Leu Gln Pro Glu Asp Ile Ala Asp Tyr Phe Cys Gln Gln Tyr Asn Ser
         80                  85                  90
Tyr Pro Arg Ala Phe Gly Gln Gly Thr Lys Val Glu Ile Lys
     95                 100                 105
```

(2) INFORMATION FOR SEQ ID NO:74:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58..378

(xi) SEQUENCE DESCRIPTION: SEQ ID NO:74:

```
ATG GGA TGG AGC TGT ATC ATC CTC TCC TTG GTA GCA ACA GCT ACA GGT      48
Met Gly Trp Ser Cys Ile Ile Leu Ser Leu Val Ala Thr Ala Thr Gly
-19             -15                 -10                 -5

GTC CAC TCC GAC ATC CAG ATG ACC CAG AGC CCA AGC AGC CTG AGC GCC      96
Val His Ser Asp Ile Gln Met Thr Gln Ser Pro Ser Ser Leu Ser Ala
         1               5                   10

AGC GTG GGT GAC AGA GTG TCC GTC ACC TGT AAG GCC AGT CAG AAT GTG     144
Ser Val Gly Asp Arg Val Ser Val Thr Cys Lys Ala Ser Gln Asn Val
    15                  20                  25

GGT ACT AAT GTA GCC TGG TAC CAG CAG AAG CCA GGA AAG GCT CCA AAG     192
Gly Thr Asn Val Ala Trp Tyr Gln Gln Lys Pro Gly Lys Ala Pro Lys
 30                  35                  40                  45

CTG CTG ATC TAC TCG GCA TCC TAT CGG TAC AGT GGT GTG CCA AGC AGA     240
Leu Leu Ile Tyr Ser Ala Ser Tyr Arg Tyr Ser Gly Val Pro Ser Arg
                 50                  55                  60

TTC AGC GGT AGC GGT AGC GGT ACC GAC TTC ACC TTG ACC ATC AGC AGC     288
Phe Ser Gly Ser Gly Ser Gly Thr Asp Phe Thr Leu Thr Ile Ser Ser
             65                  70                  75

CTC CAG CCA GAG GAC ATC GCC GAC TAC TTC TGC CAG CAA TAT AAC AGC     336
Leu Gln Pro Glu Asp Ile Ala Asp Tyr Phe Cys Gln Gln Tyr Asn Ser
         80                  85                  90

TAT CCT CGG GCG TTC GGC CAA GGG ACC AAG GTG GAA ATC AAA             378
Tyr Pro Arg Ala Phe Gly Gln Gly Thr Lys Val Glu Ile Lys
     95                 100                 105

C                                                                   379
```

(2) INFORMATION FOR SEQ ID NO:75:

(i) SEQUENCE CHARACTERISTICS:

(A) LENGTH: 126 amino acids
            (B) TYPE: amino acid
            (D) TOPOLOGY: linear (ii) MOLECULE TYPE: protein (xi) SEQUENCE DESCRIPTION: SEQ ID NO:75:

```
Met Gly Trp Ser Cys Ile Ile Leu Ser Leu Val Ala Thr Ala Thr Gly
-19             -15                 -10                 -5

Val His Ser Asp Ile Gln Met Thr Gln Ser Pro Ser Ser Leu Ser Ala
         1               5                  10

Ser Val Gly Asp Arg Val Ser Val Thr Cys Lys Ala Ser Gln Asn Val
     15              20                  25

Gly Thr Asn Val Ala Trp Tyr Gln Gln Lys Pro Gly Lys Ala Pro Lys
 30              35                  40                  45

Leu Leu Ile Tyr Ser Ala Ser Tyr Arg Tyr Ser Gly Val Pro Ser Arg
             50                  55                  60

Phe Ser Gly Ser Gly Ser Gly Thr Asp Phe Thr Leu Thr Ile Ser Ser
             65                  70                  75

Leu Gln Pro Glu Asp Ile Ala Asp Tyr Phe Cys Gln Gln Tyr Asn Ser
             80                  85                  90

Tyr Pro Arg Ala Phe Gly Gln Gly Thr Lys Val Glu Ile Lys
             95                 100                 105
```

(2) INFORMATION FOR SEQ ID NO:76:

(i) SEQUENCE CHARACTERISTICS:
            (A) LENGTH: 379 base pairs
            (B) TYPE: nucleic acid
            (C) STRANDEDNESS: double
            (D) TOPOLOGY: linear (ix) FEATURE:
            (A) NAME/KEY: CDS
            (B) LOCATION: 1..378

(ix) FEATURE:
            (A) NAME/KEY: mat_peptide
            (B) LOCATION: 58..378

(xi) SEQUENCE DESCRIPTION: SEQ ID NO:76:

```
ATG GGA TGG AGC TGT ATC ATC CTC TCC TTG GTA GCA ACA GCT ACA GGT      48
Met Gly Trp Ser Cys Ile Ile Leu Ser Leu Val Ala Thr Ala Thr Gly
-19             -15                 -10                 -5

GTC CAC TCC GAC ATC CAG ATG ACC CAG AGC CCA AGC AGC CTG AGC GCC      96
Val His Ser Asp Ile Gln Met Thr Gln Ser Pro Ser Ser Leu Ser Ala
         1               5                  10

AGC GTG GGT GAC AGA GTG TCC GTC ACC TGT AAG GCC AGT CAG AAT GTG     144
Ser Val Gly Asp Arg Val Ser Val Thr Cys Lys Ala Ser Gln Asn Val
     15              20                  25

GGT ACT AAT GTA GCC TGG TAC CAG CAG AAG CCA GGA CAG AGT CCA AAG     192
Gly Thr Asn Val Ala Trp Tyr Gln Gln Lys Pro Gly Gln Ser Pro Lys
 30              35                  40                  45

CCG CTG ATC TAC TCG GCA TCC TAT CGG TAC AGT GGT GTG CCA AGC AGA     240
Pro Leu Ile Tyr Ser Ala Ser Tyr Arg Tyr Ser Gly Val Pro Ser Arg
             50                  55                  60

TTC AGC GGT AGC GGT AGC GGT ACC GAC TTC ACC TTC ACC ATC AGC AGC     288
Phe Ser Gly Ser Gly Ser Gly Thr Asp Phe Thr Phe Thr Ile Ser Ser
             65                  70                  75

CTC CAG CCA GAG GAC ATC GCC ACC TAC TAC TGC CAG CAA TAT AAC AGC     336
Leu Gln Pro Glu Asp Ile Ala Thr Tyr Tyr Cys Gln Gln Tyr Asn Ser
             80                  85                  90
```

```
TAT CCT CGG GCG TTC GGC CAA GGG ACC AAG GTG GAA ATC AAA        378
Tyr Pro Arg Ala Phe Gly Gln Gly Thr Lys Val Glu Ile Lys
         95                 100                 105

C                                                              379
```

(2) INFORMATION FOR SEQ ID NO:77:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:77:

```
Met Gly Trp Ser Cys Ile Ile Leu Ser Leu Val Ala Thr Ala Thr Gly
-19             -15                 -10                 -5

Val His Ser Asp Ile Gln Met Thr Gln Ser Pro Ser Ser Leu Ser Ala
              1                 5                  10

Ser Val Gly Asp Arg Val Ser Val Thr Cys Lys Ala Ser Gln Asn Val
             15                 20                 25

Gly Thr Asn Val Ala Trp Tyr Gln Gln Lys Pro Gly Gln Ser Pro Lys
         30                 35                 40                 45

Pro Leu Ile Tyr Ser Ala Ser Tyr Arg Tyr Ser Gly Val Pro Ser Arg
             50                 55                 60

Phe Ser Gly Ser Gly Ser Gly Thr Asp Phe Thr Phe Thr Ile Ser Ser
         65                 70                 75

Leu Gln Pro Glu Asp Ile Ala Thr Tyr Tyr Cys Gln Gln Tyr Asn Ser
         80                 85                 90

Tyr Pro Arg Ala Phe Gly Gln Gly Thr Lys Val Glu Ile Lys
         95                 100                 105
```

(2) INFORMATION FOR SEQ ID NO:78:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:78:

```
CAGAGCCAAA AGTTCCTGAG CGCCAG                                   26
```

(2) INFORMATION FOR SEQ ID NO:79:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:79:

```
CTCAGGAACT TTTGGCTCTG GGTCAT                                   26
```

(2) INFORMATION FOR SEQ ID NO:80:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS -continued (B) LOCATION: 1..378

(ix) FEATURE:
        (A) NAME/KEY: mat_peptide
        (B) LOCATION: 58..378

(xi) SEQUENCE DESCRIPTION: SEQ ID NO:80:

```
ATG GGA TGG AGC TGT ATC ATC CTC TCC TTG GTA GCA ACA GCT ACA GGT        48
Met Gly Trp Ser Cys Ile Ile Leu Ser Leu Val Ala Thr Ala Thr Gly
-19             -15             -10                 -5

GTC CAC TCC GAC ATC CAG ATG ACC CAG AGC CAA AAG TTC CTG AGC GCC        96
Val His Ser Asp Ile Gln Met Thr Gln Ser Gln Lys Phe Leu Ser Ala
            1               5                   10

AGC GTG GGT GAC AGA GTG ACC ATC ACC TGT AAG GCC AGT CAG AAT GTG       144
Ser Val Gly Asp Arg Val Thr Ile Thr Cys Lys Ala Ser Gln Asn Val
    15              20                  25

GGT ACT AAT GTA GCC TGG TAC CAG CAG AAG CCA GGA CAG AGT CCA AAG       192
Gly Thr Asn Val Ala Trp Tyr Gln Gln Lys Pro Gly Gln Ser Pro Lys
30              35                  40                  45

CCG CTG ATC TAC TCG GCA TCC TAT CGG TAC AGT GGT GTG CCA AGC AGA       240
Pro Leu Ile Tyr Ser Ala Ser Tyr Arg Tyr Ser Gly Val Pro Ser Arg
                50                  55                  60

TTC AGC GGT AGC GGT AGC GGT ACC GAC TTC ACC TTC ACC ATC AGC AGC       288
Phe Ser Gly Ser Gly Ser Gly Thr Asp Phe Thr Phe Thr Ile Ser Ser
                65                  70                  75

CTC CAG CCA GAG GAC ATC GCC ACC TAC TAC TGC CAG CAA TAT AAC AGC       336
Leu Gln Pro Glu Asp Ile Ala Thr Tyr Tyr Cys Gln Gln Tyr Asn Ser
            80                  85                  90

TAT CCT CGG GCG TTC GGC CAA GGG ACC AAG GTG GAA ATC AAA               378
Tyr Pro Arg Ala Phe Gly Gln Gly Thr Lys Val Glu Ile Lys
        95                  100                 105

C                                                                      379
```

(2) INFORMATION FOR SEQ ID NO:81:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:81:

```
Met Gly Trp Ser Cys Ile Ile Leu Ser Leu Val Ala Thr Ala Thr Gly
-19             -15             -10                 -5

Val His Ser Asp Ile Gln Met Thr Gln Ser Gln Lys Phe Leu Ser Ala
            1               5                   10

Ser Val Gly Asp Arg Val Thr Ile Thr Cys Lys Ala Ser Gln Asn Val
    15              20                  25

Gly Thr Asn Val Ala Trp Tyr Gln Gln Lys Pro Gly Gln Ser Pro Lys
30              35                  40                  45

Pro Leu Ile Tyr Ser Ala Ser Tyr Arg Tyr Ser Gly Val Pro Ser Arg
                50                  55                  60

Phe Ser Gly Ser Gly Ser Gly Thr Asp Phe Thr Phe Thr Ile Ser Ser
                65                  70                  75

Leu Gln Pro Glu Asp Ile Ala Thr Tyr Tyr Cys Gln Gln Tyr Asn Ser
            80                  85                  90

Tyr Pro Arg Ala Phe Gly Gln Gly Thr Lys Val Glu Ile Lys
        95                  100                 105
```

(2) INFORMATION FOR SEQ ID NO:82:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:82:

GGACAGAGTC CAAAGCTGCT GATCTACTC                                            29

(2) INFORMATION FOR SEQ ID NO:83:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:83:

ATCAGCAGCT TTGGACTCTG TCCTGGCTT                                            29

(2) INFORMATION FOR SEQ ID NO:84:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58..378

(xi) SEQUENCE DESCRIPTION: SEQ ID NO:84:

```
ATG GGA TGG AGC TGT ATC ATC CTC TCC TTG GTA GCA ACA GCT ACA GGT         48
Met Gly Trp Ser Cys Ile Ile Leu Ser Leu Val Ala Thr Ala Thr Gly
-19         -15                 -10                 -5

GTC CAC TCC GAC ATC CAG ATG ACC CAG AGC CCA AGC AGC CTG AGC GCC         96
Val His Ser Asp Ile Gln Met Thr Gln Ser Pro Ser Ser Leu Ser Ala
              1               5                  10

AGC GTG GGT GAC AGA GTG ACC ATC ACC TGT AAG GCC AGT CAG AAT GTG        144
Ser Val Gly Asp Arg Val Thr Ile Thr Cys Lys Ala Ser Gln Asn Val
        15                  20                  25

GGT ACT AAT GTA GCC TGG TAC CAG CAG AAG CCA GGA CAG AGT CCA AAG        192
Gly Thr Asn Val Ala Trp Tyr Gln Gln Lys Pro Gly Gln Ser Pro Lys
  30                  35                  40                  45

CTG CTG ATC TAC TCG GCA TCC TAT CGG TAC AGT GGT GTG CCA AGC AGA        240
Leu Leu Ile Tyr Ser Ala Ser Tyr Arg Tyr Ser Gly Val Pro Ser Arg
              50                  55                  60

TTC AGC GGT AGC GGT AGC GGT ACC GAC TTC ACC TTC ACC ATC AGC AGC        288
Phe Ser Gly Ser Gly Ser Gly Thr Asp Phe Thr Phe Thr Ile Ser Ser
          65                  70                  75

CTC CAG CCA GAG GAC ATC GCC ACC TAC TAC TGC CAG CAA TAT AAC AGC        336
Leu Gln Pro Glu Asp Ile Ala Thr Tyr Tyr Cys Gln Gln Tyr Asn Ser
      80                  85                  90

TAT CCT CGG GCG TTC GGC CAA GGG ACC AAG GTG GAA ATC AAA                378
Tyr Pro Arg Ala Phe Gly Gln Gly Thr Lys Val Glu Ile Lys
  95                 100                 105

C                                                                      379
```

(2) INFORMATION FOR SEQ ID NO:85:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:85:

```
Met Gly Trp Ser Cys Ile Ile Leu Ser Leu Val Ala Thr Ala Thr Gly
-19             -15                 -10                 -5

Val His Ser Asp Ile Gln Met Thr Gln Ser Pro Ser Ser Leu Ser Ala
             1               5                  10

Ser Val Gly Asp Arg Val Thr Ile Thr Cys Lys Ala Ser Gln Asn Val
         15                  20                  25

Gly Thr Asn Val Ala Trp Tyr Gln Gln Lys Pro Gly Gln Ser Pro Lys
 30                  35                  40                  45

Leu Leu Ile Tyr Ser Ala Ser Tyr Arg Tyr Ser Gly Val Pro Ser Arg
                 50                  55                  60

Phe Ser Gly Ser Gly Ser Gly Thr Asp Phe Thr Phe Thr Ile Ser Ser
             65                  70                  75

Leu Gln Pro Glu Asp Ile Ala Thr Tyr Tyr Cys Gln Gln Tyr Asn Ser
         80                  85                  90

Tyr Pro Arg Ala Phe Gly Gln Gly Thr Lys Val Glu Ile Lys
     95                 100                 105
```

(2) INFORMATION FOR SEQ ID NO:86:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58..378

(xi) SEQUENCE DESCRIPTION: SEQ ID NO:86:

```
ATG GGA TGG AGC TGT ATC ATC CTC TCC TTG GTA GCA ACA GCT ACA GGT        48
Met Gly Trp Ser Cys Ile Ile Leu Ser Leu Val Ala Thr Ala Thr Gly
-19             -15                 -10                 -5

GTC CAC TCC GAC ATC CAG ATG ACC CAG AGC CCA AGC AGC CTG AGC GCC        96
Val His Ser Asp Ile Gln Met Thr Gln Ser Pro Ser Ser Leu Ser Ala
             1               5                  10

AGC GTG GGT GAC AGA GTG ACC ATC ACC TGT AAG GCC AGT CAG AAT GTG       144
Ser Val Gly Asp Arg Val Thr Ile Thr Cys Lys Ala Ser Gln Asn Val
         15                  20                  25

GGT ACT AAT GTA GCC TGG TAC CAG CAG AAG CCA GGA CAG AGT CCA AAG       192
Gly Thr Asn Val Ala Trp Tyr Gln Gln Lys Pro Gly Gln Ser Pro Lys
 30                  35                  40                  45

CCG CTG ATC TAC TCG GCA TCC TAT CGG TAC AGT GGT GTG CCA AGC AGA       240
Pro Leu Ile Tyr Ser Ala Ser Tyr Arg Tyr Ser Gly Val Pro Ser Arg
                 50                  55                  60

TTC AGC GGT AGC GGT AGC GGT ACC GAC TTC ACC TTC ACC ATC AGC AGC       288
Phe Ser Gly Ser Gly Ser Gly Thr Asp Phe Thr Phe Thr Ile Ser Ser
             65                  70                  75

CTC CAG CCA GAG GAC ATC GCC ACC TAC TAC TGC CAG CAA TAT AAC AGC       336
```

```
Leu Gln Pro Glu Asp Ile Ala Thr Tyr Tyr Cys Gln Gln Tyr Asn Ser
        80                  85                  90

TAT CCT CGG GCG TTC GGC CAA GGG ACC AAG GTG GAA ATC AAA                378
Tyr Pro Arg Ala Phe Gly Gln Gly Thr Lys Val Glu Ile Lys
    95                 100                 105

C                                                                      379
```

(2) INFORMATION FOR SEQ ID NO:87:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:87:

```
Met Gly Trp Ser Cys Ile Ile Leu Ser Leu Val Ala Thr Ala Thr Gly
-19             -15                 -10                 -5

Val His Ser Asp Ile Gln Met Thr Gln Ser Pro Ser Ser Leu Ser Ala
                 1               5                  10

Ser Val Gly Asp Arg Val Thr Ile Thr Cys Lys Ala Ser Gln Asn Val
        15                  20                  25

Gly Thr Asn Val Ala Trp Tyr Gln Gln Lys Pro Gly Gln Ser Pro Lys
30                  35                  40                  45

Pro Leu Ile Tyr Ser Ala Ser Tyr Arg Tyr Ser Gly Val Pro Ser Arg
            50                  55                  60

Phe Ser Gly Ser Gly Ser Gly Thr Asp Phe Thr Phe Thr Ile Ser Ser
                65                  70                  75

Leu Gln Pro Glu Asp Ile Ala Thr Tyr Tyr Cys Gln Gln Tyr Asn Ser
        80                  85                  90

Tyr Pro Arg Ala Phe Gly Gln Gly Thr Lys Val Glu Ile Lys
    95                 100                 105
```

(2) INFORMATION FOR SEQ ID NO:88:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:88:

```
GCTCCAAAGC CGCTGATCTA CTC                                              23
```

(2) INFORMATION FOR SEQ ID NO:89:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:89:

```
TAGATCAGCG GCTTTGGAGC CTT                                              23
```

(2) INFORMATION FOR SEQ ID NO:90:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 58..378

(xi) SEQUENCE DESCRIPTION: SEQ ID NO:90:

```
ATG GGA TGG AGC TGT ATC ATC CTC TCC TTG GTA GCA ACA GCT ACA GGT        48
Met Gly Trp Ser Cys Ile Ile Leu Ser Leu Val Ala Thr Ala Thr Gly
-19             -15                 -10                 -5

GTC CAC TCC GAC ATC CAG ATG ACC CAG AGC CCA AGC AGC CTG AGC GCC        96
Val His Ser Asp Ile Gln Met Thr Gln Ser Pro Ser Ser Leu Ser Ala
                 1               5                  10

AGC GTG GGT GAC AGA GTG ACC ATC ACC TGT AAG GCC AGT CAG AAT GTG       144
Ser Val Gly Asp Arg Val Thr Ile Thr Cys Lys Ala Ser Gln Asn Val
        15                  20                  25

GGT ACT AAT GTA GCC TGG TAC CAG CAG AAG CCA GGA AAG GCT CCA AAG       192
Gly Thr Asn Val Ala Trp Tyr Gln Gln Lys Pro Gly Lys Ala Pro Lys
30                  35                  40                  45

CCG CTG ATC TAC TCG GCA TCC TAT CGG TAC AGT GGT GTG CCA AGC AGA       240
Pro Leu Ile Tyr Ser Ala Ser Tyr Arg Tyr Ser Gly Val Pro Ser Arg
            50                  55                  60

TTC AGC GGT AGC GGT AGC GGT ACC GAC TTC ACC TTC ACC ATC AGC AGC       288
Phe Ser Gly Ser Gly Ser Gly Thr Asp Phe Thr Phe Thr Ile Ser Ser
                65                  70                  75

CTC CAG CCA GAG GAC ATC GCC ACC TAC TAC TGC CAG CAA TAT AAC AGC       336
Leu Gln Pro Glu Asp Ile Ala Thr Tyr Tyr Cys Gln Gln Tyr Asn Ser
            80                  85                  90

TAT CCT CGG GCG TTC GGC CAA GGG ACC AAG GTG GAA ATC AAA               378
Tyr Pro Arg Ala Phe Gly Gln Gly Thr Lys Val Glu Ile Lys
        95                  100                 105

C                                                                     379
```

(2) INFORMATION FOR SEQ ID NO:91:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:91:

```
Met Gly Trp Ser Cys Ile Ile Leu Ser Leu Val Ala Thr Ala Thr Gly
-19             -15                 -10                 -5

Val His Ser Asp Ile Gln Met Thr Gln Ser Pro Ser Ser Leu Ser Ala
                 1               5                  10

Ser Val Gly Asp Arg Val Thr Ile Thr Cys Lys Ala Ser Gln Asn Val
        15                  20                  25

Gly Thr Asn Val Ala Trp Tyr Gln Gln Lys Pro Gly Lys Ala Pro Lys
30                  35                  40                  45

Pro Leu Ile Tyr Ser Ala Ser Tyr Arg Tyr Ser Gly Val Pro Ser Arg
            50                  55                  60

Phe Ser Gly Ser Gly Ser Gly Thr Asp Phe Thr Phe Thr Ile Ser Ser
                65                  70                  75

Leu Gln Pro Glu Asp Ile Ala Thr Tyr Tyr Cys Gln Gln Tyr Asn Ser
            80                  85                  90

Tyr Pro Arg Ala Phe Gly Gln Gly Thr Lys Val Glu Ile Lys
```

(2) INFORMATION FOR SEQ ID NO:92:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (xi) SEQUENCE DESCRIPTION: SEQ ID NO:92:

```
AAGAAGCCTG GGTCCTCAGT GAAGGTCTCC TGCAAGGCTT CTGGCTTCAA CATTAAAGAC      60

ACCTATATAC ACTGGGTGCG CCAGGCTCCA GGACAGGGCC TGGAGTGGAT GGGAAGGATT     120

GATCCTGAGG ATGGTAA                                                    137
```

(2) INFORMATION FOR SEQ ID NO:93:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (xi) SEQUENCE DESCRIPTION: SEQ ID NO:93:

```
TGAGATCTGA GGACACAGCC TTTTATTTCT GTGCAAGTGC CTACTATGTT AACCAGGACT      60

ACTGGGGCCA AGGGACCACT GTCACCGTCT CCTCAGGTGA GTGGATCCGA C              111
```

(2) INFORMATION FOR SEQ ID NO:94:

(i) SEQUENCE CHARACTERISTICS:
        (A) LENGTH: 130 base pairs
        (B) TYPE: nucleic acid
        (C) STRANDEDNESS: single
        (D) TOPOLOGY: linear (xi) SEQUENCE DESCRIPTION: SEQ ID NO:94:

```
ACCTTCACTG AGGACCCAGG CTTCTTCACC TCAGCTCCAG ACTGCACCAG CTGCACCTGG      60

GAGTGAGCAC CTGGAGCTAC AGCCAGCAAG AAGAAGACCC TCCAGGTCCA GTCCATGGTC     120

GAAGCTTATC                                                            130
```

(2) INFORMATION FOR SEQ ID NO:95:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (xi) SEQUENCE DESCRIPTION: SEQ ID NO:95:

```
AAAGGCTGTG TCCTCAGATC TCAGGCTGCT GAGCTCCATG TAGGCTGTGT TCGTGGATTC      60

GTCTGCAGTG ATTGTGACTC GGCCCTGGAA CTTCGGGTCA TATTTAGTAT TACCATCCGC     120

AGGATCAATC CT                                                         132
```

(2) INFORMATION FOR SEQ ID NO:96:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:96:

```
GATAAGCTTC CACCATGGAC TGGAC                                                25
```

(2) INFORMATION FOR SEQ ID NO:97:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:97:

```
GTCGGATCCA CTCACCTGAG GAGAC                                                25
```

(2) INFORMATION FOR SEQ ID NO:98:

(i) SEQUENCE CHARACTERISTICS:
        (A) LENGTH: 409 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..408

(ix) FEATURE:
        (A) NAME/KEY: mat_peptide
        (B) LOCATION: 58..408

(xi) SEQUENCE DESCRIPTION: SEQ ID NO:98:

```
ATG GAC TGG ACC TGG AGG GTC TTC TTC TTG CTG GCT GTA GCT CCA GGT            48
Met Asp Trp Thr Trp Arg Val Phe Phe Leu Leu Ala Val Ala Pro Gly
-19             -15                 -10                 -5

GCT CAC TCC CAG GTG CAG CTG GTG CAG TCT GGA GCT GAG GTG AAG AAG            96
Ala His Ser Gln Val Gln Leu Val Gln Ser Gly Ala Glu Val Lys Lys
                1               5                   10

CCT GGG TCC TCA GTG AAG GTC TCC TGC AAG GCT TCT GGC TTC AAC ATT           144
Pro Gly Ser Ser Val Lys Val Ser Cys Lys Ala Ser Gly Phe Asn Ile
        15                  20                  25

AAA GAC ACC TAT ATA CAC TGG GTG CGC CAG GCT CCA GGA CAG GGC CTG           192
Lys Asp Thr Tyr Ile His Trp Val Arg Gln Ala Pro Gly Gln Gly Leu
 30                  35                  40                  45

GAG TGG ATG GGA AGG ATT GAT CCT GCG GAT GGT AAT ACT AAA TAT GAC           240
Glu Trp Met Gly Arg Ile Asp Pro Ala Asp Gly Asn Thr Lys Tyr Asp
                50                  55                  60

CCG AAG TTC CAG GGC CGA GTC ACA ATC ACT GCA GAC GAA TCC ACG AAC           288
Pro Lys Phe Gln Gly Arg Val Thr Ile Thr Ala Asp Glu Ser Thr Asn
            65                  70                  75

ACA GCC TAC ATG GAG CTC AGC AGC CTG AGA TCT GAG GAC ACA GCC TTT           336
Thr Ala Tyr Met Glu Leu Ser Ser Leu Arg Ser Glu Asp Thr Ala Phe
        80                  85                  90

TAT TTC TGT GCA AGT GCC TAC TAT GTT AAC CAG GAC TAC TGG GGC CAA           384
Tyr Phe Cys Ala Ser Ala Tyr Tyr Val Asn Gln Asp Tyr Trp Gly Gln
    95                  100                 105

GGG ACC ACT GTC ACC GTC TCC TCA G                                         409
Gly Thr Thr Val Thr Val Ser Ser
110             115
```

(2) INFORMATION FOR SEQ ID NO:99:

(i) SEQUENCE CHARACTERISTICS:
        (A) LENGTH: 136 amino acids
        (B) TYPE: amino acid
        (D) TOPOLOGY: linear (ii) MOLECULE TYPE: protein (xi) SEQUENCE DESCRIPTION: SEQ ID NO:99:

Met Asp Trp Thr Trp Arg Val Phe Phe Leu Leu Ala Val Ala Pro Gly
-19             -15                 -10                 -5

Ala His Ser Gln Val Gln Leu Val Gln Ser Gly Ala Glu Val Lys Lys
            1               5                   10

Pro Gly Ser Ser Val Lys Val Ser Cys Lys Ala Ser Gly Phe Asn Ile
        15              20                  25

Lys Asp Thr Tyr Ile His Trp Val Arg Gln Ala Pro Gly Gln Gly Leu
30              35                  40                  45

Glu Trp Met Gly Arg Ile Asp Pro Ala Asp Gly Asn Thr Lys Tyr Asp
                50                  55                  60

Pro Lys Phe Gln Gly Arg Val Thr Ile Thr Ala Asp Glu Ser Thr Asn
            65                  70                  75

Thr Ala Tyr Met Glu Leu Ser Ser Leu Arg Ser Glu Asp Thr Ala Phe
            80                  85                  90

Tyr Phe Cys Ala Ser Ala Tyr Tyr Val Asn Gln Asp Tyr Trp Gly Gln
            95              100                 105

Gly Thr Thr Val Thr Val Ser Ser
110             115

(2) INFORMATION FOR SEQ ID NO:100:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO:100:

AGCTTGTCAC CGTCTCCTCA GGTGGTGGTG GTTCGGGTGG TGGTGGTTCG GGTGGTGGCG          60

GATCGGACAT CCAGATGACC CAGG                                                 84

(2) INFORMATION FOR SEQ ID NO:101:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO:101:

AATTCCTGGG CCATCTGGAT GTCCGATCCG CCACCACCCG AACCACCACC ACCCGAACCA          60

CCACCACCTG AGGAGACGGT GACA                                                 84

(2) INFORMATION FOR SEQ ID NO:102:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:102:

CAGCCATGGC GCAGTGTGCA GCTGGTGCAG TCTG                                      34

(2) INFORMATION FOR SEQ ID NO:103:

(i) SEQUENCE CHARACTERISTICS:
        (A) LENGTH: 41 base pairs
        (B) TYPE: nucleic acid (C) STRANDEDNESS: single
            (D) TOPOLOGY: linear (xi) SEQUENCE DESCRIPTION: SEQ ID NO:103:

CCACCCGAAC CACCACCACC TGAGGAGACG GTGACAGTGG T                    41

(2) INFORMATION FOR SEQ ID NO:104:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:104:

GGGACCACTG TCACCGTCTC CTCAGGTGGT GGTGGTTCGG G                    41

(2) INFORMATION FOR SEQ ID NO:105:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:105:

GGGCTCTGGG TCATCTGGAT GTCCGATCCG CCACCACCCG A                    41

(2) INFORMATION FOR SEQ ID NO:106:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (xi) SEQUENCE DESCRIPTION: SEQ ID NO:106:

TCGGACATCC AGATGACCCA GAGCCCAAGC AGCCTGAGCG CCAG                 44

(2) INFORMATION FOR SEQ ID NO:107:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (xi) SEQUENCE DESCRIPTION: SEQ ID NO:107:

CAAGAATTCT TATTATTTAT CGTCATCGTC TTTGTAGTCT TGATTTCGA CCTTGGT    57

(2) INFORMATION FOR SEQ ID NO:108:

(i) SEQUENCE CHARACTERISTICS:
            (A) LENGTH: 822 base pairs
            (B) TYPE: nucleic acid
            (C) STRANDEDNESS: double
            (D) TOPOLOGY: linear (ix) FEATURE:
            (A) NAME/KEY: CDS
            (B) LOCATION: 1..807

(ix) FEATURE:
            (A) NAME/KEY: mat_peptide
            (B) LOCATION: 1..807

(xi) SEQUENCE DESCRIPTION: SEQ ID NO:108:

ATG AAA TAC CTA TTG CCT ACG GCA GCC GCT GGA TTG TTA TTA CTC GCT    48

```
Met Lys Tyr Leu Leu Pro Thr Ala Ala Ala Gly Leu Leu Leu Ala
  1               5                  10                  15

GCC CAA CCA GCC ATG GCG CAG GTG CAG CTG GTG CAG TCT GGA GCT GAG    96
Ala Gln Pro Ala Met Ala Gln Val Gln Leu Val Gln Ser Gly Ala Glu
             20                  25                  30

GTG AAG AAG CCT GGG TCC TCA GTG AAG GTC TCC TGC AAG GCT TCT GGC   144
Val Lys Lys Pro Gly Ser Ser Val Lys Val Ser Cys Lys Ala Ser Gly
         35                  40                  45

TTC AAC ATT AAA GAC ACC TAT ATA CAC TGG GTG CGC CAG GCT CCA GGA   192
Phe Asn Ile Lys Asp Thr Tyr Ile His Trp Val Arg Gln Ala Pro Gly
     50                  55                  60

CAG GGC CTG GAG TGG ATG GGA AGG ATT GAT CCT GCG GAT GGT AAT ACT   240
Gln Gly Leu Glu Trp Met Gly Arg Ile Asp Pro Ala Asp Gly Asn Thr
 65                  70                  75                  80

AAA TAT GAC CCG AAG TTC CAG GGC CGA GTC ACA ATC ACT GCA GAC GAA   288
Lys Tyr Asp Pro Lys Phe Gln Gly Arg Val Thr Ile Thr Ala Asp Glu
                 85                  90                  95

TCC ACG AAC ACA GCC TAC ATG GAG CTC AGC AGC CTG AGA TCT GAG GAC   336
Ser Thr Asn Thr Ala Tyr Met Glu Leu Ser Ser Leu Arg Ser Glu Asp
             100                 105                 110

ACA GCC TTT TAT TTC TGT GCA AGT GCC TAC TAT GTT AAC CAG GAC TAC   384
Thr Ala Phe Tyr Phe Cys Ala Ser Ala Tyr Tyr Val Asn Gln Asp Tyr
         115                 120                 125

TGG GGC CAA GGG ACC ACT GTC ACC GTC TCC TCA GGT GGT GGT GGT TCG   432
Trp Gly Gln Gly Thr Thr Val Thr Val Ser Ser Gly Gly Gly Gly Ser
130                 135                 140

GGT GGT GGT GGT TCG GGT GGT GGC GGA TCG GAC ATC CAG ATG ACC CAG   480
Gly Gly Gly Gly Ser Gly Gly Gly Gly Ser Asp Ile Gln Met Thr Gln
145                 150                 155                 160

AGC CCA AGC AGC CTG AGC GCC AGC GTG GGT GAC AGA GTG ACC ATC ACC   528
Ser Pro Ser Ser Leu Ser Ala Ser Val Gly Asp Arg Val Thr Ile Thr
                 165                 170                 175

TGT AAG GCC AGT CAG AAT GTG GGT ACT AAT GTA GCC TGG TAC CAG CAG   576
Cys Lys Ala Ser Gln Asn Val Gly Thr Asn Val Ala Trp Tyr Gln Gln
             180                 185                 190

AAG CCA GGA AAG GCT CCA AAG CCG CTG ATC TAC TCG GCA TCC TAT CGG   624
Lys Pro Gly Lys Ala Pro Lys Pro Leu Ile Tyr Ser Ala Ser Tyr Arg
         195                 200                 205

TAC AGT GGT GTG CCA AGC AGA TTC AGC GGT AGC GGT AGC GGT ACC GAC   672
Tyr Ser Gly Val Pro Ser Arg Phe Ser Gly Ser Gly Ser Gly Thr Asp
210                 215                 220

TTC ACC TTC ACC ATC AGC AGC CTC CAG CCA GAG GAC ATC GCT ACC TAC   720
Phe Thr Phe Thr Ile Ser Ser Leu Gln Pro Glu Asp Ile Ala Thr Tyr
225                 230                 235                 240

TAC TGC CAG CAA TAT AAC AGC TAT CCT CGG GCG TTC GGC CAA GGG ACC   768
Tyr Cys Gln Gln Tyr Asn Ser Tyr Pro Arg Ala Phe Gly Gln Gly Thr
                 245                 250                 255

AAG GTC GAA ATC AAA GAC TAC AAA GAC GAT GAC GAT AAA TAATAAGAAT   817
Lys Val Glu Ile Lys Asp Tyr Lys Asp Asp Asp Asp Lys
             260                 265

TCTTG                                                              822
```

(2) INFORMATION FOR SEQ ID NO:109:

(i) SEQUENCE CHARACTERISTICS:
        (A) LENGTH: 269 amino acids
        (B) TYPE: amino acid
        (D) TOPOLOGY: linear (ii) MOLECULE TYPE: protein (xi) SEQUENCE DESCRIPTION: SEQ ID NO:109:

Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Phe Asn Ile Lys Asp Thr Tyr Ile His Trp Val Arg Gln Ala Pro Gly
    50                  55                  60

Gln Gly Leu Glu Trp Met Gly Arg Ile Asp Pro Ala Asp Gly Asn Thr
65              70                  75                  80

Lys Tyr Asp Pro Lys Phe Gln Gly Arg Val Thr Ile Thr Ala Asp Glu
            85                  90                  95

Ser Thr Asn Thr Ala Tyr Met Glu Leu Ser Ser Leu Arg Ser Glu Asp
            100                 105                 110

Thr Ala Phe Tyr Phe Cys Ala Ser Ala Tyr Tyr Val Asn Gln Asp Tyr
        115                 120                 125

Trp Gly Gln Gly Thr Thr Val Thr Val Ser Ser Gly Gly Gly Gly Ser
130                 135                 140

Gly Gly Gly Gly Ser Gly Gly Gly Gly Ser Asp Ile Gln Met Thr Gln
145                 150                 155                 160

Ser Pro Ser Ser Leu Ser Ala Ser Val Gly Asp Arg Val Thr Ile Thr
            165                 170                 175

Cys Lys Ala Ser Gln Asn Val Gly Thr Asn Val Ala Trp Tyr Gln Gln
            180                 185                 190

Lys Pro Gly Lys Ala Pro Lys Pro Leu Ile Tyr Ser Ala Ser Tyr Arg
        195                 200                 205

Tyr Ser Gly Val Pro Ser Arg Phe Ser Gly Ser Gly Ser Gly Thr Asp
210                 215                 220

Phe Thr Phe Thr Ile Ser Ser Leu Gln Pro Glu Asp Ile Ala Thr Tyr
225                 230                 235                 240

Tyr Cys Gln Gln Tyr Asn Ser Tyr Pro Arg Ala Phe Gly Gln Gly Thr
            245                 250                 255

Lys Val Glu Ile Lys Asp Tyr Lys Asp Asp Asp Lys
        260                 265

(2) INFORMATION FOR SEQ ID NO:110:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..45

(ix) FEATURE:
        (A) NAME/KEY: mat_peptide
        (B) LOCATION: 1..45

(xi) SEQUENCE DESCRIPTION: SEQ ID NO:110:

GGT GGT GGT GGT TCG GGT GGT GGT GGT TCG GGT GGT GGC GGA TCG         45
Gly Gly Gly Gly Ser Gly Gly Gly Gly Ser Gly Gly Gly Gly Ser
1               5                   10                  15

(2) INFORMATION FOR SEQ ID NO:111:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:111:

Gly Gly Gly Gly Ser Gly Gly Gly Gly Ser Gly Gly Gly Gly Ser
1               5                   10                  15

(2) INFORMATION FOR SEQ ID NO:112:

(i) SEQUENCE CHARACTERISTICS:
        (A) LENGTH: 87 amino acids
        (B) TYPE: amino acid
        (D) TOPOLOGY: linear (ii) MOLECULE TYPE: protein (xi) SEQUENCE DESCRIPTION: SEQ ID NO:112:

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
                20                  25                  30

Pro Lys Leu Leu Ile Tyr Ser Ala Ser Tyr Arg Tyr Ser Gly Val Pro
            35                  40                  45

Ser Arg Phe Ser Gly Ser Gly Ser Gly Thr Asp Phe Thr Phe Thr Ile
        50                  55                  60

Ser Ser Leu Gln Pro Glu Asp Ile Ala Thr Tyr Tyr Cys Phe Gly Gln
65                  70                  75                  80

Gly Thr Lys Val Glu Ile Lys
                85

(2) INFORMATION FOR SEQ ID NO:113:

(i) SEQUENCE CHARACTERISTICS:
        (A) LENGTH: 76 amino acids
        (B) TYPE: amino acid
        (D) TOPOLOGY: linear (ii) MOLECULE TYPE: protein (xi) SEQUENCE DESCRIPTION: SEQ ID NO:113:

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Trp Val
                20                  25                  30

Arg Gln Ala Pro Gly Gln Gly Leu Glu Trp Met Gly Arg Val Thr Ile
            35                  40                  45

Thr Ala Asp Glu Ser Thr Asn Thr Ala Tyr Met Glu Leu Ser Ser Leu
        50                  55                  60

Arg Ser Glu Asp Thr Ala Phe Tyr Phe Cys Ala Gly
65                  70                  75

(2) INFORMATION FOR SEQ ID NO:114:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:114:

Trp Gly Gln Gly Thr Thr Val Thr Val Ser Ser
1               5                   10

(2) INFORMATION FOR SEQ ID NO:115:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:115:

Asp Thr Tyr Ile His
1               5

(2) INFORMATION FOR SEQ ID NO:116:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:116:

Arg Ile Asp Pro Ala Asp Gly Asn Thr Lys Tyr Asp Pro Lys Phe Gln
1               5                   10                  15
Gly (2) INFORMATION FOR SEQ ID NO:117:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:117:

Ala Tyr Tyr Val Asn Gln Asp Tyr
1               5

(2) INFORMATION FOR SEQ ID NO:118:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:118:

Lys Ala Ser Gln Asn Val Gly Thr Asn Val Ala
1               5                   10

(2) INFORMATION FOR SEQ ID NO:119:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:119:

```
Ser Ala Ser Tyr Arg Tyr Ser
1               5
```

(2) INFORMATION FOR SEQ ID NO:120:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:120:

```
Gln Gln Tyr Asn Ser Tyr Pro Arg Ala
1               5
```

(2) INFORMATION FOR SEQ ID NO:121:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:121:

```
Asp Ile Gln Met Thr Gln Ser Pro Ser Ser Leu Ser Ala Ser Val Gly
1               5                   10                  15

Asp Arg Val Thr Ile Thr Cys
                20
```

(2) INFORMATION FOR SEQ ID NO:122:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:122:

```
Trp Tyr Gln Gln Lys Pro Gly Lys Ala Pro Lys Pro Leu Ile Tyr
1               5                   10                  15
```

(2) INFORMATION FOR SEQ ID NO:123:

(i) SEQUENCE CHARACTERISTICS:
        (A) LENGTH: 32 amino acids
        (B) TYPE: amino acid
        (D) TOPOLOGY: linear (ii) MOLECULE TYPE: protein (xi) SEQUENCE DESCRIPTION: SEQ ID NO:123:

```
Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
                20                  25                  30
```

(2) INFORMATION FOR SEQ ID NO:124:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:124:

Phe Gly Gln Gly Thr Lys Val Glu Ile Lys
1               5                   10

(2) INFORMATION FOR SEQ ID NO:125:

(i) SEQUENCE CHARACTERISTICS:
      (A) LENGTH: 15 amino acids
      (B) TYPE: amino acid
      (D) TOPOLOGY: linear (ii) MOLECULE TYPE: protein (xi) SEQUENCE DESCRIPTION: SEQ ID NO:125:

Trp Tyr Gln Gln Lys Pro Gly Gln Ser Pro Lys Pro Leu Ile Tyr
1               5                   10                  15

(2) INFORMATION FOR SEQ ID NO:126:

(i) SEQUENCE CHARACTERISTICS:
      (A) LENGTH: 30 amino acids
      (B) TYPE: amino acid
      (D) TOPOLOGY: linear (ii) MOLECULE TYPE: protein (xi) SEQUENCE DESCRIPTION: SEQ ID NO:126:

Gln Val Gln Leu Val Gln Ser Gly Ala Glu Val Lys Lys Pro Gly Ser
1               5                   10                  15
Ser Val Lys Val Ser Cys Lys Ala Ser Gly Phe Asn Ile Lys
            20                  25                  30

(2) INFORMATION FOR SEQ ID NO:127:

(i) SEQUENCE CHARACTERISTICS:
      (A) LENGTH: 14 amino acids
      (B) TYPE: amino acid
      (D) TOPOLOGY: linear (ii) MOLECULE TYPE: protein (xi) SEQUENCE DESCRIPTION: SEQ ID NO:127:

Trp Val Arg Gln Ala Pro Gly Gln Gly Leu Glu Trp Met Gly
1               5                   10

(2) INFORMATION FOR SEQ ID NO:128:

(i) SEQUENCE CHARACTERISTICS:
      (A) LENGTH: 32 amino acids
      (B) TYPE: amino acid
      (D) TOPOLOGY: linear (ii) MOLECULE TYPE: protein (xi) SEQUENCE DESCRIPTION: SEQ ID NO:128:

Arg Val Thr Ile Thr Ala Asp Glu Ser Thr Asn Thr Ala Tyr Met Glu
1               5                   10                  15
Leu Ser Ser Leu Arg Ser Glu Asp Thr Ala Phe Tyr Phe Cys Ala Ser
            20                  25                  30

(2) INFORMATION FOR SEQ ID NO:129:

(i) SEQUENCE CHARACTERISTICS:
      (A) LENGTH: 11 amino acids
      (B) TYPE: amino acid
      (D) TOPOLOGY: linear (ii) MOLECULE TYPE: peptide (xi) SEQUENCE DESCRIPTION: SEQ ID NO:129:

Trp Gly Gln Gly Thr Thr Val Thr Val Ser Ser
1               5                   10

(2) INFORMATION FOR SEQ ID NO:130:

(i) SEQUENCE CHARACTERISTICS:
      (A) LENGTH: 107 amino acids
      (B) TYPE: amino acid
      (D) TOPOLOGY: linear (ii) MOLECULE TYPE: protein (xi) SEQUENCE DESCRIPTION: SEQ ID NO:130:

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Pro Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Ser Tyr Pro Arg
                85                  90                  95

Ala Phe Gly Gln Gly Thr Lys Val Glu Ile Lys
            100                 105

(2) INFORMATION FOR SEQ ID NO:131:

(i) SEQUENCE CHARACTERISTICS:
      (A) LENGTH: 107 amino acids
      (B) TYPE: amino acid
      (D) TOPOLOGY: linear (ii) MOLECULE TYPE: protein (xi) SEQUENCE DESCRIPTION: SEQ ID NO:131:

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Ser Tyr Pro Arg
                85                  90                  95

Ala Phe Gly Gln Gly Thr Lys Val Glu Ile Lys
            100                 105

(2) INFORMATION FOR SEQ ID NO:132:

(i) SEQUENCE CHARACTERISTICS:
      (A) LENGTH: 117 amino acids
      (B) TYPE: amino acid -continued

```
        (D) TOPOLOGY: linear (ii) MOLECULE TYPE: protein (xi) SEQUENCE DESCRIPTION: SEQ ID NO:132:

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Arg Ile Asp Pro Ala Asp Gly Asn Thr Lys Tyr Asp Pro Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Ser Ala Tyr Tyr Val Asn Gln Asp Tyr Trp Gly Gln Gly Thr Thr
                100                 105                 110

Val Thr Val Ser Ser
            115
```